(12) United States Patent
Crooks et al.

(10) Patent No.: US 11,948,112 B2
(45) Date of Patent: Apr. 2, 2024

(54) PHARMACY WORKFLOW MANAGEMENT WITH INTEGRATED ALERTS

(71) Applicant: Baxter Corporation Englewood, Englewood, CO (US)

(72) Inventors: Matthew Crooks, Daytona Beach, FL (US); Robert Hammond, Port Orange, FL (US); Paul Randall, Ross On Wye (GB); Jon Haynes, Gloucester Business Park (GB)

(73) Assignee: Baxter Corporation Engelwood, Englewood, CO (US)

( * ) Notice: Subject to any disclaimer, the term of this patent is extended or adjusted under 35 U.S.C. 154(b) by 832 days.

(21) Appl. No.: 15/060,387

(22) Filed: Mar. 3, 2016

(65) Prior Publication Data

US 2016/0260035 A1 Sep. 8, 2016

Related U.S. Application Data

(60) Provisional application No. 62/127,580, filed on Mar. 3, 2015.

(51) Int. Cl.
*G16H 40/20* (2018.01)
*G06F 3/0482* (2013.01)
(Continued)

(52) U.S. Cl.
CPC ....... *G06Q 10/0633* (2013.01); *G06F 3/0482* (2013.01); *G06F 3/04842* (2013.01);
(Continued)

(58) Field of Classification Search
CPC .................................................. G06Q 10/0633
See application file for complete search history.

(56) References Cited

U.S. PATENT DOCUMENTS

| 641,748 A | 1/1900 | Smith |
| 819,339 A | 5/1906 | Cleland |

(Continued)

FOREIGN PATENT DOCUMENTS

| CN | 1516257 | 5/1999 |
| CN | 2440518 | 8/2001 |

(Continued)

OTHER PUBLICATIONS

Paxton, Anne. "Finally, microbiology labs getting a lift from IT." Cap Today. May 2012. http://www.captodayonline.com/Archives/0512/0512f_finally.html (Year: 2012).*

(Continued)

*Primary Examiner* — Robert A Sorey
*Assistant Examiner* — Kristine K Rapillo
(74) *Attorney, Agent, or Firm* — K&L Gates LLP

(57) ABSTRACT

Pharmacy workflow management with alert integration. A pharmacy workflow management application may obtain alert data from an alert generation platform. In turn, the alert information may be provided to a user of the workflow management application within the application without having to divert from use of the application. The user may further utilize the pharmacy workflow application to access the alert generation platform. In this regard, the user of the pharmacy workflow management application may be in bidirectional communication with the alert generation platform to, for example, exchange resolution information in relation to an alert. The alert data may comprise any pertinent data related to pharmacy activity managed by the pharmacy workflow management application and in particular may include data related to infection control or antimicrobial stewardship.

19 Claims, 14 Drawing Sheets

(51) Int. Cl.
*G06F 3/04842* (2022.01)
*G06Q 10/0633* (2023.01)
*G16H 15/00* (2018.01)
*G16H 20/10* (2018.01)
*G16H 10/60* (2018.01)

(52) U.S. Cl.
CPC ............ *G16H 15/00* (2018.01); *G16H 20/10* (2018.01); *G16H 40/20* (2018.01); *G16H 10/60* (2018.01)

(56) References Cited

U.S. PATENT DOCUMENTS

| | | |
|---|---|---|
| 3,426,150 A | 2/1969 | Tygart |
| 3,739,943 A | 6/1973 | Williamsen et al. |
| 3,742,938 A | 7/1973 | Stern |
| 3,756,752 A | 9/1973 | Stenner |
| 3,774,762 A | 11/1973 | Lichtenstein |
| 3,786,190 A | 1/1974 | Pori |
| 3,809,871 A | 5/1974 | Howard et al. |
| 3,810,102 A | 5/1974 | Parks, III et al. |
| 3,848,112 A | 11/1974 | Weichselbaum et al. |
| 3,858,574 A | 1/1975 | Page |
| 3,878,967 A | 4/1975 | Joslin et al. |
| 3,910,257 A | 10/1975 | Fletcher et al. |
| 3,910,260 A | 11/1975 | Sarnoff et al. |
| 3,921,196 A | 11/1975 | Patterson |
| 3,971,000 A | 7/1976 | Cromwell |
| 3,995,630 A | 12/1976 | Verrdonk |
| 3,998,103 A | 12/1976 | Bjorklund et al. |
| 4,032,908 A | 6/1977 | Rice et al. |
| 4,078,562 A | 3/1978 | Friedman |
| 4,144,496 A | 3/1979 | Cunningham et al. |
| 4,151,407 A | 4/1979 | McBride et al. |
| 4,156,867 A | 5/1979 | Bench et al. |
| 4,164,320 A | 8/1979 | Irazoqui et al. |
| 4,173,971 A | 11/1979 | Karz |
| 4,199,307 A | 4/1980 | Jassawalla |
| 4,270,532 A | 6/1981 | Franetzki et al. |
| 4,273,121 A | 6/1981 | Jassawalla |
| 4,282,872 A | 8/1981 | Franetzki et al. |
| 4,308,866 A | 1/1982 | Jelliffe et al. |
| 4,319,338 A | 3/1982 | Grudowski et al. |
| 4,320,757 A | 3/1982 | Whitney et al. |
| 4,354,252 A | 10/1982 | Lamb et al. |
| 4,369,780 A | 1/1983 | Sakai |
| 4,370,983 A | 2/1983 | Lichtenstein |
| 4,373,527 A | 2/1983 | Fischell |
| 4,381,776 A | 5/1983 | Latham, Jr. |
| 4,385,630 A | 5/1983 | Gilcher et al. |
| 4,398,289 A | 8/1983 | Schoate |
| 4,398,908 A | 8/1983 | Siposs |
| 4,414,566 A | 11/1983 | Peyton et al. |
| 4,416,654 A | 11/1983 | Schoendorfer et al. |
| 4,425,114 A | 1/1984 | Schoendorfer et al. |
| 4,428,381 A | 1/1984 | Hepp |
| 4,443,216 A | 4/1984 | Chappell |
| 4,447,224 A | 5/1984 | DeCant, Jr. et al. |
| 4,449,538 A | 5/1984 | Corbitt et al. |
| 4,451,255 A | 5/1984 | Bujan et al. |
| 4,457,750 A | 7/1984 | Hill |
| 4,458,693 A | 7/1984 | Badzinski et al. |
| 4,460,358 A | 7/1984 | Somerville et al. |
| 4,464,172 A | 8/1984 | Lichtenstein |
| 4,469,481 A | 9/1984 | Kobayashi |
| 4,475,901 A | 10/1984 | Kraegen et al. |
| 4,476,381 A | 10/1984 | Rubin |
| 4,480,751 A | 11/1984 | Lueptow |
| 4,481,670 A | 11/1984 | Freeburg |
| 4,487,604 A | 12/1984 | Iwatschenko et al. |
| 4,490,798 A | 12/1984 | Franks et al. |
| 4,496,351 A | 1/1985 | Hillel et al. |
| 4,511,352 A | 4/1985 | Theeuwes et al. |
| 4,525,861 A | 6/1985 | Freeburg |
| 4,526,574 A | 7/1985 | Pekkarinen |
| 4,529,401 A | 7/1985 | Leslie et al. |
| 4,531,527 A | 7/1985 | Reinhold, Jr. et al. |
| 4,538,138 A | 8/1985 | Harvey et al. |
| 4,545,071 A | 10/1985 | Freeburg |
| 4,551,133 A | 11/1985 | Zegers de Beyl et al. |
| 4,559,038 A | 12/1985 | Berg et al. |
| 4,560,979 A | 12/1985 | Rosskopf |
| 4,561,443 A | 12/1985 | Hogrefe et al. |
| 4,562,751 A | 1/1986 | Nason |
| 4,564,054 A | 1/1986 | Gustavsson |
| 4,590,473 A | 5/1986 | Burke et al. |
| 4,602,249 A | 7/1986 | Abbott |
| 4,619,653 A | 10/1986 | Fischell |
| 4,622,979 A | 11/1986 | Katchis et al. |
| 4,624,661 A | 11/1986 | Arimond |
| 4,636,950 A | 1/1987 | Caswell et al. |
| 4,637,817 A | 1/1987 | Archibald et al. |
| 4,650,469 A | 3/1987 | Berg et al. |
| 4,652,262 A | 3/1987 | Veracchi |
| 4,653,010 A | 3/1987 | Figler et al. |
| 4,676,776 A | 6/1987 | Howson |
| 4,681,563 A | 7/1987 | Deckert et al. |
| 4,688,167 A | 8/1987 | Agarwal |
| 4,691,580 A | 9/1987 | Fosslien |
| 4,695,954 A | 9/1987 | Rose et al. |
| 4,696,671 A | 9/1987 | Epstein et al. |
| 4,697,928 A | 10/1987 | Csongor |
| 4,702,595 A | 10/1987 | Mutschler et al. |
| 4,705,506 A | 11/1987 | Archibald |
| D293,135 S | 12/1987 | Medema et al. |
| 4,714,462 A | 12/1987 | DiComenico |
| 4,717,042 A | 1/1988 | McLaughlin |
| 4,718,576 A | 1/1988 | Tamura et al. |
| 4,722,224 A | 2/1988 | Scheller et al. |
| 4,722,349 A | 2/1988 | Baumberg |
| 4,722,734 A | 2/1988 | Kolln |
| 4,730,849 A | 3/1988 | Siegel |
| 4,731,058 A | 3/1988 | Doan |
| 4,732,411 A | 3/1988 | Siegel |
| 4,741,732 A | 5/1988 | Crankshaw et al. |
| 4,741,736 A | 5/1988 | Brown |
| 4,756,706 A | 7/1988 | Kerns et al. |
| 4,759,756 A | 7/1988 | Forman |
| 4,770,184 A | 9/1988 | Greene et al. |
| 4,778,449 A | 10/1988 | Weber et al. |
| 4,779,626 A | 10/1988 | Peel et al. |
| 4,784,645 A | 11/1988 | Fischell |
| 4,785,799 A | 11/1988 | Schoon et al. |
| 4,785,969 A | 11/1988 | McLaughlin |
| 4,796,644 A | 1/1989 | Polaschegg |
| 4,797,840 A | 1/1989 | Fraden |
| 4,803,625 A | 2/1989 | Fu et al. |
| 4,810,090 A | 3/1989 | Boucher |
| 4,810,243 A | 3/1989 | Howson |
| 4,811,844 A | 3/1989 | Moulding, Jr. et al. |
| 4,816,208 A | 3/1989 | Woods et al. |
| 4,817,044 A | 3/1989 | Ogren |
| 4,828,545 A | 5/1989 | Epstein et al. |
| 4,829,524 A | 5/1989 | Yoshida |
| 4,830,018 A | 5/1989 | Treach |
| 4,831,562 A | 5/1989 | Mcintosh et al. |
| 4,832,033 A | 5/1989 | Maher et al. |
| 4,835,372 A | 5/1989 | Gombrich et al. |
| 4,835,521 A | 5/1989 | Andrejasich et al. |
| 4,838,275 A | 6/1989 | Lee |
| 4,839,806 A | 6/1989 | Goldfischer et al. |
| 4,845,644 A | 7/1989 | Anthias et al. |
| 4,847,764 A | 7/1989 | Halvorson |
| 4,850,009 A | 7/1989 | Zook et al. |
| 4,850,972 A | 7/1989 | Schulman et al. |
| 4,853,521 A | 8/1989 | Claeys et al. |
| 4,854,324 A | 8/1989 | Hirschman et al. |
| 4,857,713 A | 8/1989 | Brown |
| 4,857,716 A | 8/1989 | Gombrich et al. |
| 4,865,584 A | 9/1989 | Epstein et al. |
| 4,871,351 A | 10/1989 | Feingold |
| 4,878,175 A | 10/1989 | Norden-Paul et al. |
| 4,880,013 A | 11/1989 | Chio |
| 4,889,132 A | 12/1989 | Hutcheson et al. |

(56) References Cited

U.S. PATENT DOCUMENTS

| | | |
|---|---|---|
| 4,889,134 A | 12/1989 | Greenwold et al. |
| 4,893,270 A | 1/1990 | Beck et al. |
| 4,897,777 A | 1/1990 | Janke et al. |
| 4,898,209 A | 2/1990 | Zbed |
| 4,898,576 A | 2/1990 | Philip |
| 4,898,578 A | 2/1990 | Rubalcaba, Jr. |
| 4,901,728 A | 2/1990 | Hutchison |
| 4,905,163 A | 2/1990 | Garber et al. |
| 4,908,017 A | 3/1990 | Howson et al. |
| 4,912,623 A | 3/1990 | Rantala et al. |
| 4,916,441 A | 4/1990 | Gombrich et al. |
| 4,922,922 A | 5/1990 | Pollock et al. |
| 4,925,444 A | 5/1990 | Orkin et al. |
| 4,933,843 A | 6/1990 | Scheller et al. |
| 4,937,777 A | 6/1990 | Flood et al. |
| 4,941,808 A | 7/1990 | Qureshi et al. |
| 4,943,279 A | 7/1990 | Samiotes et al. |
| 4,943,987 A | 7/1990 | Asahina et al. |
| 4,946,445 A | 8/1990 | Lynn |
| 4,949,274 A | 8/1990 | Hollander et al. |
| 4,952,928 A | 8/1990 | Carroll et al. |
| 4,953,074 A | 8/1990 | Kametani et al. |
| 4,960,230 A | 10/1990 | Marelli |
| 4,964,847 A | 10/1990 | Prince |
| 4,966,579 A | 10/1990 | Polaschegg |
| 4,967,928 A | 11/1990 | Carter |
| 4,968,295 A | 11/1990 | Neumann |
| 4,975,647 A | 12/1990 | Downer et al. |
| 4,977,590 A | 12/1990 | Milovancevic |
| 4,978,335 A | 12/1990 | Arthur, III |
| 4,991,091 A | 2/1991 | Allen |
| 4,992,926 A | 2/1991 | Janke et al. |
| 4,993,068 A | 2/1991 | Piosenka et al. |
| 4,993,506 A | 2/1991 | Angel |
| 4,998,249 A | 3/1991 | Bennett et al. |
| 5,002,055 A | 3/1991 | Merki et al. |
| 5,003,296 A | 3/1991 | Lee |
| 5,006,699 A | 4/1991 | Felkner et al. |
| 5,007,429 A | 4/1991 | Treatch et al. |
| 5,012,402 A | 4/1991 | Akiyama |
| 5,012,411 A | 4/1991 | Policastro et al. |
| 5,014,875 A | 5/1991 | McLaughlin et al. |
| 5,016,172 A | 5/1991 | Dessertine |
| 5,023,770 A | 6/1991 | Siverling |
| 5,025,374 A | 6/1991 | Roizen et al. |
| 5,036,852 A | 8/1991 | Leishman |
| 5,038,800 A | 8/1991 | Oba |
| 5,041,086 A | 8/1991 | Koenig et al. |
| 5,045,048 A | 9/1991 | Kaleskas et al. |
| 5,047,959 A | 9/1991 | Phillips et al. |
| 5,053,031 A | 10/1991 | Borsanyi |
| 5,053,990 A | 10/1991 | Kreifels et al. |
| 5,055,001 A | 10/1991 | Natwick et al. |
| 5,057,076 A | 10/1991 | Polaschegg |
| 5,061,243 A | 10/1991 | Winchell et al. |
| 5,072,356 A | 12/1991 | Watt et al. |
| 5,072,383 A | 12/1991 | Brimm et al. |
| 5,072,412 A | 12/1991 | Henderson, Jr. et al. |
| 5,078,683 A | 1/1992 | Sancoff et al. |
| 5,084,828 A | 1/1992 | Kaufman et al. |
| 5,087,245 A | 2/1992 | Doan |
| 5,088,904 A | 2/1992 | Okada |
| 5,088,981 A | 2/1992 | Howson et al. |
| 5,088,990 A | 2/1992 | Hivale et al. |
| 5,096,385 A | 3/1992 | Georgi et al. |
| 5,098,377 A | 3/1992 | Borsanyi et al. |
| 5,100,380 A | 3/1992 | Epstein et al. |
| 5,100,394 A | 3/1992 | Dudar et al. |
| 5,103,211 A | 4/1992 | Daoud et al. |
| 5,104,374 A | 4/1992 | Bishko et al. |
| 5,108,131 A | 4/1992 | Nassim |
| 5,108,363 A | 4/1992 | Tuttle et al. |
| 5,108,367 A | 4/1992 | Epstein et al. |
| 5,108,372 A | 4/1992 | Swenson |
| 5,109,487 A | 4/1992 | Ohgomori et al. |
| 5,109,849 A | 5/1992 | Goodman et al. |
| 5,112,319 A | 5/1992 | Lai |
| 5,116,203 A | 5/1992 | Natwick et al. |
| 5,116,312 A | 5/1992 | Blankenship et al. |
| 5,131,092 A | 7/1992 | Sackmann et al. |
| 5,134,574 A | 7/1992 | Beaverstock et al. |
| 5,135,500 A | 8/1992 | Zdeb |
| 5,137,023 A | 8/1992 | Mendelson et al. |
| 5,151,978 A | 9/1992 | Bronikowski et al. |
| 5,152,296 A | 10/1992 | Simons |
| 5,153,416 A | 10/1992 | Neeley |
| 5,153,827 A | 10/1992 | Coutre et al. |
| 5,155,693 A | 10/1992 | Altmayer et al. |
| 5,157,595 A | 10/1992 | Lovrenich |
| 5,158,091 A | 10/1992 | Butterfield et al. |
| 5,159,673 A | 10/1992 | Sackmann et al. |
| 5,160,320 A | 11/1992 | Yum et al. |
| 5,161,211 A | 11/1992 | Taguchi et al. |
| 5,167,235 A | 12/1992 | Seacord et al. |
| 5,169,642 A | 12/1992 | Brinker et al. |
| 5,172,698 A | 12/1992 | Stanko |
| 5,176,004 A | 1/1993 | Gaudet |
| 5,179,569 A | 1/1993 | Sawyer |
| 5,179,700 A | 1/1993 | Aihara et al. |
| 5,181,910 A | 1/1993 | Scanlon |
| 5,190,185 A | 3/1993 | Blechl |
| 5,190,522 A | 3/1993 | Wojcicki et al. |
| 5,191,891 A | 3/1993 | Righter |
| 5,208,762 A | 5/1993 | Charhut et al. |
| 5,208,907 A | 5/1993 | Shelton et al. |
| 5,211,849 A | 5/1993 | Kitaevich et al. |
| 5,213,099 A | 5/1993 | Tripp, Jr. |
| 5,213,232 A | 5/1993 | Kraft et al. |
| 5,213,568 A | 5/1993 | Lattin et al. |
| 5,219,330 A | 6/1993 | Bollish et al. |
| 5,219,331 A | 6/1993 | Vanderveen |
| 5,225,974 A | 7/1993 | Mathews et al. |
| 5,226,425 A | 7/1993 | Righter |
| 5,228,450 A | 7/1993 | Sellers |
| 5,231,990 A | 8/1993 | Gauglitz |
| 5,234,404 A | 8/1993 | Tuttle et al. |
| 5,235,510 A | 8/1993 | Yamada et al. |
| 5,236,416 A | 8/1993 | McDaniel et al. |
| 5,238,001 A | 8/1993 | Gallant et al. |
| 5,240,007 A | 8/1993 | Pytel et al. |
| 5,244,463 A | 9/1993 | Cordner, Jr. et al. |
| 5,245,704 A | 9/1993 | Weber et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,884 A | 11/1993 | Stern et al. |
| 5,262,943 A | 11/1993 | Thibado et al. |
| 5,265,010 A | 11/1993 | Evans-Paganelli et al. |
| 5,265,431 A | 11/1993 | Gaudet et al. |
| 5,267,174 A | 11/1993 | Kaufman et al. |
| 5,271,405 A | 12/1993 | Boyer et al. |
| 5,272,318 A | 12/1993 | Gorman |
| 5,272,321 A | 12/1993 | Otsuka et al. |
| 5,273,517 A | 12/1993 | Barone et al. |
| 5,277,188 A | 1/1994 | Selker |
| 5,283,861 A | 2/1994 | Dangler et al. |
| 5,284,150 A | 2/1994 | Butterfield et al. |
| 5,286,252 A | 2/1994 | Tuttle et al. |
| 5,292,029 A | 3/1994 | Pearson |
| 5,297,257 A | 3/1994 | Struger et al. |
| 5,298,021 A | 3/1994 | Sherer |
| 5,304,126 A | 4/1994 | Epstein et al. |
| 5,307,263 A | 4/1994 | Brown |
| 5,307,372 A | 4/1994 | Sawyer et al. |
| 5,307,463 A | 4/1994 | Hyatt et al. |
| 5,311,908 A | 5/1994 | Barone et al. |
| 5,314,243 A | 5/1994 | McDonald et al. |
| 5,315,505 A | 5/1994 | Pratt et al. |
| 5,317,506 A | 5/1994 | Coutre et al. |
| 5,319,363 A | 6/1994 | Welch et al. |
| 5,319,543 A | 6/1994 | Wilhelm |
| 5,321,618 A | 6/1994 | Gessman |
| 5,321,829 A | 6/1994 | Zifferer |
| 5,324,422 A | 6/1994 | Colleran et al. |

(56) References Cited

U.S. PATENT DOCUMENTS

| | | |
|---|---|---|
| 5,325,478 A | 6/1994 | Shelton et al. |
| 5,327,341 A | 7/1994 | Whalen et al. |
| 5,331,549 A | 7/1994 | Crawford, Jr. |
| 5,336,245 A | 8/1994 | Adams et al. |
| 5,337,230 A | 8/1994 | Baumgartner et al. |
| 5,337,747 A | 8/1994 | Neftel |
| 5,337,919 A | 8/1994 | Spaulding et al. |
| 5,338,157 A | 8/1994 | Blomquist |
| 5,339,421 A | 8/1994 | Housel, III |
| 5,339,821 A | 8/1994 | Fujimoto |
| 5,341,291 A | 8/1994 | Roizen et al. |
| 5,341,412 A | 8/1994 | Ramot et al. |
| 5,348,008 A | 9/1994 | Bornn et al. |
| 5,348,539 A | 9/1994 | Herskowitz |
| 5,349,675 A | 9/1994 | Fitzgerald et al. |
| 5,356,378 A | 10/1994 | Doan |
| 5,360,410 A | 11/1994 | Wacks |
| 5,361,202 A | 11/1994 | Doue |
| 5,361,758 A | 11/1994 | Hall et al. |
| 5,366,896 A | 11/1994 | Margrey et al. |
| 5,366,904 A | 11/1994 | Qureshi et al. |
| 5,367,555 A | 11/1994 | Isoyama |
| 5,368,562 A | 11/1994 | Blomquist et al. |
| 5,370,612 A | 12/1994 | Maeda et al. |
| 5,371,687 A | 12/1994 | Holmes, II et al. |
| 5,374,251 A | 12/1994 | Smith |
| 5,374,813 A | 12/1994 | Shipp |
| 5,374,965 A | 12/1994 | Kanno |
| 5,375,604 A | 12/1994 | Kelly et al. |
| 5,376,070 A | 12/1994 | Purvis et al. |
| 5,377,864 A | 1/1995 | Blechl et al. |
| 5,378,231 A | 1/1995 | Johnson et al. |
| 5,379,214 A | 1/1995 | Arbuckle et al. |
| 5,389,078 A | 2/1995 | Zalesky et al. |
| 5,390,238 A | 2/1995 | Kirk et al. |
| 5,392,951 A | 2/1995 | Gardner et al. |
| 5,395,320 A | 3/1995 | Padda et al. |
| 5,395,321 A | 3/1995 | Kawahara et al. |
| 5,398,336 A | 3/1995 | Tantry et al. |
| 5,401,059 A | 3/1995 | Ferrario |
| 5,404,292 A | 4/1995 | Hendrickson |
| 5,404,384 A | 4/1995 | Colburn et al. |
| 5,406,473 A | 4/1995 | Yoshikura et al. |
| 5,412,715 A | 5/1995 | Volpe |
| 5,415,167 A | 5/1995 | Wilk |
| 5,416,695 A | 5/1995 | Stutman et al. |
| 5,417,222 A | 5/1995 | Dempsey et al. |
| 5,420,977 A | 5/1995 | Sztipanovits et al. |
| 5,421,343 A | 6/1995 | Feng |
| 5,423,746 A | 6/1995 | Burkett et al. |
| 5,429,602 A | 7/1995 | Hauser |
| 5,431,201 A | 7/1995 | Torchia et al. |
| 5,431,299 A | 7/1995 | Brewer et al. |
| 5,431,627 A | 7/1995 | Pastrone et al. |
| 5,433,736 A | 7/1995 | Nilsson |
| 5,438,607 A | 8/1995 | Przygoda, Jr. et al. |
| 5,440,699 A | 8/1995 | Farrand et al. |
| 5,441,047 A | 8/1995 | David et al. |
| 5,445,294 A | 8/1995 | Gardner et al. |
| 5,445,621 A | 8/1995 | Poli et al. |
| 5,446,868 A | 8/1995 | Gardea, II et al. |
| 5,453,098 A | 9/1995 | Botts et al. |
| 5,455,851 A | 10/1995 | Chaco et al. |
| 5,458,123 A | 10/1995 | Unger |
| 5,460,294 A | 10/1995 | Williams |
| 5,460,605 A | 10/1995 | Tuttle et al. |
| 5,461,665 A | 10/1995 | Shur et al. |
| 5,462,051 A | 10/1995 | Oka et al. |
| 5,464,392 A | 11/1995 | Epstein et al. |
| 5,465,286 A | 11/1995 | Clare et al. |
| 5,467,773 A | 11/1995 | Bergelson et al. |
| 5,468,110 A | 11/1995 | McDonald et al. |
| 5,469,855 A | 11/1995 | Pompei et al. |
| 5,471,382 A | 11/1995 | Tallman et al. |
| 5,474,552 A | 12/1995 | Palti |
| 5,482,043 A | 1/1996 | Zulauf |
| 5,482,446 A | 1/1996 | Williamson et al. |
| 5,485,408 A | 1/1996 | Blomquist |
| 5,490,610 A | 2/1996 | Pearson |
| 5,494,592 A | 2/1996 | Latham, Jr. et al. |
| 5,496,265 A | 3/1996 | Langley et al. |
| 5,496,273 A | 3/1996 | Pastrone et al. |
| 5,502,944 A | 4/1996 | Kraft et al. |
| 5,507,412 A | 4/1996 | Ebert et al. |
| 5,508,912 A | 4/1996 | Schneiderman |
| 5,509,318 A | 4/1996 | Gomes |
| 5,509,422 A | 4/1996 | Fukami |
| 5,513,957 A | 5/1996 | O'Leary |
| 5,514,088 A | 5/1996 | Zakko |
| 5,514,095 A | 5/1996 | Brightbill et al. |
| 5,515,426 A | 5/1996 | Yacenda et al. |
| 5,520,450 A | 5/1996 | Colson, Jr. et al. |
| 5,520,637 A | 5/1996 | Pager et al. |
| 5,522,396 A | 6/1996 | Langer et al. |
| 5,522,798 A | 6/1996 | Johnson et al. |
| 5,526,428 A | 6/1996 | Arnold |
| 5,528,503 A | 6/1996 | Moore et al. |
| 5,529,063 A | 6/1996 | Hill |
| 5,531,680 A | 7/1996 | Dumas et al. |
| 5,531,697 A | 7/1996 | Olsen et al. |
| 5,531,698 A | 7/1996 | Olsen |
| 5,533,079 A | 7/1996 | Colburn et al. |
| 5,533,981 A | 7/1996 | Mandro et al. |
| 5,534,691 A | 7/1996 | Holdaway et al. |
| 5,536,084 A | 7/1996 | Curtis et al. |
| 5,537,313 A | 7/1996 | Pirelli |
| 5,537,853 A | 7/1996 | Finburgh et al. |
| 5,542,420 A | 8/1996 | Goldman et al. |
| 5,544,649 A | 8/1996 | David et al. |
| 5,544,651 A | 8/1996 | Wilk |
| 5,544,661 A | 8/1996 | Davis et al. |
| 5,545,140 A | 8/1996 | Conero et al. |
| 5,546,580 A | 8/1996 | Seliger et al. |
| 5,547,470 A | 8/1996 | Johnson et al. |
| 5,549,117 A | 8/1996 | Tacklind et al. |
| 5,549,460 A | 8/1996 | O'Leary |
| 5,553,609 A | 9/1996 | Chen et al. |
| 5,558,638 A | 9/1996 | Evers et al. |
| 5,558,640 A | 9/1996 | Pfeiler et al. |
| 5,560,352 A | 10/1996 | Heim et al. |
| 5,562,232 A | 10/1996 | Pearson |
| 5,562,621 A | 10/1996 | Claude et al. |
| 5,563,347 A | 10/1996 | Martin et al. |
| 5,564,434 A | 10/1996 | Halperin et al. |
| 5,564,803 A | 10/1996 | McDonald et al. |
| 5,568,912 A | 10/1996 | Minami et al. |
| 5,569,186 A | 10/1996 | Lord et al. |
| 5,569,187 A | 10/1996 | Kaiser |
| 5,571,258 A | 11/1996 | Pearson |
| 5,573,502 A | 11/1996 | LeCocq et al. |
| 5,573,506 A | 11/1996 | Vasko |
| 5,575,632 A | 11/1996 | Morris et al. |
| 5,576,952 A | 11/1996 | Stutman et al. |
| 5,579,001 A | 11/1996 | Dempsey et al. |
| 5,579,378 A | 11/1996 | Arlinghaus, Jr. |
| 5,581,369 A | 12/1996 | Righter et al. |
| 5,581,687 A | 12/1996 | Lyle et al. |
| 5,582,593 A | 12/1996 | Hultman |
| 5,583,758 A | 12/1996 | Mcilroy et al. |
| 5,588,815 A | 12/1996 | Zaleski, II |
| 5,589,932 A | 12/1996 | Garcia-Rubio et al. |
| 5,590,648 A | 1/1997 | Mitchell et al. |
| 5,591,344 A | 1/1997 | Kenley et al. |
| 5,593,267 A | 1/1997 | McDonald et al. |
| 5,594,637 A | 1/1997 | Eisenberg et al. |
| 5,594,786 A | 1/1997 | Chaco et al. |
| 5,597,995 A | 1/1997 | Williams et al. |
| 5,598,536 A | 1/1997 | Slaughter, III et al. |
| 5,601,445 A | 2/1997 | Schipper et al. |
| 5,609,575 A | 3/1997 | Larson et al. |
| 5,609,576 A | 3/1997 | Voss et al. |
| 5,613,115 A | 3/1997 | Gihl et al. |
| 5,619,428 A | 4/1997 | Lee et al. |
| 5,619,991 A | 4/1997 | Sloane |

(56) References Cited

U.S. PATENT DOCUMENTS

| | | |
|---|---|---|
| 5,623,652 A | 4/1997 | Vora et al. |
| 5,623,925 A | 4/1997 | Swenson et al. |
| 5,626,144 A | 5/1997 | Tacklind et al. |
| 5,628,619 A | 5/1997 | Wilson |
| 5,630,710 A | 5/1997 | Tune et al. |
| 5,631,844 A | 5/1997 | Margrey et al. |
| 5,633,910 A | 5/1997 | Cohen |
| D380,260 S | 6/1997 | Hyman |
| 5,634,893 A | 6/1997 | Rishton |
| 5,637,082 A | 6/1997 | Pages et al. |
| 5,637,093 A | 6/1997 | Hyman et al. |
| 5,640,301 A | 6/1997 | Roecher et al. |
| 5,640,953 A | 6/1997 | Bishop et al. |
| 5,641,628 A | 6/1997 | Bianchi |
| 5,643,193 A | 7/1997 | Papillon et al. |
| 5,643,212 A | 7/1997 | Coutre et al. |
| 5,647,853 A | 7/1997 | Feldmann et al. |
| 5,647,854 A | 7/1997 | Olsen et al. |
| 5,651,775 A | 7/1997 | Walker et al. |
| 5,652,566 A | 7/1997 | Lambert |
| 5,658,240 A | 8/1997 | Urdahl et al. |
| 5,658,250 A | 8/1997 | Blomquist et al. |
| 5,661,978 A | 9/1997 | Holmes et al. |
| 5,664,270 A | 9/1997 | Bell et al. |
| 5,666,404 A | 9/1997 | Ciccotelli et al. |
| D385,646 S | 10/1997 | Chan |
| 5,678,562 A | 10/1997 | Sellers |
| 5,678,568 A | 10/1997 | Uchikubo et al. |
| 5,681,285 A | 10/1997 | Ford et al. |
| 5,682,526 A | 10/1997 | Smokoff et al. |
| 5,683,367 A | 11/1997 | Jordan et al. |
| 5,685,844 A | 11/1997 | Marttila |
| 5,687,717 A | 11/1997 | Halpern |
| 5,687,734 A | 11/1997 | Dempsey et al. |
| 5,695,473 A | 12/1997 | Olsen |
| 5,697,951 A | 12/1997 | Harpstead |
| 5,700,998 A | 12/1997 | Palti |
| 5,701,894 A | 12/1997 | Cherry et al. |
| 5,704,351 A | 1/1998 | Mortara et al. |
| 5,704,364 A | 1/1998 | Saltzstein et al. |
| 5,704,366 A | 1/1998 | Tacklind et al. |
| 5,712,798 A | 1/1998 | Langley et al. |
| 5,712,912 A | 1/1998 | Tomko et al. |
| 5,713,485 A | 2/1998 | Liff et al. |
| 5,713,856 A | 2/1998 | Eggers et al. |
| 5,715,823 A | 2/1998 | Wood et al. |
| 5,716,114 A | 2/1998 | Holmes et al. |
| 5,716,194 A | 2/1998 | Butterfield et al. |
| 5,718,562 A | 2/1998 | Lawless et al. |
| 5,719,761 A | 2/1998 | Gatti et al. |
| RE35,743 E | 3/1998 | Pearson |
| 5,724,025 A | 3/1998 | Tavori |
| 5,724,580 A | 3/1998 | Levin et al. |
| 5,732,709 A | 3/1998 | Tacklind et al. |
| 5,733,259 A | 3/1998 | Valcke et al. |
| 5,735,887 A | 4/1998 | Barreras, Sr. et al. |
| 5,737,539 A | 4/1998 | Edelson et al. |
| 5,740,185 A | 4/1998 | Bosse |
| 5,740,800 A | 4/1998 | Hendrickson et al. |
| 5,745,366 A | 4/1998 | Higham et al. |
| 5,745,378 A | 4/1998 | Barker et al. |
| 5,752,917 A | 5/1998 | Fuchs |
| 5,752,976 A | 5/1998 | Duffin et al. |
| 5,755,563 A | 5/1998 | Clegg et al. |
| 5,758,095 A | 5/1998 | Albaum et al. |
| 5,764,923 A | 6/1998 | Tallman et al. |
| 5,766,155 A | 6/1998 | Hyman et al. |
| 5,769,811 A | 6/1998 | Stacey et al. |
| 5,771,657 A | 6/1998 | Lasher et al. |
| 5,772,585 A | 6/1998 | Lavin et al. |
| 5,772,586 A | 6/1998 | Heinonen et al. |
| 5,772,635 A | 6/1998 | Dastur et al. |
| 5,772,637 A | 6/1998 | Heinzmann et al. |
| 5,776,057 A | 7/1998 | Swenson et al. |
| 5,778,345 A | 7/1998 | McCartney |
| 5,778,882 A | 7/1998 | Raymond et al. |
| 5,781,442 A | 7/1998 | Engleson et al. |
| 5,782,805 A | 7/1998 | Meinzer et al. |
| 5,782,878 A | 7/1998 | Morgan et al. |
| 5,785,650 A | 7/1998 | Akasaka et al. |
| 5,788,669 A | 8/1998 | Peterson |
| 5,788,851 A | 8/1998 | Kenley et al. |
| 5,790,409 A | 8/1998 | Fedor et al. |
| 5,791,342 A | 8/1998 | Woodard |
| 5,791,880 A | 8/1998 | Wilson |
| 5,793,861 A | 8/1998 | Haigh |
| 5,793,969 A | 8/1998 | Kamentsky et al. |
| 5,795,317 A | 8/1998 | Brierton et al. |
| 5,795,327 A | 8/1998 | Wilson et al. |
| 5,797,515 A | 8/1998 | Liff et al. |
| 5,800,387 A | 9/1998 | Duffy et al. |
| 5,801,755 A | 9/1998 | Echerer |
| 5,803,906 A | 9/1998 | Pratt et al. |
| 5,805,442 A | 9/1998 | Crater et al. |
| 5,805,454 A | 9/1998 | Valerino et al. |
| 5,805,456 A | 9/1998 | Higham et al. |
| 5,805,505 A | 9/1998 | Zheng et al. |
| 5,807,321 A | 9/1998 | Stoker et al. |
| 5,807,322 A | 9/1998 | Lindsey et al. |
| 5,807,336 A | 9/1998 | Russo et al. |
| 5,810,747 A | 9/1998 | Brudny et al. |
| 5,812,410 A | 9/1998 | Lion et al. |
| 5,814,015 A | 9/1998 | Gargano et al. |
| 5,815,566 A | 9/1998 | Ramot et al. |
| 5,818,528 A | 10/1998 | Roth et al. |
| 5,822,418 A | 10/1998 | Yacenda et al. |
| 5,822,544 A | 10/1998 | Chaco et al. |
| 5,823,949 A | 10/1998 | Goltra |
| 5,826,237 A | 10/1998 | Macrae et al. |
| 5,829,438 A | 11/1998 | Gibbs et al. |
| 5,832,447 A | 11/1998 | Rieker et al. |
| 5,832,448 A | 11/1998 | Brown |
| 5,832,450 A | 11/1998 | Myers et al. |
| 5,833,599 A | 11/1998 | Schrier et al. |
| 5,835,897 A | 11/1998 | Dang |
| 5,836,910 A | 11/1998 | Duffy et al. |
| 5,841,975 A | 11/1998 | Layne et al. |
| 5,842,841 A | 12/1998 | Danby et al. |
| 5,842,976 A | 12/1998 | Williamson |
| 5,845,253 A | 12/1998 | Rensimer et al. |
| 5,848,593 A | 12/1998 | McGrady et al. |
| 5,851,186 A | 12/1998 | Wood et al. |
| 5,852,590 A | 12/1998 | De La Huerga |
| 5,853,387 A | 12/1998 | Clegg et al. |
| 5,855,550 A | 1/1999 | Lai et al. |
| 5,857,967 A | 1/1999 | Frid et al. |
| 5,859,972 A | 1/1999 | Subramaniam et al. |
| 5,865,745 A | 2/1999 | Schmitt et al. |
| 5,865,786 A | 2/1999 | Sibalis et al. |
| 5,867,821 A | 2/1999 | Ballantyne et al. |
| 5,871,465 A | 2/1999 | Vasko |
| 5,876,926 A | 3/1999 | Beecham |
| 5,880,443 A | 3/1999 | McDonald et al. |
| 5,882,338 A | 3/1999 | Gray |
| 5,883,370 A | 3/1999 | Walker et al. |
| 5,883,576 A | 3/1999 | De La Huerga |
| 5,884,273 A | 3/1999 | Sattizahn et al. |
| 5,884,457 A | 3/1999 | Ortiz et al. |
| 5,885,245 A | 3/1999 | Lynch et al. |
| 5,891,035 A | 4/1999 | Wood et al. |
| 5,891,734 A | 4/1999 | Gill et al. |
| 5,893,697 A | 4/1999 | Zini et al. |
| 5,894,273 A | 4/1999 | Meador et al. |
| 5,895,371 A | 4/1999 | Levitas et al. |
| 5,897,493 A | 4/1999 | Brown |
| 5,897,530 A | 4/1999 | Jackson |
| 5,897,989 A | 4/1999 | Beecham |
| 5,899,665 A | 5/1999 | Makino et al. |
| 5,899,855 A | 5/1999 | Brown |
| 5,901,150 A | 5/1999 | Jhuboo et al. |
| 5,904,668 A | 5/1999 | Hyman et al. |
| 5,905,653 A | 5/1999 | Higham et al. |
| 5,907,291 A | 5/1999 | Chen et al. |
| 5,907,493 A | 5/1999 | Boyer et al. |

(56) References Cited

U.S. PATENT DOCUMENTS

| | | |
|---|---|---|
| 5,908,027 A | 6/1999 | Butterfield et al. |
| 5,910,107 A | 6/1999 | Iliff |
| 5,910,252 A | 6/1999 | Truitt et al. |
| 5,911,132 A | 6/1999 | Sloane |
| 5,911,687 A | 6/1999 | Sato et al. |
| 5,912,818 A | 6/1999 | McGrady et al. |
| 5,913,197 A | 6/1999 | Kameda |
| 5,913,310 A | 6/1999 | Brown |
| 5,915,089 A | 6/1999 | Stevens et al. |
| 5,915,240 A | 6/1999 | Karpf |
| 5,919,154 A | 7/1999 | Toavs et al. |
| 5,921,938 A | 7/1999 | Aoyama et al. |
| 5,923,018 A | 7/1999 | Kameda et al. |
| 5,924,074 A | 7/1999 | Evans |
| 5,924,103 A | 7/1999 | Ahmed et al. |
| 5,927,540 A | 7/1999 | Godlewski |
| 5,931,791 A | 8/1999 | Saltzstein et al. |
| 5,935,060 A | 8/1999 | Iliff |
| 5,935,099 A | 8/1999 | Peterson et al. |
| 5,935,106 A | 8/1999 | Olsen |
| 5,938,413 A | 8/1999 | Makino et al. |
| 5,939,326 A | 8/1999 | Chupp et al. |
| 5,939,699 A | 8/1999 | Perttunen et al. |
| 5,940,306 A | 8/1999 | Gardner et al. |
| 5,940,802 A | 8/1999 | Hildebrand et al. |
| 5,941,829 A | 8/1999 | Saltzstein et al. |
| 5,941,846 A | 8/1999 | Duffy et al. |
| 5,942,986 A | 8/1999 | Shabot et al. |
| 5,943,423 A | 8/1999 | Muftic |
| 5,943,633 A | 8/1999 | Wilson et al. |
| 5,944,659 A | 8/1999 | Flach et al. |
| 5,945,651 A | 8/1999 | Chorosinski et al. |
| 5,946,083 A | 8/1999 | Melendez et al. |
| 5,946,659 A | 8/1999 | Lancelot et al. |
| D414,578 S | 9/1999 | Chen et al. |
| 5,950,006 A | 9/1999 | Crater et al. |
| 5,951,300 A | 9/1999 | Brown |
| 5,951,510 A | 9/1999 | Barak |
| 5,954,640 A | 9/1999 | Szabo |
| 5,954,885 A | 9/1999 | Bollish et al. |
| 5,954,971 A | 9/1999 | Pages et al. |
| 5,956,023 A | 9/1999 | Lyle et al. |
| 5,957,885 A | 9/1999 | Bollish et al. |
| 5,959,529 A | 9/1999 | Kail, IV |
| 5,960,085 A | 9/1999 | de la Huerga |
| 5,960,403 A | 9/1999 | Brown |
| 5,960,991 A | 10/1999 | Ophardt |
| 5,961,446 A | 10/1999 | Beller et al. |
| 5,961,448 A | 10/1999 | Swenson et al. |
| 5,961,487 A | 10/1999 | Davis |
| 5,961,923 A | 10/1999 | Nova et al. |
| 5,963,641 A | 10/1999 | Crandall et al. |
| 5,964,700 A | 10/1999 | Tallman et al. |
| 5,966,304 A | 10/1999 | Cook et al. |
| 5,967,975 A | 10/1999 | Ridgeway |
| 5,970,423 A | 10/1999 | Langley et al. |
| 5,971,593 A | 10/1999 | McGrady |
| 5,971,921 A | 10/1999 | Timbel |
| 5,971,948 A | 10/1999 | Pages et al. |
| 5,974,124 A | 10/1999 | Schlueter, Jr. et al. |
| 5,975,737 A | 11/1999 | Crater et al. |
| 5,980,490 A | 11/1999 | Tsoukalis |
| 5,983,193 A | 11/1999 | Heinonen et al. |
| 5,987,519 A | 11/1999 | Peifer et al. |
| 5,991,731 A | 11/1999 | Colon et al. |
| 5,993,046 A | 11/1999 | McGrady et al. |
| 5,993,420 A | 11/1999 | Hyman et al. |
| 5,995,077 A | 11/1999 | Wilcox et al. |
| 5,995,939 A | 11/1999 | Berman et al. |
| 5,995,965 A | 11/1999 | Experton |
| 5,997,167 A | 12/1999 | Crater et al. |
| 5,997,476 A | 12/1999 | Brown |
| 6,003,006 A | 12/1999 | Colella et al. |
| 6,004,020 A | 12/1999 | Bartur |
| 6,004,276 A | 12/1999 | Wright et al. |
| 6,006,191 A | 12/1999 | DeRienzo |
| 6,006,946 A | 12/1999 | Williams et al. |
| 6,009,333 A | 12/1999 | Chaco |
| 6,010,454 A | 1/2000 | Arieff et al. |
| 6,011,858 A | 1/2000 | Stock et al. |
| 6,011,999 A | 1/2000 | Holmes |
| 6,012,034 A | 1/2000 | Hamparian et al. |
| 6,013,057 A | 1/2000 | Danby et al. |
| 6,014,631 A | 1/2000 | Teagarden et al. |
| 6,016,444 A | 1/2000 | John |
| 6,017,318 A | 1/2000 | Gauthier et al. |
| 6,018,713 A | 1/2000 | Coli et al. |
| 6,019,745 A | 2/2000 | Gray |
| 6,021,392 A | 2/2000 | Lester et al. |
| 6,022,315 A | 2/2000 | Iliff |
| 6,023,522 A | 2/2000 | Draganoff et al. |
| 6,024,539 A | 2/2000 | Blomquist |
| 6,024,699 A | 2/2000 | Surwit et al. |
| 6,027,217 A | 2/2000 | McClure et al. |
| 6,029,138 A | 2/2000 | Khorasani et al. |
| 6,032,119 A | 2/2000 | Brown et al. |
| 6,032,155 A | 2/2000 | de la Huerga |
| 6,033,076 A | 3/2000 | Braeuning et al. |
| 6,039,251 A | 3/2000 | Holowko et al. |
| 6,039,467 A | 3/2000 | Holmes |
| 6,047,259 A | 4/2000 | Campbell et al. |
| 6,048,086 A | 4/2000 | Valerino |
| 6,050,940 A | 4/2000 | Braun et al. |
| 6,055,487 A | 4/2000 | Margery et al. |
| 6,057,758 A | 5/2000 | Dempsey et al. |
| 6,059,736 A | 5/2000 | Tapper |
| 6,061,603 A | 5/2000 | Papadopoulos et al. |
| 6,065,819 A | 5/2000 | Holmes et al. |
| 6,068,153 A | 5/2000 | Young et al. |
| 6,068,156 A | 5/2000 | Liff et al. |
| 6,073,046 A | 6/2000 | Patel et al. |
| 6,074,345 A | 6/2000 | van Oostrom et al. |
| 6,079,621 A | 6/2000 | Vardanyan et al. |
| 6,080,106 A | 6/2000 | Lloyd et al. |
| 6,081,048 A | 6/2000 | Bergmann et al. |
| 6,081,786 A | 6/2000 | Barry et al. |
| 6,082,776 A | 7/2000 | Feinberg |
| 6,083,206 A | 7/2000 | Molko |
| 6,093,146 A | 7/2000 | Filangeri |
| 6,095,985 A | 8/2000 | Raymond et al. |
| 6,096,561 A | 8/2000 | Tayi |
| 6,098,892 A | 8/2000 | Peoples, Jr. |
| 6,101,407 A | 8/2000 | Groezinger |
| 6,101,478 A | 8/2000 | Brown |
| 6,102,856 A | 8/2000 | Groff et al. |
| 6,108,399 A | 8/2000 | Hernandez-Guerra et al. |
| 6,108,588 A | 8/2000 | McGrady |
| 6,109,774 A | 8/2000 | Holmes et al. |
| 6,112,224 A | 8/2000 | Peifer et al. |
| RE36,871 E | 9/2000 | Epstein et al. |
| 6,113,554 A | 9/2000 | Gilcher et al. |
| 6,116,461 A | 9/2000 | Broadfield et al. |
| 6,117,940 A | 9/2000 | Mjalli |
| 6,123,524 A | 9/2000 | Danby et al. |
| 6,125,350 A | 9/2000 | Dirbas |
| 6,129,517 A | 10/2000 | Danby et al. |
| 6,132,371 A | 10/2000 | Dempsey et al. |
| 6,134,504 A | 10/2000 | Douglas et al. |
| 6,135,949 A | 10/2000 | Russo et al. |
| 6,139,177 A | 10/2000 | Venkatraman et al. |
| 6,139,495 A | 10/2000 | De La Huerga |
| 6,141,412 A | 10/2000 | Smith et al. |
| 6,144,922 A | 11/2000 | Douglas et al. |
| 6,145,695 A | 11/2000 | Garrigues |
| 6,146,523 A | 11/2000 | Kenley et al. |
| 6,148,297 A | 11/2000 | Swor et al. |
| 6,149,063 A | 11/2000 | Reynolds et al. |
| 6,151,536 A | 11/2000 | Arnold et al. |
| 6,152,364 A | 11/2000 | Schoonen et al. |
| 6,154,668 A | 11/2000 | Pedersen et al. |
| 6,154,726 A | 11/2000 | Rensimer et al. |
| 6,157,914 A | 12/2000 | Seto et al. |
| 6,158,965 A | 12/2000 | Butterfield et al. |
| 6,160,478 A | 12/2000 | Jacobsen et al. |

(56) References Cited

U.S. PATENT DOCUMENTS

| | | |
|---|---|---|
| 6,161,095 A | 12/2000 | Brown |
| 6,161,141 A | 12/2000 | Dillon |
| 6,163,737 A | 12/2000 | Fedor et al. |
| 6,165,154 A | 12/2000 | Gray et al. |
| 6,168,563 B1 | 1/2001 | Brown |
| 6,170,007 B1 | 1/2001 | Venkatraman et al. |
| 6,170,746 B1 | 1/2001 | Brook et al. |
| 6,171,112 B1 | 1/2001 | Clark et al. |
| 6,171,237 B1 | 1/2001 | Avitall et al. |
| 6,171,264 B1 | 1/2001 | Bader |
| 6,173,198 B1 | 1/2001 | Schulze et al. |
| 6,175,779 B1 | 1/2001 | Barrett |
| 6,175,977 B1 | 1/2001 | Schumacher et al. |
| 6,176,392 B1 | 1/2001 | William et al. |
| 6,182,047 B1 | 1/2001 | Dirbas |
| 6,183,417 B1 | 2/2001 | Geheb et al. |
| 6,186,145 B1 | 2/2001 | Brown |
| 6,192,320 B1 | 2/2001 | Margrey et al. |
| 6,193,480 B1 | 2/2001 | Butterfield |
| 6,195,887 B1 | 3/2001 | Danby et al. |
| 6,198,394 B1 | 3/2001 | Jacobsen et al. |
| 6,200,264 B1 | 3/2001 | Satherley et al. |
| 6,200,289 B1 | 3/2001 | Hochman et al. |
| 6,202,923 B1 | 3/2001 | Boyer et al. |
| 6,203,495 B1 | 3/2001 | Bardy |
| 6,203,528 B1 | 3/2001 | Deckert et al. |
| 6,206,238 B1 | 3/2001 | Ophardt |
| 6,206,829 B1 | 3/2001 | Iliff |
| 6,210,361 B1 | 4/2001 | Kamen et al. |
| 6,213,391 B1 | 4/2001 | Lewis |
| 6,213,738 B1 | 4/2001 | Danby et al. |
| 6,213,972 B1 | 4/2001 | Butterfield et al. |
| 6,219,439 B1 | 4/2001 | Burger |
| 6,219,587 B1 | 4/2001 | Ahlin et al. |
| 6,221,009 B1 | 4/2001 | Doi et al. |
| 6,221,011 B1 | 4/2001 | Bardy |
| 6,221,012 B1 | 4/2001 | Maschke et al. |
| 6,222,619 B1 | 4/2001 | Herron et al. |
| 6,224,549 B1 | 5/2001 | Drongelen |
| 6,225,901 B1 | 5/2001 | Kail, IV |
| 6,226,564 B1 | 5/2001 | Stuart |
| 6,226,745 B1 | 5/2001 | Wiederhold |
| 6,230,142 B1 | 5/2001 | Benigno et al. |
| 6,230,927 B1 | 5/2001 | Schoonen et al. |
| 6,234,997 B1 | 5/2001 | Kamen et al. |
| 6,245,013 B1 | 6/2001 | Minoz et al. |
| 6,246,473 B1 | 6/2001 | Smith, Jr. et al. |
| 6,248,063 B1 | 6/2001 | Barnhill et al. |
| 6,248,065 B1 | 6/2001 | Brown |
| 6,255,951 B1 | 7/2001 | De La Huerga |
| 6,256,643 B1 | 7/2001 | Cork et al. |
| 6,256,967 B1 | 7/2001 | Hebron et al. |
| 6,259,355 B1 | 7/2001 | Chaco et al. |
| 6,259,654 B1 | 7/2001 | De La Huerga |
| 6,260,021 B1 | 7/2001 | Wong et al. |
| 6,266,645 B1 | 7/2001 | Simpson |
| 6,269,340 B1 | 7/2001 | Ford et al. |
| D446,854 S | 8/2001 | Cheney, II et al. |
| 6,270,455 B1 | 8/2001 | Brown |
| 6,270,457 B1 | 8/2001 | Bardy |
| 6,272,394 B1 | 8/2001 | Lipps |
| 6,272,505 B1 | 8/2001 | De La Huerga |
| 6,277,072 B1 | 8/2001 | Bardy |
| 6,278,999 B1 | 8/2001 | Knapp |
| 6,283,322 B1 | 9/2001 | Liff et al. |
| 6,283,944 B1 | 9/2001 | McMullen et al. |
| 6,290,646 B1 | 9/2001 | Cosentino et al. |
| 6,290,650 B1 | 9/2001 | Butterfield et al. |
| 6,294,999 B1 | 9/2001 | Yarin et al. |
| 6,295,506 B1 | 9/2001 | Heinonen |
| 6,304,788 B1 | 10/2001 | Eady et al. |
| 6,306,088 B1 | 10/2001 | Krausman et al. |
| 6,307,956 B1 | 10/2001 | Black |
| 6,308,171 B1 | 10/2001 | De La Huerga |
| 6,311,163 B1 | 10/2001 | Sheehan et al. |
| 6,312,227 B1 | 11/2001 | Davis |
| 6,312,378 B1 | 11/2001 | Bardy |
| 6,314,384 B1 | 11/2001 | Goetz |
| 6,317,719 B1 | 11/2001 | Schrier et al. |
| 6,319,200 B1 | 11/2001 | Lai et al. |
| 6,321,203 B1 | 11/2001 | Kameda |
| 6,322,502 B1 | 11/2001 | Schoenberg et al. |
| 6,322,504 B1 | 11/2001 | Kirshner |
| 6,322,515 B1 | 11/2001 | Goor et al. |
| 6,330,491 B1 | 12/2001 | Lion |
| 6,332,090 B1 | 12/2001 | DeFrank et al. |
| RE37,531 E | 1/2002 | Chaco et al. |
| 6,337,631 B1 | 1/2002 | Pai et al. |
| 6,338,007 B1 | 1/2002 | Broadfield et al. |
| 6,339,732 B1 | 1/2002 | Phoon et al. |
| 6,345,260 B1 | 2/2002 | Cummings, Jr. et al. |
| 6,346,886 B1 | 2/2002 | De La Huerga |
| 6,347,553 B1 | 2/2002 | Morris et al. |
| 6,352,200 B1 | 3/2002 | Schoonen et al. |
| 6,353,817 B1 | 3/2002 | Jacobs et al. |
| 6,358,225 B1 | 3/2002 | Butterfield |
| 6,358,237 B1 | 3/2002 | Paukovits et al. |
| 6,361,263 B1 | 3/2002 | Dewey et al. |
| 6,362,591 B1 | 3/2002 | Moberg |
| 6,363,282 B1 | 3/2002 | Nichols et al. |
| 6,363,290 B1 | 3/2002 | Lyle et al. |
| 6,364,834 B1 | 4/2002 | Reuss et al. |
| 6,368,273 B1 | 4/2002 | Brown |
| 6,370,841 B1 | 4/2002 | Chudy et al. |
| 6,381,577 B1 | 4/2002 | Brown |
| 6,385,505 B1 | 5/2002 | Lipps |
| 6,393,369 B1 | 5/2002 | Carr |
| 6,397,190 B1 | 5/2002 | Goetz |
| 6,401,072 B1 | 6/2002 | Haudenschild et al. |
| 6,402,702 B1 | 6/2002 | Gilcher et al. |
| 6,406,426 B1 | 6/2002 | Reuss et al. |
| 6,407,335 B1 | 6/2002 | Franklin-Lees et al. |
| 6,408,330 B1 | 6/2002 | DeLaHuerga |
| 6,416,471 B1 | 7/2002 | Kumar et al. |
| 6,421,650 B1 | 7/2002 | Goetz et al. |
| 6,424,996 B1 | 7/2002 | Killcommons et al. |
| 6,427,088 B1 | 7/2002 | Bowman, IV et al. |
| 6,434,531 B1 | 8/2002 | Lancelot et al. |
| 6,434,569 B1 | 8/2002 | Tomlinson et al. |
| 6,438,451 B1 | 8/2002 | Lion |
| RE37,829 E | 9/2002 | Charhut et al. |
| 6,449,927 B2 | 9/2002 | Hebron et al. |
| 6,450,956 B1 | 9/2002 | Rappaport et al. |
| 6,458,102 B1 | 10/2002 | Mann et al. |
| 6,461,037 B1 | 10/2002 | O'Leary |
| 6,463,310 B1 | 10/2002 | Swedlow et al. |
| 6,468,242 B1 | 10/2002 | Wilson et al. |
| 6,470,234 B1 | 10/2002 | McGrady |
| 6,471,089 B2 | 10/2002 | Liff et al. |
| 6,471,645 B1 | 10/2002 | Warkentin et al. |
| 6,471,646 B1 | 10/2002 | Thede |
| 6,475,146 B1 | 11/2002 | Frelburger et al. |
| 6,475,148 B1 | 11/2002 | Jackson et al. |
| 6,475,180 B2 | 11/2002 | Peterson et al. |
| 6,478,737 B2 | 11/2002 | Bardy |
| 6,485,465 B2 | 11/2002 | Moberg et al. |
| 6,494,831 B1 | 12/2002 | Koritzinsky |
| 6,511,138 B1 | 1/2003 | Gardner et al. |
| 6,519,569 B1 | 2/2003 | White et al. |
| 6,537,244 B2 | 3/2003 | Paukovits |
| 6,542,902 B2 | 4/2003 | Dulong et al. |
| 6,542,910 B2 | 4/2003 | Cork et al. |
| 6,544,174 B2 | 4/2003 | West et al. |
| 6,544,228 B1 | 4/2003 | Heitmeier |
| 6,551,243 B2 | 4/2003 | Bocionek et al. |
| 6,551,276 B1 | 4/2003 | Mann et al. |
| 6,554,791 B1 | 4/2003 | Cartledge et al. |
| 6,554,798 B1 | 4/2003 | Mann et al. |
| 6,555,986 B2 | 4/2003 | Moberg |
| 6,558,321 B1 | 5/2003 | Burd et al. |
| 6,561,975 B1 | 5/2003 | Pool et al. |
| 6,562,001 B2 | 5/2003 | Lebel et al. |
| 6,564,104 B2 | 5/2003 | Nelson et al. |
| 6,564,105 B2 | 5/2003 | Starkweather et al. |

(56) References Cited

U.S. PATENT DOCUMENTS

| | | |
|---|---|---|
| 6,564,121 B1 | 5/2003 | Wallace et al. |
| 6,571,128 B2 | 5/2003 | Lebel et al. |
| 6,575,900 B1 | 6/2003 | Zweig et al. |
| 6,577,899 B2 | 6/2003 | Lebel et al. |
| 6,579,232 B2 | 6/2003 | Sakamaki et al. |
| 6,581,069 B1 | 6/2003 | Robinson et al. |
| 6,581,798 B2 | 6/2003 | Liff et al. |
| 6,584,336 B1 | 6/2003 | Ali et al. |
| 6,585,157 B2 | 7/2003 | Brandt et al. |
| 6,585,644 B2 | 7/2003 | Lebel et al. |
| 6,585,675 B1 | 7/2003 | O'Mahony et al. |
| 6,592,551 B1 | 7/2003 | Cobb |
| 6,593,528 B2 | 7/2003 | Franklin-Lees et al. |
| 6,602,469 B1 | 8/2003 | Maus et al. |
| 6,607,485 B2 | 8/2003 | Bardy |
| 6,610,973 B1 | 8/2003 | Davis, III |
| 6,613,009 B1 | 9/2003 | Bainbridge et al. |
| 6,616,633 B1 | 9/2003 | Butterfield et al. |
| 6,635,014 B2 | 10/2003 | Starkweather et al. |
| 6,648,821 B2 | 11/2003 | Lebel et al. |
| 6,659,948 B2 | 12/2003 | Lebel et al. |
| 6,664,893 B1 | 12/2003 | Eveland et al. |
| 6,668,196 B1 | 12/2003 | Villegas et al. |
| 6,669,663 B1 | 12/2003 | Thompson |
| 6,673,314 B1 | 1/2004 | Burbank et al. |
| 6,687,546 B2 | 1/2004 | Lebel et al. |
| 6,689,091 B2 | 2/2004 | Bui et al. |
| 6,694,191 B2 | 2/2004 | Starkweather et al. |
| 6,694,334 B2 | 2/2004 | DuLong et al. |
| 6,711,460 B1 | 3/2004 | Reese |
| 6,731,324 B2 | 5/2004 | Levy |
| 6,733,447 B2 | 5/2004 | Lai et al. |
| 6,735,497 B2 | 5/2004 | Wallace et al. |
| 6,740,075 B2 | 5/2004 | Lebel et al. |
| 6,746,398 B2 | 6/2004 | Hervy et al. |
| 6,758,810 B2 | 7/2004 | Lebel et al. |
| 6,768,425 B2 | 7/2004 | Flaherty et al. |
| 6,771,369 B2 | 8/2004 | Rzasa et al. |
| 6,775,602 B2 | 8/2004 | Gordon, Jr. et al. |
| 6,776,304 B2 | 8/2004 | Liff et al. |
| 6,790,198 B1 | 9/2004 | White et al. |
| 6,804,656 B1 | 10/2004 | Rosenfeld et al. |
| 6,810,290 B2 | 10/2004 | Lebel et al. |
| 6,811,533 B2 | 11/2004 | Lebel et al. |
| 6,811,534 B2 | 11/2004 | Bowman, IV et al. |
| 6,811,707 B2 | 11/2004 | Rovatti et al. |
| 6,813,473 B1 | 11/2004 | Bruker |
| 6,813,519 B2 | 11/2004 | Lebel et al. |
| 6,814,255 B2 | 11/2004 | Liff et al. |
| 6,820,093 B2 | 11/2004 | De La Huerga |
| 6,842,736 B1 | 1/2005 | Brzozowski |
| 6,847,861 B2 | 1/2005 | Lunak et al. |
| 6,854,088 B2 | 2/2005 | Massengale et al. |
| 6,871,211 B2 | 3/2005 | Labounty et al. |
| 6,873,268 B2 | 3/2005 | Lebel et al. |
| 6,877,530 B2 | 4/2005 | Osborne et al. |
| 6,880,034 B2 | 4/2005 | Manke et al. |
| 6,885,288 B2 | 4/2005 | Pincus |
| 6,887,201 B2 | 5/2005 | Bardy |
| 6,892,941 B2 | 5/2005 | Rosenblum |
| 6,912,549 B2 | 6/2005 | Rotter et al. |
| 6,913,590 B2 | 7/2005 | Sorenson et al. |
| 6,915,265 B1 | 7/2005 | Johnson |
| 6,915,823 B2 | 7/2005 | Osborne et al. |
| 6,928,452 B2 | 8/2005 | De La Huerga |
| 6,950,708 B2 | 9/2005 | Bowman, IV et al. |
| 6,958,705 B2 | 10/2005 | Lebel et al. |
| 6,974,437 B2 | 12/2005 | Lebel et al. |
| 6,975,924 B2 | 12/2005 | Kircher et al. |
| 6,976,628 B2 | 12/2005 | Krupa |
| 6,979,306 B2 | 12/2005 | Moll |
| 6,980,958 B1 | 12/2005 | Surwit et al. |
| 6,981,644 B2 | 1/2006 | Cheong et al. |
| 6,985,870 B2 | 1/2006 | Martucci et al. |
| 6,991,002 B2 | 1/2006 | Osborne et al. |
| 6,995,664 B1 | 2/2006 | Darling |
| 7,006,893 B2 | 2/2006 | Hart et al. |
| 7,015,806 B2 | 3/2006 | Naidoo et al. |
| 7,017,622 B2 | 3/2006 | Osborne et al. |
| 7,017,623 B2 | 3/2006 | Tribble et al. |
| 7,028,723 B1 | 4/2006 | Alouani et al. |
| 7,096,212 B2 | 8/2006 | Tribble et al. |
| 7,117,902 B2 | 10/2006 | Osborne |
| 7,151,982 B2 | 12/2006 | Liff et al. |
| 7,194,336 B2 | 3/2007 | DiGianfilippo et al. |
| 7,209,891 B1 | 4/2007 | Addy et al. |
| 7,213,009 B2 * | 5/2007 | Pestotnik ............... G16H 10/20 706/45 |
| 7,240,699 B2 | 7/2007 | Osborne et al. |
| 7,255,680 B1 | 8/2007 | Gharib |
| 7,277,579 B2 | 10/2007 | Huang |
| 7,277,757 B2 | 10/2007 | Casavant et al. |
| 7,317,967 B2 | 1/2008 | DiGianfilippo et al. |
| 7,321,861 B1 | 1/2008 | Oon |
| 7,343,224 B2 | 3/2008 | DiGianfilippo et al. |
| 7,403,901 B1 | 7/2008 | Carley et al. |
| 7,427,002 B2 | 9/2008 | Liff et al. |
| 7,493,263 B2 | 2/2009 | Helmus et al. |
| 7,499,581 B2 | 3/2009 | Tribble et al. |
| 7,509,280 B1 | 3/2009 | Haudenschild |
| 7,555,557 B2 | 6/2009 | Bradley et al. |
| 7,561,312 B1 | 7/2009 | Proudfoot et al. |
| 7,581,953 B2 | 9/2009 | Lehmann et al. |
| 7,599,516 B2 | 10/2009 | Limer et al. |
| 7,610,115 B2 | 10/2009 | Rob et al. |
| 7,630,908 B1 | 12/2009 | Amrien et al. |
| 7,636,718 B1 | 12/2009 | Steen et al. |
| 7,672,859 B1 | 3/2010 | Louie et al. |
| 7,698,019 B2 | 4/2010 | Moncrief et al. |
| 7,698,154 B2 | 4/2010 | Marchosky |
| 7,734,478 B2 | 6/2010 | Goodall et al. |
| 7,753,085 B2 | 7/2010 | Tribble et al. |
| 7,769,601 B1 | 8/2010 | Bleser et al. |
| 7,783,383 B2 | 8/2010 | Eliuk et al. |
| D624,225 S | 9/2010 | Federico et al. |
| 7,801,642 B2 | 9/2010 | Ansari et al. |
| 7,847,970 B1 | 12/2010 | McGrady |
| 7,853,621 B2 | 12/2010 | Guo |
| 7,904,822 B2 | 3/2011 | Monteleone et al. |
| 7,931,859 B2 | 4/2011 | Mlodzinski et al. |
| 7,937,290 B2 | 5/2011 | Bahir |
| 7,986,369 B1 | 7/2011 | Burns |
| 7,991,507 B2 | 8/2011 | Liff et al. |
| 8,165,893 B1 * | 4/2012 | Goldberg ............... G06Q 40/08 705/2 |
| 8,170,271 B2 | 5/2012 | Chen |
| 8,191,339 B2 | 6/2012 | Tribble et al. |
| 8,215,557 B1 | 7/2012 | Reno et al. |
| 8,220,503 B2 | 7/2012 | Tribble et al. |
| 8,225,824 B2 | 7/2012 | Eliuk et al. |
| D667,961 S | 9/2012 | Marmier |
| 8,267,129 B2 | 9/2012 | Doherty et al. |
| 8,271,128 B1 * | 9/2012 | Schultz ............... A61J 7/02 700/242 |
| 8,271,138 B2 | 9/2012 | Eliuk et al. |
| 8,280,549 B2 | 10/2012 | Liff et al. |
| 8,284,305 B2 | 10/2012 | Newcomb et al. |
| 8,374,887 B2 | 2/2013 | Alexander |
| 8,386,070 B2 | 2/2013 | Eliuk et al. |
| 8,548,824 B1 | 10/2013 | daCosta |
| 8,554,579 B2 | 10/2013 | Tribble et al. |
| D693,480 S | 11/2013 | Spiess et al. |
| 8,595,206 B2 | 11/2013 | Ansari |
| 8,666,541 B1 | 3/2014 | Ansari et al. |
| 8,678,047 B2 | 3/2014 | Tribble et al. |
| 8,810,408 B2 * | 8/2014 | Hanson ............... G16H 40/63 128/200.14 |
| D715,958 S | 10/2014 | Bossart et al. |
| 9,053,218 B2 | 6/2015 | Osborne et al. |
| D733,480 S | 7/2015 | Shao |
| D738,152 S | 9/2015 | Grasselli et al. |
| D753,428 S | 4/2016 | Shao |
| 9,362,969 B1 | 6/2016 | Burgess et al. |
| 9,382,021 B2 | 7/2016 | Tribble et al. |

(56) References Cited

U.S. PATENT DOCUMENTS

| | | |
|---|---|---|
| 9,662,273 B2 | 5/2017 | Ranalletta et al. |
| 9,930,297 B2 | 3/2018 | Alexander et al. |
| 9,956,145 B2 | 5/2018 | Thompson et al. |
| 2001/0001237 A1 | 5/2001 | Stroda et al. |
| 2001/0003177 A1 | 6/2001 | Schena et al. |
| 2001/0007053 A1 | 7/2001 | Bardy |
| 2001/0007932 A1 | 7/2001 | Kamen et al. |
| 2001/0011153 A1 | 8/2001 | Bardy |
| 2001/0016699 A1 | 8/2001 | Burbank et al. |
| 2001/0017817 A1 | 8/2001 | De La Huerga |
| 2001/0021801 A1 | 9/2001 | Bardy |
| 2001/0025138 A1 | 9/2001 | Bardy |
| 2001/0025156 A1 | 9/2001 | Bui et al. |
| 2001/0027634 A1 | 10/2001 | Hebron et al. |
| 2001/0028308 A1 | 10/2001 | De La Huerga |
| 2001/0030234 A1 | 10/2001 | Wiklof |
| 2001/0031944 A1 | 10/2001 | Peterson et al. |
| 2001/0032101 A1 | 10/2001 | Statius Muller |
| 2001/0034502 A1 | 10/2001 | Moberg et al. |
| 2001/0034614 A1 | 10/2001 | Fletcher-Haynes et al. |
| 2001/0034616 A1 | 10/2001 | Giannini |
| 2001/0037057 A1 | 11/2001 | Bardy |
| 2001/0037083 A1 | 11/2001 | Hartlaub et al. |
| 2001/0037217 A1 | 11/2001 | Abensour et al. |
| 2001/0037220 A1 | 11/2001 | Merry et al. |
| 2001/0041920 A1 | 11/2001 | Starkweather et al. |
| 2001/0044588 A1 | 11/2001 | Mault |
| 2001/0044731 A1 | 11/2001 | Coffman et al. |
| 2001/0047125 A1 | 11/2001 | Quy |
| 2001/0051764 A1 | 12/2001 | Bardy |
| 2001/0053885 A1 | 12/2001 | Gielen et al. |
| 2002/0002326 A1 | 1/2002 | Causey, III et al. |
| 2002/0002473 A1 | 1/2002 | Schrier et al. |
| 2002/0004645 A1 | 1/2002 | Carlisle et al. |
| 2002/0007285 A1 | 1/2002 | Rappaport |
| 2002/0010568 A1 | 1/2002 | Rubbert et al. |
| 2002/0010679 A1 | 1/2002 | Felsher |
| 2002/0013612 A1 | 1/2002 | Whitehurst |
| 2002/0016567 A1 | 2/2002 | Hochman et al. |
| 2002/0016568 A1 | 2/2002 | Lebel et al. |
| 2002/0016719 A1 | 2/2002 | Nemeth et al. |
| 2002/0016722 A1 | 2/2002 | Kameda |
| 2002/0019606 A1 | 2/2002 | Lebel et al. |
| 2002/0019748 A1 | 2/2002 | Brown |
| 2002/0022776 A1 | 2/2002 | Bardy |
| 2002/0025796 A1 | 2/2002 | Taylor et al. |
| 2002/0026104 A1 | 2/2002 | Bardy |
| 2002/0029157 A1 | 3/2002 | Marchosky |
| 2002/0029776 A1 | 3/2002 | Blomquist |
| 2002/0032582 A1 | 3/2002 | Feeney et al. |
| 2002/0032602 A1 | 3/2002 | Lanzillo, Jr. et al. |
| 2002/0038392 A1 | 3/2002 | De La Huerga |
| 2002/0040208 A1 | 4/2002 | Flaherty et al. |
| 2002/0044043 A1 | 4/2002 | Chaco et al. |
| 2002/0046062 A1 | 4/2002 | Kameda |
| 2002/0046185 A1 | 4/2002 | Villart et al. |
| 2002/0046346 A1 | 4/2002 | Evans |
| 2002/0052539 A1 | 5/2002 | Haller et al. |
| 2002/0052542 A1 | 5/2002 | Bardy |
| 2002/0052574 A1 | 5/2002 | Hochman et al. |
| 2002/0062227 A1 | 5/2002 | Yuyama |
| 2002/0062229 A1 | 5/2002 | Alban et al. |
| 2002/0065540 A1 | 5/2002 | Lebel et al. |
| 2002/0065686 A1 | 5/2002 | Monteleone et al. |
| 2002/0067273 A1 | 6/2002 | Jaques et al. |
| 2002/0072733 A1 | 6/2002 | Flaherty |
| 2002/0073250 A1 | 6/2002 | Ommering |
| 2002/0077852 A1 | 6/2002 | Ford et al. |
| 2002/0077865 A1 | 6/2002 | Sullivan |
| 2002/0082480 A1 | 6/2002 | Riff et al. |
| 2002/0082865 A1 | 6/2002 | Bianco et al. |
| 2002/0082868 A1 | 6/2002 | Pories et al. |
| 2002/0084904 A1 | 7/2002 | De La Huerga |
| 2002/0087120 A1 | 7/2002 | Rogers et al. |
| 2002/0091309 A1 | 7/2002 | Auer |
| 2002/0099283 A1 | 7/2002 | Christ et al. |
| 2002/0099301 A1 | 7/2002 | Bardy |
| 2002/0100762 A1 | 8/2002 | Liff et al. |
| 2002/0107476 A1 | 8/2002 | Mann et al. |
| 2002/0107707 A1 | 8/2002 | Naparstek et al. |
| 2002/0116226 A1 | 8/2002 | Auer et al. |
| 2002/0116509 A1 | 8/2002 | De La Huerga |
| 2002/0128606 A1 | 9/2002 | Cowan et al. |
| 2002/0128871 A1 | 9/2002 | Adamson et al. |
| 2002/0128880 A1 | 9/2002 | Kunikiyo |
| 2002/0133377 A1 | 9/2002 | Brown |
| 2002/0140675 A1 | 10/2002 | Ali et al. |
| 2002/0143254 A1 | 10/2002 | Maruyama |
| 2002/0156462 A1 | 10/2002 | Stultz |
| 2002/0158128 A1 | 10/2002 | Ashiuro |
| 2002/0165491 A1 | 11/2002 | Reilly |
| 2002/0169636 A1 | 11/2002 | Eggers et al. |
| 2002/0173875 A1 | 11/2002 | Wallace et al. |
| 2002/0188467 A1 | 12/2002 | Eke |
| 2002/0198473 A1 | 12/2002 | Kumar et al. |
| 2002/0198513 A1 | 12/2002 | Lebel et al. |
| 2002/0198624 A1 | 12/2002 | Greenwald |
| 2003/0006878 A1 | 1/2003 | Chung |
| 2003/0023177 A1 | 1/2003 | Bardy |
| 2003/0033532 A1 | 2/2003 | Marks |
| 2003/0036783 A1 | 2/2003 | Bauhahn et al. |
| 2003/0046114 A1 | 3/2003 | Davies et al. |
| 2003/0046280 A1 | 3/2003 | Rotter et al. |
| 2003/0046439 A1 | 3/2003 | Manke et al. |
| 2003/0050621 A1 | 3/2003 | Lebel et al. |
| 2003/0050731 A1 | 3/2003 | Rosenblum |
| 2003/0052787 A1 | 3/2003 | Zerhusen |
| 2003/0060753 A1 | 3/2003 | Starkweather et al. |
| 2003/0060754 A1 | 3/2003 | Reilly |
| 2003/0060765 A1 | 3/2003 | Campbell et al. |
| 2003/0060768 A1 | 3/2003 | Kiyatake |
| 2003/0060926 A1 | 3/2003 | Yuyama et al. |
| 2003/0065287 A1 | 4/2003 | Spohn et al. |
| 2003/0076736 A1 | 4/2003 | Buker et al. |
| 2003/0078534 A1 | 4/2003 | Hochman et al. |
| 2003/0079746 A1 | 5/2003 | Hickle |
| 2003/0083901 A1 | 5/2003 | Bosch et al. |
| 2003/0088238 A1 | 5/2003 | Poulsen et al. |
| 2003/0097092 A1 | 5/2003 | Flaherty |
| 2003/0114836 A1 | 6/2003 | Estes et al. |
| 2003/0117580 A1 | 6/2003 | Franz et al. |
| 2003/0125609 A1 | 7/2003 | Becker |
| 2003/0125611 A1 | 7/2003 | Bardy |
| 2003/0139701 A1 | 7/2003 | White et al. |
| 2003/0144878 A1 | 7/2003 | Wilkes et al. |
| 2003/0149599 A1 | 8/2003 | Goodall et al. |
| 2003/0154108 A1 | 8/2003 | Fletcher-Haynes et al. |
| 2003/0158508 A1 | 8/2003 | DiGianfilippo |
| 2003/0158755 A1 | 8/2003 | Neuman |
| 2003/0160683 A1 | 8/2003 | Blomquist |
| 2003/0163088 A1 | 8/2003 | Blomquist |
| 2003/0163223 A1 | 8/2003 | Blomquist |
| 2003/0163789 A1 | 8/2003 | Blomquist |
| 2003/0167035 A1 | 9/2003 | Flaherty et al. |
| 2003/0176933 A1 | 9/2003 | Lebel et al. |
| 2003/0179287 A1 | 9/2003 | Kozic et al. |
| 2003/0181851 A1 | 9/2003 | Mann et al. |
| 2003/0182164 A1 | 9/2003 | Blomquist |
| 2003/0195397 A1 | 10/2003 | Bardy |
| 2003/0200117 A1 | 10/2003 | Manetta et al. |
| 2003/0201697 A1 | 10/2003 | Richardson |
| 2003/0212379 A1 | 11/2003 | Bylund et al. |
| 2003/0225596 A1 | 12/2003 | Richardson et al. |
| 2003/0225728 A1 | 12/2003 | Moura |
| 2003/0231803 A1 | 12/2003 | Huang |
| 2004/0002874 A1 | 1/2004 | Shaffer et al. |
| 2004/0017475 A1 | 1/2004 | Akers et al. |
| 2004/0019607 A1 | 1/2004 | Moubayed et al. |
| 2004/0115132 A1 | 1/2004 | Brown |
| 2004/0039260 A1 | 2/2004 | Bardy |
| 2004/0039264 A1 | 2/2004 | Bardy |
| 2004/0051368 A1 | 3/2004 | Caputo et al. |
| 2004/0055611 A1 | 3/2004 | Penny et al. |
| 2004/0064343 A1 | 4/2004 | Korpman et al. |

(56) References Cited

U.S. PATENT DOCUMENTS

| | | |
|---|---|---|
| 2004/0073329 A1 | 4/2004 | Engleson |
| 2004/0088187 A1 | 5/2004 | Chudy et al. |
| 2004/0088374 A1 | 5/2004 | Webb et al. |
| 2004/0111293 A1 | 6/2004 | Firanek et al. |
| 2004/0116862 A1 | 6/2004 | Ray |
| 2004/0117215 A1 | 6/2004 | Marchosky |
| 2004/0128162 A1 | 7/2004 | Schlotterbeck et al. |
| 2004/0129616 A1 | 7/2004 | Mori et al. |
| 2004/0148195 A1 | 7/2004 | Kalies |
| 2004/0158193 A1 | 8/2004 | Bui et al. |
| 2004/0172283 A1 | 9/2004 | Vanderveen et al. |
| 2004/0172289 A1 | 9/2004 | Kozic et al. |
| 2004/0172300 A1 | 9/2004 | Mihai et al. |
| 2004/0193328 A1 | 9/2004 | Zaitsu et al. |
| 2004/0193453 A1 | 9/2004 | Butterfield et al. |
| 2004/0204673 A1 | 10/2004 | Flaherty |
| 2004/0204954 A1 | 10/2004 | Lacko |
| 2004/0215490 A1 | 10/2004 | Duchon et al. |
| 2004/0220829 A1 | 11/2004 | Baharav et al. |
| 2004/0225528 A1 | 11/2004 | Brock |
| 2004/0235446 A1 | 11/2004 | Flaherty et al. |
| 2004/0236630 A1 | 11/2004 | Kost et al. |
| 2004/0248295 A1 | 12/2004 | Katsuhiko et al. |
| 2004/0260233 A1 | 12/2004 | Garibotto et al. |
| 2004/0260577 A1 | 12/2004 | Dahlin et al. |
| 2005/0001033 A1 | 1/2005 | Cheong et al. |
| 2005/0017864 A1 | 1/2005 | Tsoukalis |
| 2005/0033124 A1 | 2/2005 | Kelly et al. |
| 2005/0033773 A1 | 2/2005 | Roberge et al. |
| 2005/0038680 A1 | 2/2005 | McMahon |
| 2005/0039742 A1 | 2/2005 | Hickle |
| 2005/0043665 A1 | 2/2005 | Vinci et al. |
| 2005/0045548 A1 | 3/2005 | Brugger et al. |
| 2005/0054923 A1 | 3/2005 | Pan |
| 2005/0060372 A1 | 3/2005 | DeBettencourt et al. |
| 2005/0080651 A1 | 4/2005 | Morrison et al. |
| 2005/0187794 A1 | 8/2005 | Kimak |
| 2005/0209737 A1 | 9/2005 | Kircher |
| 2005/0228238 A1 | 10/2005 | Monitzer |
| 2005/0279419 A1 | 12/2005 | Tribble et al. |
| 2006/0084042 A1 | 4/2006 | Weaver et al. |
| 2006/0124656 A1 | 6/2006 | Popovic, Jr. |
| 2006/0136095 A1 | 6/2006 | Rob et al. |
| 2006/0149416 A1 | 7/2006 | Mohapatra et al. |
| 2006/0161294 A1 | 7/2006 | DiMaggio |
| 2006/0173714 A1 | 8/2006 | Grotzinger, Jr. |
| 2006/0178578 A1 | 8/2006 | Tribble et al. |
| 2006/0181391 A1 | 8/2006 | McNeill et al. |
| 2006/0235881 A1 | 10/2006 | Masarie et al. |
| 2007/0043767 A1 | 2/2007 | Osborne et al. |
| 2007/0047980 A1 | 3/2007 | Limer et al. |
| 2007/0088568 A1 | 4/2007 | Goodall et al. |
| 2007/0110305 A1 | 5/2007 | Corcoran et al. |
| 2007/0125442 A1 | 6/2007 | Tribble et al. |
| 2007/0168228 A1 | 7/2007 | Lawless |
| 2007/0179806 A1 | 8/2007 | Knowlton et al. |
| 2007/0189597 A1 | 8/2007 | Limer et al. |
| 2007/0192139 A1 | 8/2007 | Cookson et al. |
| 2007/0216998 A1 | 9/2007 | Sander |
| 2007/0239482 A1 | 10/2007 | Finn et al. |
| 2007/0239997 A1 | 10/2007 | Qu et al. |
| 2008/0046292 A1 | 2/2008 | Myers et al. |
| 2008/0056556 A1 | 3/2008 | Eller et al. |
| 2008/0059228 A1 | 3/2008 | Bossi et al. |
| 2008/0091467 A1 | 4/2008 | Moncrief et al. |
| 2008/0119958 A1 | 5/2008 | Bear et al. |
| 2008/0125897 A1 | 5/2008 | DiGianfilippo et al. |
| 2008/0147554 A1 | 6/2008 | Stevens et al. |
| 2008/0195246 A1 | 8/2008 | Tribble et al. |
| 2008/0306926 A1 | 12/2008 | Friedlander et al. |
| 2009/0024414 A1 | 1/2009 | Mansour et al. |
| 2009/0080408 A1 | 3/2009 | Natoli et al. |
| 2009/0097368 A1 | 4/2009 | Vlutters et al. |
| 2009/0138340 A1 | 5/2009 | Borr et al. |
| 2009/0188937 A1 | 7/2009 | Kim |
| 2009/0205877 A1 | 8/2009 | Claypool |
| 2009/0210252 A1 | 8/2009 | Silver |
| 2009/0235194 A1 | 9/2009 | Arndt et al. |
| 2009/0258331 A1 | 10/2009 | Do et al. |
| 2009/0285762 A1 | 11/2009 | Flower |
| 2009/0313044 A1 | 12/2009 | Haque et al. |
| 2009/0318561 A1* | 12/2009 | Davis .................. A61K 31/165 514/625 |
| 2009/0323170 A1 | 12/2009 | Lin |
| 2009/0324032 A1 | 12/2009 | Chen |
| 2010/0017031 A1 | 1/2010 | Rob et al. |
| 2010/0091281 A1 | 4/2010 | Suzuki |
| 2010/0094653 A1 | 4/2010 | Tribble et al. |
| 2010/0128165 A1 | 5/2010 | Newcomb et al. |
| 2010/0157293 A9 | 6/2010 | Rzasa et al. |
| 2010/0179169 A1 | 7/2010 | Davis |
| 2010/0185456 A1 | 7/2010 | Kansal |
| 2010/0241270 A1 | 9/2010 | Eliuk et al. |
| 2011/0119088 A1 | 5/2011 | Gunn |
| 2011/0191121 A1 | 8/2011 | Fioravanti |
| 2011/0202366 A1 | 8/2011 | Akers et al. |
| 2011/0208350 A1 | 8/2011 | Eliuk et al. |
| 2011/0257991 A1 | 10/2011 | Shukla |
| 2011/0267465 A1 | 11/2011 | Alexander et al. |
| 2012/0097290 A1 | 4/2012 | Mikhaeil |
| 2012/0200596 A1 | 8/2012 | Gotou et al. |
| 2012/0211565 A1 | 8/2012 | Colavito et al. |
| 2012/0303388 A1 | 11/2012 | Vishnubhalta et al. |
| 2012/0323602 A1 | 12/2012 | Ryan et al. |
| 2013/0079581 A1 | 3/2013 | Agamaite et al. |
| 2013/0090947 A1 | 4/2013 | Nockley |
| 2013/0197445 A1 | 8/2013 | Schabbach et al. |
| 2013/0262138 A1 | 10/2013 | Jaskela et al. |
| 2013/0279774 A1 | 10/2013 | Helgason et al. |
| 2013/0304510 A1 | 11/2013 | Chan et al. |
| 2013/0314535 A1 | 11/2013 | Yuyama et al. |
| 2013/0342676 A1 | 12/2013 | Amano |
| 2014/0022569 A1 | 1/2014 | Matsui et al. |
| 2014/0114687 A1* | 4/2014 | Frank .................... G16H 40/67 705/3 |
| 2014/0156064 A1 | 6/2014 | Crawford et al. |
| 2014/0156294 A1 | 6/2014 | Tribble et al. |
| 2014/0214199 A1 | 7/2014 | Utech et al. |
| 2014/0214436 A1 | 7/2014 | Utech et al. |
| 2014/0278448 A1* | 9/2014 | Sadeghi ................. G06Q 10/10 705/2 |
| 2014/0350950 A1 | 11/2014 | Jaskela et al. |
| 2015/0205932 A1 | 7/2015 | Tribble |
| 2015/0227719 A1 | 8/2015 | Ranalletta |
| 2015/0272320 A1 | 10/2015 | Ranalletta et al. |
| 2015/0278477 A1 | 10/2015 | Tribble |
| 2015/0286799 A1 | 10/2015 | Padmani |
| 2016/0072985 A1 | 3/2016 | Sandmann et al. |
| 2016/0092638 A1 | 3/2016 | Padmani |
| 2016/0092639 A1 | 3/2016 | Padmani |
| 2016/0140315 A1 | 5/2016 | Diaz et al. |
| 2016/0210437 A1* | 7/2016 | Padmani ............... G06Q 50/22 |
| 2016/0371462 A1 | 12/2016 | Wallen |
| 2017/0372034 A1 | 12/2017 | Tribble |

FOREIGN PATENT DOCUMENTS

| | | |
|---|---|---|
| CN | 1131076 | 12/2003 |
| EP | 0237588 | 9/1987 |
| EP | 0462466 | 12/1991 |
| EP | 0505627 | 9/1992 |
| EP | 0522527 | 1/1993 |
| EP | 0439355 | 9/1994 |
| EP | 0844581 | 5/1998 |
| EP | 0960627 | 12/1999 |
| EP | 0970655 | 1/2000 |
| EP | 1072994 | 2/2001 |
| EP | 1107158 A1 | 6/2001 |
| EP | 1097671 | 2/2003 |
| EP | 1501037 A2 | 1/2005 |
| GB | 994977 A | 6/1965 |
| GB | 2210713 | 2/1987 |
| GB | 2279784 | 1/1995 |
| GB | 2285135 | 6/1995 |

(56) References Cited

FOREIGN PATENT DOCUMENTS

| | | |
|---|---|---|
| GB | 2379037 | 2/2003 |
| JP | 53137644 | 12/1978 |
| JP | 61066950 | 4/1986 |
| JP | 63068133 | 3/1988 |
| JP | 2111375 | 4/1990 |
| JP | 3423055 B2 | 1/1994 |
| JP | 6086813 | 3/1994 |
| JP | 06327636 | 11/1994 |
| JP | 07204253 A | 8/1995 |
| JP | 08315040 A | 11/1996 |
| JP | 8315040 A | 11/1996 |
| JP | 104585 | 1/1998 |
| JP | 10014890 | 1/1998 |
| JP | 10079770 | 3/1998 |
| JP | 2000036032 A | 2/2000 |
| JP | 03055131 | 4/2000 |
| JP | 20000270376 A | 9/2000 |
| JP | 2002011095 | 1/2002 |
| JP | 2002092181 A | 3/2002 |
| JP | 2002099619 A | 4/2002 |
| JP | 2002520718 | 7/2002 |
| JP | 2003022322 | 1/2003 |
| JP | 2003062043 A | 3/2003 |
| JP | 2004078970 | 3/2004 |
| JP | 2004280327 A | 10/2004 |
| JP | 2004326436 | 11/2004 |
| JP | 2004340770 A | 12/2004 |
| JP | 2005252710 A | 9/2005 |
| JP | 2006033291 A | 2/2006 |
| JP | 2006195526 | 7/2006 |
| JP | 2006195526 A | 7/2006 |
| JP | 2006334062 | 12/2006 |
| JP | 2007115089 A | 5/2007 |
| JP | 2007190395 A | 8/2007 |
| JP | 2007198934 A | 8/2007 |
| JP | 2008139201 A | 6/2008 |
| JP | 4276654 B2 | 6/2009 |
| JP | 2009265827 A | 11/2009 |
| JP | 2010056619 A | 3/2010 |
| JP | 2010170504 A | 8/2010 |
| JP | 2010533927 | 10/2010 |
| JP | 2011151430 A | 8/2011 |
| JP | 2012078265 | 4/2012 |
| JP | 5342197 B2 | 11/2013 |
| JP | 5747150 B2 | 7/2015 |
| JP | 6086813 | 3/2017 |
| KR | 20000036642 | 7/2000 |
| KR | 1020000036642 | 7/2000 |
| KR | 20010094703 A | 11/2001 |
| KR | 1020010094703 | 11/2001 |
| KR | 20050054379 | 12/2003 |
| KR | 20110115927 A | 10/2011 |
| KR | 1020110115927 | 10/2011 |
| KR | 20130001500 | 1/2013 |
| WO | WO8400493 | 2/1984 |
| WO | WO9524010 A1 | 9/1995 |
| WO | WO9634291 A1 | 10/1996 |
| WO | WO9741525 | 11/1997 |
| WO | WO9814275 A1 | 4/1998 |
| WO | WO9815092 A1 | 4/1998 |
| WO | WO9824358 A1 | 6/1998 |
| WO | WO9833433 A1 | 8/1998 |
| WO | WO9859487 | 12/1998 |
| WO | WO9904043 | 1/1999 |
| WO | WO9910029 | 3/1999 |
| WO | WO9942933 | 8/1999 |
| WO | WO9944162 | 9/1999 |
| WO | WO9959472 | 11/1999 |
| WO | WO0013588 | 3/2000 |
| WO | WO0029983 | 5/2000 |
| WO | WO0043941 | 7/2000 |
| WO | WO0052437 | 9/2000 |
| WO | WO0052626 | 9/2000 |
| WO | WO0057339 | 9/2000 |
| WO | WO0060449 | 10/2000 |
| WO | WO0069331 | 11/2000 |
| WO | WO0072181 | 11/2000 |
| WO | WO0078374 | 12/2000 |
| WO | WO0101305 | 1/2001 |
| WO | WO0102979 | 1/2001 |
| WO | WO0106468 | 1/2001 |
| WO | WO0145774 | 6/2001 |
| WO | WO0217777 | 7/2002 |
| WO | WO02091276 A1 | 11/2002 |
| WO | WO03025826 A2 | 3/2003 |
| WO | WO03094073 | 11/2003 |
| WO | WO2004070557 | 8/2004 |
| WO | WO2004070994 | 8/2004 |
| WO | 2006060572 A1 | 6/2006 |
| WO | 2014164875 | 9/2014 |
| WO | 2014164875 A1 | 9/2014 |
| WO | 2014/164875 A1 | 10/2014 |
| WO | 2014164875 A1 | 10/2014 |
| WO | 20140164875 A1 | 10/2014 |

OTHER PUBLICATIONS

Japanese Office Action and English translation for related Japanese Application No. 2017-546118; action dated Sep. 18, 2018; (14 pages).
Written Opinion issued by the Singapore Patent Office for related Singapore Patent Application No. 11201707114X; opinion dated Mar. 26, 2018; (8 pages).
Texas Administrative Code, Title 22, Part 15, Ch 291, Rules 20, 36, and 71-74. Feb. 10, 2004.
Peterson, Charles D. and Anderson, Jr., Howard C.; "The North Dakota Telepharmacy Project: Restoring and Retaining Pharmacy Services in Rural Communities" Feb. 1, 2004.
Phillips, Jon, Associate Director of Telemedicine; "Telepharmacy at Texas Tech," presented Apr. 30, 2003, published at http://www.ttuhsc.edu/telemedicine/publication.htm at least by Jun. 22, 2003 Jun. 22, 2003.
European Search Report for related European Application No. 16759518.0; action dated Sep. 25, 2018; (7 pages).
AHRQ Health Information Technology Program—Update Jun. 2005 Fact Sheet,, http://www.ahrq.gov/research/findings/factsheets/it/hitfact/index.html—3 pages.
Albert A. Cook, "An integrated nursing-pharmacy approach to a computerized medication dispensing/administration system," Hospital Pharmacy, May 1985, pp. 321-325, vol. 20, JB Lippincott Company, Philadelphia, PA.
Allan T. Pryor, "Current State of Computer-based Patient Record Systems," Aspects of the Computer-based Patient Record, 1992, pp. 67-82, Springer-Verlag, New York, NY.
Anderson, Howard "A Narrative on the History of the Development of Telepharmacy in North Dakota from the Board of Pharmacy's Perspective Recorded by Excerpts from Board Minutes", Feb. 2006.
Angaran, "Telemedicine and telepharmacy: Current status and future implications", Am J Health-Syst Pharm, vol. 56, Jul. 15, 1999, pp. 1404-1405.
Ann Slone Endo, "Using Computers in Newborn Intensive Care Settings," American Journal of Nursing, Jul. 1981, pp. 1336-1337.
Anonymous, "Chains covet customized pharmacy integration" Drug Store New, Aug. 18, 2003, vol. 25, No. 10—p. 73.
Automated Dispensing Technologies: Directory of Vendors, http://pharmacyautomation.com/vendors.html, Jun. 5, 2003—3 pages.
Auto Syringe® AS40A Infusion Pump Technical Manual, 1995, 89 pages, Baxter Healthcare Corporation, Deerfield, IL.
Auto Syringe® AS40A: Model AS40A Infusion Pump Operation Manual, undated, 78 pages, Baxter Healthcare Corporation, Deerfield, IL.
Baxa Corporation, DoseEdge The Leading Edge in Dose Management, Brochure, published copyright date 2010—5 pages.
Baxa Corporation, Product Catalog 2010-2011, published at least by Sep. 15, 2012, https://web.archive.org/web/20120915210739http://www.baxa.com/resources/docs/BaxaCatalog.pdf (52 pages).
Bell Atlantic Healthcare Systems, Inc., court exhibit, StatLan Functions and Features, Specification, release 3.5, dated Nov. 12, 1992, 49 pages.

(56) References Cited

OTHER PUBLICATIONS

Ben Schneiderman, "Designing the User Interface: Strategies for Effective Human-Computer Interaction," 2d Ed., 1992, Chapter 5: Direct Manipulation (56 pages), Addison-Wesley Publishing Company.
"Block Medical: Growing with Home Infusion Therapy," taken from Invivo, the Business and Medicine Report, Apr. 1991, pp. 7-9.
Bynum et al., "The Effect of Telepharmacy Counseling on Metered-Dose Inhaler Technique among Adolescents with Asthma in Rural Arkansas", Telemedicine Journal and e-health, vol. 7, No. 3, 2001, Mary AnnLiebert, Inc., pp. 207-218.
Cabral, Jr. et al., "Multmedia Systems for Telemedicine Systems for Telemedicine and Their Communications Requirements," IEEE Communications Magazine Jul. 1996, pp. 20-27.
Cardinal Health Introduces Rxe-source(SM) to Address Pharmacist Labor Shortage and Medication Safety Challenges at Hospitals. PR Newswire, Feb. 25, 2003—5 pages.
Casey, Michelle M. et al., "Pharmacist Staffing and the Use of Technology in Small Rural Hospitals: Implications for Medication Safety" Upper Midwest Rural Health Research Center, Dec. 2005—51 pages.
Cato Reference Manual, Support for Trial Version (Abridged), Vienna, May 2004 Jun. 1, 2004.
Cato Reference Manual, Vienna, May 2005 May 1, 2005.
Charles Safran, M.D et al., "Computer-Based Support for Clinical Decision Making," Clinical Computin, vol. 7, No. 5 (1990), pp. 319-322.
Clayton M. Curtis, "A Computer-based Patient Record Emerging from the Public Sector: The Decentralized Hospital Computer Program," First Annual Nicholas E. Davies Award Proceedings of the CPR Recognition Symposium, 1995, pp. 75-132, Computer-based Patient Record Institute, Inc., Bethesda, MD.
Clement J. McDonald, M.D. et al., "The Three-Legged Stool: Regenstrief Institute for Health Care," Third Annual Nicholas E. Davies Award Proceedings of the CPR Recognition Symposium, 1997, pp. 131-158, Computer-based Patient Record Institute, Inc., Bethesda, MD.
Clement J. McDonald, M.D. et al., The Regenstrief Medical Record System: 20 Years of Experience in Hospitals, Clinics, and Neighborhood Health Centers,: M.D. Computing, 1992 pp. 206-217, vol. 9, No. 4, Springer-Verlag, New York, NY.
Clifton, G. Dennis et al., "Provision of pharmacy services to underserved populations via remote dispensing and two-way videoconferencing" Am J Health-Syst Pharm, vol. 60, Dec. 15, 2003 oe pp. 2577-2582.
Dan Murphy, "Nuclear Pharmacy Primer", Radiation Protection Management, vol. 20, No. 5 (2003), pp. 1-10.
Dan Scheraga; "Tech firms answer chain pharmacy's call for productivity," Drug Store News; Dec. 15, 2003; 25, 17; ProQuest Research Library, p. 31-32.
Daniel Andresen et al., "Scalability Issues for High Performance Digital Libraries on the World Wide Web," Proceedings of ADL '96, 1996, pp. 139-148, IEEE.
Daniel J. Nigrin et al., "Glucoweb: A Case Study of Secure, Remote Biomonitoring and Communication," Proceedings of the 2000, 5 pages, American Medical Informatics Association, Bethesda, MD.
Darryl V. Wareham et al., "Combination Medication Cart and Computer Terminal in Decentralized Drug Distribution," American Journal of Hospital Pharmacy, Jun. 1983, pp. 976-978, vol. 40, American Society of Hospital Pharmacists.
Dart, Luann, "Digital Doses" Rural Electric, Jan. 2005—pp. 28-31.
Deborah J. Mayhew, "Principles and Guidelines in Software user Interface Designs," 1992, selected portions of Chapter 9, 17 pages, Prentice-Hall, Inc.
Defendants Initial Invalidity Contentions with Exhibits A and B dated Sep. 8, 2014; Civil Action No. 1:14-cv-00222.
Dennis D. Cote et al., "Robotic system for i.v. antineoplastic drug preparation: Description and preliminary evaluation under simulated conditions," American Journal of Hospital Pharmacy, Nov. 1989, pp. 2286-2293, vol. 46, American Society of Hospital Pharmacists.
Donna Young; "Loan repayments help pharmacists provide care in medically underserved areas," American Journal of Health—System Pharmacy; Nov. 1, 2003, pp. 2186-2188, vol. 60.
Environmental Scan of Pharmacy Technicians; M. MacInnis; Canadian Pharmacists Association; Sep. 2001.
Exhibit 1, Publications Manually Reviewed for the Search to U.S. Pat. No. 8,347,887 titled "System and Method for Remotely Supervising and Verifying Pharmacy Functions" As of Jun. 25, 2014.
Exhibit 1001 U.S. Pat. No. 8,374,887, Alexander issued Feb. 12, 2013.
Exhibit 1002 Patent File History U.S. Pat. No. 8,374,887.
Exhibit 1003, Declaration of Mr. Brian T. Hart from U.S. Pat. No. 8,374,887.
Exhibit 1004, Declaration of Wayne H. Grant from U.S. Pat. No. 8,374,887.
Exhibit 1005, 22 TAC §§291.20, 291.36, and 291.71-291.74 date issued Mar. 5, 2015 from U.S. Pat. No. 8,374,887.
Exhibit 1006 U.S. Pat. No. 6,711,460 Reese issued Mar. 23, 2004 from U.S. Pat. No. 8,374,887.
Exhibit 1009, Peterson et al., The North Dakota Telepharmacy Project: Restoring and Retaining Pharmacy Services in Rural Communities; the journal of Pharmacy Technology, vol. 20, No. 1, Jan./Feb. 2004—pp. 1-39 from U.S. Pat. No. 8,374,887.
Exhibit 1010, Declaration of Benjamin E. Weed from U.S. Pat. No. 8,374,887.
Exhibit 1011, Complaint—*Alexander* v. *Baxter*, (W.D.Texas 2014) filed Mar. 13, 2014 from U.S. Pat. No. 8,374,887.
Exhibit 1012, Charles F. Seifert et al., "The Training of a Telepharmacist: Addressing the Needs of Rural West Texas," American Journal of Pharmaceutical Education, 2004; 68 (3) Article 60—pp. 1-9 from U.S. Pat. No. 8,374,887.
Exhibit 1013, Assignment Emily H. Alexander to Becton, Dickinson and Company; U.S. Appl. No. 13/747,231; Reel 034110/Frame 0789 from U.S. Pat. No. 8,374,887.
Exhibit 1014, Exhibit A—Corrected Parties' Claims Construction Terms, Proposed Construction and cites Civil, 1:14cv-00222-LY—pp. 1-7 from U.S. Pat. No. 8,374,887.
Exhibit 1015, Information about Telepharmacy presentation 42503 and Presentation Telepharmacy at Texas Tech; Jon Phillips—1-27 from U.S. Pat. No. 8,374,887.
Exhibit 1017, Declaration of Dr. Roger W. Anderson in Support of Becton, Dickinson & Company's Response to Baxter's Motion for Summary Judgment of Invalidity Based Upon 35 U.S.C. § 101 filed Jan. 15, 2015 from U.S. Pat. No. 8,374,887.
Exhibit 1018, Plaintiff's Claim Construction Brief, 1:14-cv-222-LY filed Oct. 17, 2014 from U.S. Pat. No. 8,374,887.
Exhibit 1019, Plaintiff's Reply Claim Construction Brief, 1:14-cv-222-LY filed Nov. 7, 2014 from U.S. Pat. No. 8,374,887.
Exhibit 1020, The United States Pharmacopeia—the Official Compendia of Standards; 2004 from U.S. Pat. No. 8,374,887.
Exhibit 1021, Curriculum Vitae of Brian T Hart from U.S. Pat. No. 8,374,887.
Exhibit 1022, Curriculum Vitae of Wayne H Grant—Expert oversight—Expert Witness-Litigation Support from U.S. Pat. No. 8,374,887.
Exhibit 1023, Charles D Peterson et al., "The North Dakota Telepharmacy Project: Restoring and Retaining Pharmacy Services in Rural Communities," J Pharm Technol, 2004; vol. 20—pp. 028-039 from U.S. Pat. No. 8,374,887.
Exhibit 1025, Affidavit of Christopher Butler with attached Telemedicine Report Archive dated Mar. 4, 2015—6 pages from U.S. Pat. No. 8,374,887.
Exhibit 1026, Affidavit of Christopher Butler with attached presentation Telepharmacy at Text Tech—Jon Phillips dated Mar. 4, 2015—31 pages from U.S. Pat. No. 8,374,887.
Exhibit 1027, Order on Motion for Summary Judgment filed Aug. 3, 2015 from U.S. Pat. No. 8,374,887.
Exhibit 1028, Final Judgment filed Aug. 3, 2015 from U.S. Pat. No. 8,374,887.
Exhibit 1029 Charles Seifert from U.S. Pat. No. 8,374,887.

(56) References Cited

OTHER PUBLICATIONS

Exhibit 1030 Deposition of Charles Seifert Dec. 4, 2015 from U.S. Pat. No. 8,374,887.
Exhibit 1031 Deposition of Diane B. Ginsburg, PhD. Dec. 16, 2015 from U.S. Pat. No. 8,374,887.
Exhibit 1032 Texas Administrative Code, Title 22, Chapter 291, Subchapter A, Section 291.23 as in effect on Feb. 1, 2004 from U.S. Pat. No. 8,374,887.
Felkey, Bill G., "Integrating Technology at the Point of Care", Insight, Jan. 2004—pp. 8-10.
Formula for Patient Safety; ScriptPro; Aug. 17, 2003.
Fred Puckett, "Medication-management component of a point-of-care information system," Am. J. Health-Syst.Pharm., Jun. 15, 1995, pp. 1305-1309, vol. 52, American Society of Health-System Pharmacists, Inc.
"GE ImageQuant TL 7.0 Image Analysis Software" User Manual, May 2007, http://nba.uth.tmc.edu/Assets/pdf/other/typhoon-supporting-files/IQTL-UserManual.pdf, Uppsala, Sweden.
Gerald E. Meyer et al., "Use of bar codes in inpatient drug distribution," Am. J. Hosp. Pharm., May 1991, pp. 953-966, vol. 48, American Society of Hospital Pharmacists, Inc.
Ghent, Natale, "Pharmacists go digital to fight shortage", Pharmacy Practice 20.11 (Nov. 2004): 47—2 pages.
Gilad J. Kuperman, M.D. et al., "Innovations and research review: The impact of the HELP computer system on the LDS Hospital paper medical record," Topics in Health Record Management, 1991, pp. 76-85, vol. 12, Issue 2, Aspen Publishers, Inc.
"Global Med Announces First Safetrace TX™ Sale," Apr. 1, 1999, 2 pages.
Global Med Technologies, Inc. Introduces PeopleMed™.com, inc., A Chronic Disease Management Application Service Provider (ASP) Subsidiary, Jan. 11, 2000, 2 pages, Global med Technologies, Inc., Denver, CO.
Gretchen A. Barry et al., "Bar-code technology for documenting administration of large-volume intravenous solutions," American Journal of Hospital Pharmacy, Feb. 1989, pp. 282-287, vol. 46, American Society of Hospital Pharmacists.
H. Paul Hammann et al., "A World Wide Web Accessible Multi-Species ECG Database," 1997, pp. 7-12, ISA.
Halverson, Daniel R. IsoRx: TelePharmacy Software presentation—23 pages.
Henry J. Lowe et al., "WebReport: A World Wide Web Based Clinical Multimedia Reporting System," 1996, pp. 314-318, AMIA, Inc.
"Hospitals battle errors with bar codes," Mar. 24, 2004, 3 pages, MSNBC.
Howard L. Bleich et al., "Clinical Computing in a Teaching Hospital," Use and Impact of Computers in Clinical Medicine, 1987, pp. 205-223 and selected pages, Springer-Verlag, New York, NY. http://isorx.com/ Jan. 29, 2004.
http://www.scriptpro.com/products//sp-200/main.htm, Feb. 13, 2004, Product listing for SP 200® Robotic Prescription Dispensing System.
http://www.scriptpro.com/products/space/space200.htm, Feb. 10, 2004, Product listing for SP Automation Center 200TM (Space 200TM) Prescription Dispensing Automation Center.
Hughes, Shirley, "Bedside Terminals: Clinicom," Clinical Computing, Jan./Feb. 1988, pp. 22-28, vol. 5, No. 1.
IPR Decision Paper No. 8 Entered Aug. 13, 2015 from U.S. Pat. No. 8,374,887.
IPR Final Written Decision Paper No. 29 Entered Jul. 11, 2016 from U.S. Pat. No. 8,374,887.
James Kazmer et al., "The Creation of Virtual Electronic Medical Record," 1996, 17 pages.
Jennifer Langham; "Taking Automation to New Levels," Insight, the QS/1 Magazine, Oct. 2002; pp. 2-5.
John Frady; "What's New in RxCare Plus 17.2," Insight, the QS/1 Magazine, Apr. 2002; pp. 2-3, 14.
Jones, et al., "Use of a remote computerized system for study documentation in clinical trials" Drug Information Journal, Oct.-Dec. 1998, vol. 32, No. 4 oe pp. 1153-1163.
Karen E. Bradshaw et al., "Physician decision-making—Evaluation of data used in a computerized ICU," International Journal of Clinical Monitoring and Computing, 1984, pp. 81-91, vol. 1, Martinus Nijhoff Publishers, Netherlands.
Kastango, Eric S. and Bradshaw, Brian D., "USP chapter 797: Establishing a practice standard for compounding sterile preparations in pharmacy" Am J Health-Syst Pharm., Sep. 15, 2004, vol. 61—pp. 1928-1938.
Kenneth N. Barker et al., "Effect of an automated bedside dispensing machine on medication errors," American Journal of Hospital Pharmacy, Jul. 1984, pp. 1352-1358, vol. 41, No. 7, American Society of Hospital Pharmacists.
Keeys, Christopher A. et al., "Providing nighttime pharmaceutical services through telepharmacy" Am J Health-Syst Pharm, Apr. 15, 2002, vol. 59—pp. 716-721.
Khan, Shamima et al., "Is There a Successful Business Case for Telepharmacy?" Telemedicine and e-Health, vol. 14, No. 3, Apr. 2008, pp. 235-245.
Kimber, Michael B. et al., "Telepharmacy-Enabling Technology to Provide Quality Pharmacy Services in Rural and Remote Communities" Journal of Pharmacy Practice and Research, vol. 36, No. 2, 2006—128-133.
Kodak DirectView PACS—Rural Hospital Joins the Big Leagues PACS/Enterprise Information management (EIM) Solution—www.kodak.com/go/medical—4 pages.
Kosub, David, "Device allows pharmacy care in remote areas" Pharmacy Practice, vol. 20, No. 10, Oct. 2004—pp. 12-13.
Koutnik, Eileen, Assistnat Editor, Pharmacy Times, "The Pharmacy of Tomorrow" Pharmacy Times, Aug. 1, 2003—3 pages.
Larry B. Grandia, B.S.E. et al., "Building a computer-based Patient Record System in an Evolving Integrated Health System," First Annual Nicholas E. Davies Award Proceedings of the CPR Recognition Symposium, 1995, pp. 19-55, Computer-based Patient Record Institute, Inc., Bethesda, MD.
Lefkowitz, Sheldon et al., "A Trial of the Use of Bar Code Technology to Restructure a Drug Distribution and Administration System," 1991, pp. 239-242, Hospital Pharmacy, vol. 26.
LP, "ATM-STyle Drug Dispensers Taking Hold In Areas With Limited Pharmacist Services" Pharmacy Practice News, Jan. 2004, vol. 31, No. 1—4 pages.
"The Longitudinal Clinical Record: A View of the Patient," taken from Proceedings of the 1994 Annual HIMSS Conference, Feb. 14, 1994, pp. 239-250, Healthcare Information and Management Systems Society, Chicago, Illinois, USA.
Lustig, Ahuva, "Medication error prevention by pharmacists—An Israeli solution" Pharmacy World & Science, 2000, vol. 22, No. 1—pp. 21-25.
Medicaid Memo—Department of Medical Assistance Services (Converting NDCs from 10-digits to 11-digits) May 31, 2007.
Medcin® Technical Overview, undated, 111 pages, Medicomp Systems.
Michael H. Mackin, "Impact of Technology on Environmental Therapeutic Device Design," Medical Instrumentation, Feb. 1987, pp. 33-35, vol. 21, No. 1, Association for the Advancement of Medical Instrumentation.
Michelle M. Casey, M.S., Jill Klingner, R.N., M.S., and Ira Moscovice, Ph.D.; "Access to Rural Pharmacy Services In Minnesota, North Dakota, and South Dakota, " Working Paper Series, Jul. 2001, #36.
Monane et al., "Improving Prescribing Patterson for the Elderly Through an Online Drug Utilization Review Intervention", JAMA, Oct. 14, 1998, vol. 280, No. 14—pp. 1249-1252.
Morris, Aisha M., Schneider, Philip J., Pedersen, Craig A. and Mirtallo, Jay M. "National survey of quality assurance activities for pharmacy-compounded sterile preparations" Am J Health-Syst Pharm, Dec. 15, 2003, vol. 60—pp. 2567-2576.
Murray, Michael D. et al. "Effects of Computer-based Prescribing on Pharmacist Work Patterns" Journal of the American Medical Informatics Association, Nov./Dec. 1998, vol. 5, No. 6—pp. 546-553.

(56) References Cited

OTHER PUBLICATIONS

Napoli, M. et al., "Picture archiving and communication in radiology", Rays. Jan.-Mar. 2003—PubMed-NCBI http://www.ncbi.nlm.m=nih.gov/pubmed/14509181—Abstract.
Nissen et al., Can telepharmacy provide pharmacy services in the bush, School of Pharmacy, University of Queensland, Brisbane, Australia, Journal of Telemedicine and Telecare 2003, vol. 9 (Suppl. 2): S2:39-41.
North Dakota Century Code Statute Law—State Board of Pharmacy—219 pages.
Parks, Liz, "Annual report of retail pharmacy: Using central-fill to maximize dispensing" Drug Store News, Aug. 20, 2001 vol. 24, No. 11—pp. 51, 75.
Parsons, et al., "Digital Media—Can I Change a Graphic's File Size?", New Perspectives on Computer Concepts-Course Technology, 2011, Cengage Learning, Boston, MA.
Paul H. Perlstein et al., "Computer-Assisted Newborn Intensive Care," Pediatrics, Apr. 1976, pp. 494-501, vol. 57, No. 4, American Academy of Pediatrics, Inc., Evanston, Illinois.
Paul H. Perlstein et al., "Future Directions for Device Design and Infant Management," Medical Instrumentation, Feb. 1987, pp. 36-41, vol. 21, No. 1, Association for the Advancement of Medical Instrumentation.
PCA II Multi-Mode Cartridge Operator's Manual, Sep. 1995, approx. 40 pages, Baxter Healthcare Corporation, Deerfield, IL.
Pesce, James, "Bedside Terminals: Medtake," Clinical Computing, Jan. /Feb. 1988, pp. 16-21, vol. 5, No. 1.
Peter Lord et al., MiniMed Technologies Programmable Implantable Infusion System, Annals New York Academy of Science, pp. 66-71, describing clinical trials from Nov. 1986.
Peterson et al., The North Dakota Telepharmacy Project Restoring and Retaining Pharmacy Services in Rural Communities—Presentation North Dakota State University, Fargo, North Dakota.
Petition for Inter Partes Review *Baxter International Inc.* v. *Becton, Dickinson and Company* for U.S. Pat. No. 8,374,887, pp. 1-69.
Pharmacy Automation Online Vendors Page; Internet Archive Wayback Machine; http://pharmacyautomation.com/vendors.html—3 pages.
Pharmacy Data Management (PDM) Technical Manual/Security Guide Version 1.0, Sep. 1997—55 pages.
Pharmacy education and practice out of sync? (Roundtable) Chain Drug Review, vol. 25, No. 6, Mar. 17, 2003, RX2 (6).
Prem S. Chopra, Virgil A. Thomason, and Dell M. Stinett; "Voice-Activated Networked Workstation for a Physically Disabled Physician," 10-7803-2050-6/94 1994 IEEE, pp. 478-479.
Product literature, Baxter Healthcare Corporation, "Flo-Gard® 6201 Volumetric Infusion Pump," 1992, 2 pages.
Product literature, Baxter Healthcare Corporation, "MultiPlex™ Series 100 Fluid Management System," 1988, 2 pages.
Product literature, Baxter Healthcare Corporation, "MultiPlex™ Series 100 Fluid Management System," undated, 2 pages.
Remote Dispensing Regulations, NABPLAW Sep. 2003.
Woodall, Sandra C., Remote Order Entry and Video Verification; Reducing After-Hours Medication Errors in a Rural Hospital; S. Woodall; Joint Commission on Accreditation of Healthcare Organizations; vol. 30; No. 8; Aug. 2004.
Rich Muller; "NRx QS/1's Premium Pharmacy Software," Insight, the QS/1 Magazine, Jul. 2003; pp. 2-3, 12-15.
Rouse, et al., Academy of Managed Care Pharmacy et al., "White paper on pharmacy technicians 2002: Needed changes can no longer wait" Am J Health-Syst Pharm, Jan. 1, 2003, vol. 60—pp. 37-51.
Rule Section 291.36—Class A Pharmacies Compounding Sterile Pharmaceuticals—1 page.
Schrenker, Richard and Cooper, Todd, "Building the Foundation for Medical Device Plug-and-Play Interoperability".
Seifert et al.; "The Training of a Telepharmacist: Addressing the Needs of Rural West Texas," American Journal of Pharmaceutical Education 2004; 68 (3) Article 60. Jul. 16, 2004.
Standard Specification for Transferring Clinical Laboratory Data Messages Between Independent computer Systems, Annual Book of ASTM Standards, Mar. 25, 1988, pp. 1-16, E 1238-88, Global Engineering Documents, Philadelphia, PA.
Standard Specification for Transferring Clinical Observations Between Independent Computer Systems, Annual Book of ASTM Standards, June Mar. 1994, pp. 132-210, E 1238-94, Philadelphia, PA.
Standard Specification for Transferring Clinical Observations Between Independent Computer Systems, Aug. 10, 1997, 79 pages, ASTM E 1238-97, West Conshohocken, PA, United States.
Standard Specification for Transferring Information Between Clinical Instruments and Computer Systems, Annual Book of ASTM Standards, Jun. 1991, 15 pages, E 1394-91, Philadelphia, PA.
Suzanne Carter, RN, Ed.D. et al., "The Computer-based Patient Record: The Jacobi Medical Center Experience," Second Annual Nicholas E. Davies Award Proceedings of the CPR Recognition Symposium, 1996, pp. 71-95, Computer-based Patient Record Institute, Inc., Bethesda, MD.
T. Allan Pryor et al., "help—A Total Hospital Information System," Proceedings of the Fourth Annual Symposium on Computer Applications in Medical Care, Nov. 2-5, 1980, pp. 3-7, vol. 1, Institute for Electrical and Electronics Engineers, New York, NY.
T.E. Bozeman et al., "The Development and Implementation of a Computer-Based Patient Record in a Rural Integrated Health System," Third Annual Nicholas E. David Award Proceedings of the CPR Recognition Symposium, 1997, pp. 101-130, Computer-based Patient Record Institute, Inc., Bethesda, MD.
"Telepharmacy project expands students' practice experience" Telemedicine Report, vol. 6, No. 1, Jan. 2004 oe 4 pages.
The World's First Fully Integrated Workflow Manager for I.V. Rooms, IntelliFlowRx Brochure, For Health Technologies Inc,. United States, May 2008.
Title 22. Examining Boards, 22 TAC Section 1.161; texinfo.library.unt.edu/Texasregister/html/2001/sep-14/PROPOSED/22.EXAMING BOARDS.html—Sep. 20, 2014, pp. 1-70.
Ukens, Carol, "Pharmacist shortage boosts telepharmacy" Drug Topoics, Jun. 3, 2002; 146, 11—p. 53.
Valeriy Nenov et al., "Remote Analysis of Physiological Data from Neurosurgical ICU Patients," Journal of the American Medical Informatics Association, Sep./Oct. 1996, pp. 318-327, vol. 3, No. 5.
"Victor J. Perini et al., Comparison of automated medication-management systems,: Am. J. Hosp. Pharm., Aug. 1, 1994, pp. 1883-1891, vol. 51, American Society of Hospital Pharmacists, Inc.".
Vincenzo Della Mae et al., "HTML generation and semantic markup for telepathology," Computer Networks and ISDN Systems, 1996, pp. 1085-1094, vol. 28, Elsevier Science B.V.
Website information for Cartharsis Medical Technology Products, Dec. 9, 2001, 15 pages.
Website information for MedPoint™, Mar. 13, 2003, 20 pages, Bridge Medical, Solana Beach, CA.
William R. Dito et al., "Bar codes and the clinical laboratory: adaptation perspectives," Clinical Laboratory Management Review, Jan./Feb. 1992, pp. 72-85, Clinical Laboratory Management Association, Inc.
Wills, Robert D., "Drug Images and Drug Imprints" Insight, Apr. 2001—p. 7.
Yvonne Mari Abdoo, "Designing a Patient Care Medication and Recording System that Uses Bar Code Technology," Computers in Nursing, May/Jun. 1992, pp. 116-120, vol. 10, No. 3.
Jon Phillips, Telepharmacy at Texas Tech, PowerPoint, Jan. 26, 1997, https://web.archive.org/web/20040509162423/http:/www.ttuhsc.edu/telemedicine/Powerpoint/Telepharmacy%20presentation%2042503.ppt.
A.H. McMorris et al. "Are Process Control Rooms Obsolete?", Control Engineering, pp. 42-47, Jul. 1971.
Standard Specification for Transferring Clinical Observations between Independent Computer Systems, Annual Book of ASTM Standards, Nov. 14, 1991, pp. 1-64, ASTM E 1238-91, Philadelphia, PA.
Standard Specification for Transferring Information Between Clinical Instruments and Computer Systems, Dec. 10, 1997; 15 pages, ASTM E 1394-97, West Conshohocken, PA, United States.
Web site information, Information Data Management, Inc.'s PCMS: Plasma Center Management System, Dec. 14, 2001, 11 pages.

(56) References Cited

OTHER PUBLICATIONS

Web site Information, Wyndgate Technologies' SafeTrace Tx™, undated, 15 pages.
Specification for Low-Level Protocol to Transfer Messages Between Clinical Laboratory Instruments and Computer Systems, Mar. 11, 1991; 7 pages, ASTM E 1381-91, Philadelphia, PA, United States.
Atherton, H.D., Dollberg, S., Donnelly, M.M., Perlstein, P. H. Roath, S.B., "Computerized Temperature Control of the Low-Birth-Weight Infant: A 20-Year Retrospective and Future Prospects," Biomedical Instrumentation and Technology, Jul./Aug. 1994, pp. 302-309, vol. 28 No. 4.
Friesdorf, W., Grob-Alltag, F., Konichezky, S., Schwilk, B., Fattroth, A., Fett, P., "Lessons learned while building an integrated ICU workstation," International Journal of Clinical Monitoring and Computing, 1994, pp. 89-97, vol. 11.
Gammon, K., Robinson, K., "Bedside Data System Aids Pharmacy," Computers in Healthcare, Dec. 1988, pp. 35-37, vol. 9 No. 12.
Graseby 3100 Syringe Pump, Graseby Medical Ltd., A Cambridge Electronic Industries Company, England, 2 pages.
Kampmann, J., Lau, G., Kropp, St., Schwarzer, E., Hernandez Sande, C., "Connection of electronic medical devices in ICU according to the standard 'MIB'," International Journal of Clinical Monitoring and Computing, 1991, pp. 163-166, vol. 8.
Angaran, "Telemedicine and telepharmacy: Current status and future implications", Am J Health-Syst Pharm, vol. 56, Jul. 15, 1999 (32 pages).
Carson, Ewart et al., "A Systems Methodology for the Development and Evaluation of a Telematic Home Haemodialysis Service," Proceedings—19th International Conference—IEEE/EMBS Oct. 30-Nov. 2, 1997, Chicago, Illinois, pp. 907-910.
Singapore Written Opinion for related Singapore Application No. 11201707114X; action dated Mar. 5, 2019; (7 pages).
Japanese Office Action for related Japanese Application No. 2017-546118; action dated May 15, 2019; (4 pages).
European Office Action for related European Application No. 16759518.0; action dated Jan. 13, 2020; (7 pages).
Singapore Written Opinion for related Singapore Application No. 11201707114X; report dated May 5, 2020; (7 pages).
Extended European Search Report for related European Application No. 20210407.1; action dated Mar. 5, 2021; (11 pages).
Office Action in JP Application No. 2019-165983, dated Nov. 2, 2020 (4 pages).
Third Australian Examination report for related Australian application No. 2016226164; action dated Jul. 14, 2021; (5 pages).
Japanese Office Action and Denial of Entry of Amendment for related Japanese Application No. 2017-546118; actions dated Aug. 20, 2021; (6 pages).
Singapore Examination Report for related Singapore Application No. 11201707114X; report dated May 14, 2021; (9 pages).
Canadian Office Action for related Canadian Application No. 2,978,455; action dated Feb. 23, 2022; (5 pages).
Notice of Reasons for Refusal for Japanese Patent Application No. 2021204870 dated Feb. 28, 2023.
*Becton, Dickinson and Company*, Appellant v. *Baxter Corporation Englewood*, Appelle, Case No. 2020-1937 Appeal from the United States Patent and Trademark Office, Patent Trial and Appeal Board in No. IPR2019-00119—Decided: May 28, 2021—Document 30 filed May 28, 2021—21 pages.
*Becton, Dickinson and Company*, Petitioner, v. *Baxter Corporation Englewood*, Patent Owner, IPR2019-00212, U.S. Pat. No. 9,474,693 B2 Judgment Final Written Decision Determining All Challenged Claims Unpatentable 35 U.S.C. Section 318(a)—Denying Patent Owner's Revised Motion to Amend to Substitute Claims 20-38 35 U.S.C. Section 318(a)—Denying Petitioner's Motion to Exclude Evidence 37 C.F.R. Section 42.64—Paper No. 63 dated Apr. 29, 2020—102 pages.
*Becton, Dickinson and Company*, Petitioner, v. *Baxter Corporation Englewood*, Patent Owner, IPR2019-00119, U.S. Pat. No. 8,554,579 B2 Judgment Final Written Decision Determining No. Challenged Claims Unpatentable 35 U.S.C. Section 318(a)—Denying Petitioner's Motion to Exclude Evidence 37 C.F.R. Section 42.64, Paper 51 entered Apr. 29, 2020—63 pages.
*Baxter Corporation Englewood*, Appellant v. *Becton, Dickinson and Company*, Appellee, Case Nos. 2020-1806, 2020, 1808, Judgment Document 40 filed/entered Mar. 8, 2021 IPR2019-00120, IPR2019-00212 *Baxter Corporation Englewood*, Appellant v. *Becton, Dickinson and Company*, Appellee, Case Nod. 2020-1806, 2020, 1808, Mandate entered Mar. 8, 2021 Document 43, filed May 17, 2021 IPR2019-00120, IPR2019-00212.
*Becton, Dickinson and Company*, Petitioner, v. *Baxter Corporation Englewood*, Patent Owner, IPR2019-00120 U.S. Pat. No. 9,662,273 B2 Judgement Final Written Decision Determining Challenged Claims Unpatentable 35 U.S.C. Section 318 (a)—Denying Patent Owner's Revised Motion to Amend to Substitute Claims 22-42 35 U.S.C. Section 318(a) Denying Petitioner's Motion to Exclude Evidence 37 C.F.R. Section 42.64—Paper 63 dated Apr. 29, 2020, 90 pages.
*Baxter Corporation Englewood*, Appellant v. *Becton, Dickinson and Company*, Appellee, Case Nos. 2020-1806, 2020-1808 IPR2019-00120-IPR2019-0012, On Petition for Rehearing En Banc, Order—Document 42, filed May 10, 2021—2 pages.
*Baxter Corporation Englewood*, Appellant, v. *Becton, Dickinson and Company*, Appellee, Case Nos. 20-1806, 20-1808 Inter Partes Review Nos. IPR2019-00120, IPR2019-00121—Petition for Rehearing En Banc By Appellant Baxter Corporation Englewood—Document 41, filed Apr. 7, 2021—18 pages.
Inter Partes Review Certificate, Ranalletta et al. U.S. Pat. No. 9,662,273 K1 Certificate issued Dec. 30, 2021—2 pages.
Inter Partes Review Certificate, Tribble et al. U.S. Pat. No. 8,554,579 K1 Certificate issued May 12, 2022—2 pages.

* cited by examiner

PHARMACY WORKFLOW MANAGEMENT WITH INTEGRATED ALERTS

RELATED APPLICATIONS

This application relates to and incorporates by reference the co-owned application having Provisional Ser. No. 62/127,580 by Crooks et al. filed on Mar. 3, 2015 entitled PHARMACY WORKFLOW MANAGEMENT WITH INTEGRATED ALERTS.

BACKGROUND

Pharmacies often are relied upon to provide compounded sterile products (CSPs) in connection with the provision of healthcare to patients. Such CSPs may comprise medication doses (sometimes referred to herein simply as doses) that are to be used in connection with the provision of healthcare. In this regard, pharmacies (e.g., including hospital pharmacies, outpatient pharmacies, compounding centers, and the like) often prepare CSPs or doses for delivery to a healthcare provider. Such CSPs may be patient specific doses or be provided for stock or inventory doses in the pharmacy that are compounded in anticipation of use. Accordingly, pharmacy technicians are often tasked with preparation of CSPs under the guidance and supervision of a licensed pharmacist or the like. For instance, a pharmacy technician may, under the supervision of a pharmacist, reconstitute drugs, draw specific drug amounts, gather products, assemble products, and create specific CSPs using reconstituted drugs, products, or the like.

In connection with the preparation of CSPs, pharmacies have begun to introduce an increasing amount of technology to assist in the compounding process. One such example of a technology-assisted compounding system comprises pharmacy workflow management applications that may be executed at pharmacy workstations for use in preparation of CSPs. Such pharmacy workflow management applications may provide assistance to pharmacists and pharmacy technicians in a multitude of areas related to management and preparation of doses. For instance, pharmacy workflow management applications may assist in organizing and managing orders for CSPs or doses (referred to herein as "dose orders") for efficient and timely preparation of doses. Furthermore, such pharmacy workflow management applications may facilitate documentation of the preparation of a dose. Such documentation may be used to audit preparation steps after the fact for, for example, pharmacist review or in connection with tracking regulatory compliance. Such pharmacy workflow management applications may also assist in tracking doses in relation to movement of the dose within the pharmacy, dispensation from the pharmacy, or even movement through a facility, such as to an administration site.

Pharmacy workflow management applications or other technology-assisted approaches to compounding provide the potential benefit of reduction of errors in the pharmacy. For instance, recognizing an error before it occurs or catching the error prior to dispensation of the pharmacy may lead to reduced patient risk associated with human errors that may occur in the pharmacy. Given the potential to improve patient safety in connection with pharmacy activities, it may be appreciated that the facilities provided by technology-assisted approaches to pharmacy work may advantageously be extended by additional capabilities.

SUMMARY

In view of the foregoing, it has been recognized herein that improvement to technology-assisted compounding tools such as pharmacy workflow management applications or the like may assist in reduction of risk to patients by incorporation of medical information from additional sources (e.g., including potentially sources external to the pharmacy). That is, while pharmacy workflow management applications have been associated with the potential to reduce errors that occur in the pharmacy, prior inability or limited ability to integrate data from additional medical sources (e.g., that may be external to the pharmacy) may in turn limit the ability of such an application to provide meaningful assistance outside the context of pharmacy activities. Given the potential benefits derived from a wider perspective of data integration, it is presently recognized that benefits may be provided in connection with integration of additional data sources beyond data sources with a limited perspective of pharmacy-centric information.

Specifically, it is presently recognized that data aggregated from a plurality of sources may be beneficially accessed and/or utilized at a pharmacy workflow management application to, for example, provide useful information to a user when preparing a dose or to a pharmacist when reviewing a dose. For instance, aggregation of data sources may allow alert data to be generated by one or more alert generation platforms. This alert data may be generated at least in part in view of data sources external to the pharmacy. For example, one such contemplated alert generation platform comprises the ICNet™ Suite of alert products provided by ICNet International Limited. Specifically, such alert platforms may comprise software, firmware, and/or hardware components that may be in operative communication with a number of data sources. In turn, the alert generation platform may extract meaningful and actionable data from the underlying data sources to generate alert data in one or more contexts. That is, the alert generation platform may include logic for processing data from one or more sources to generate alert data. For example, alert data may be provided in the context of infection control, antimicrobial stewardship, or other areas. In any regard, this alert data may provide meaningful and actionable information that may assist a pharmacist or pharmacist technician in relation to pharmacy work (e.g., in relation to management and/or preparation of doses, CSPs, or the like). In other embodiments, an information aggregator may be provided that aggregates information from one or more medical information sources for use by, or presentation at, a pharmacy workflow management application (e.g., in the absence of alert data).

In this regard, the present disclosure contemplates the integration of alert data in technology-assisted compounding techniques. Specifically, an interface is contemplated that may provide operative communication between a pharmacy workstation (e.g., that may execute a pharmacy workflow management application) and an alert generation platform. In turn, the pharmacy workstation may be operative to process alert data of the alert generation platform for use in connection with the pharmacy workflow management application that may be executed at the pharmacy workstation. For instance, the alert data may be used to provide an alert indication to a user of the pharmacy workflow management application. Additionally, the alert indication may provide interactive features that may facilitate functionality that is provided to the user of the pharmacy workflow management application. For example, a user of the pharmacy workflow management application having alert data integration may be capable of accessing an instance of the alert generation platform from the pharmacy workflow management application. In turn, the pharmacist or pharmacy technician's workflow may be simplified such that the access to alert data and/or the alert generation platform may be made more efficient by providing direct access by way of the pharmacy workflow management application.

Additionally, the interface may facilitate bidirectional communication between the pharmacy workstation and the alert generation platform. In turn, information may be exchanged between the pharmacy workstation and the alert generation platform. One such example may include proving a responsive input received from a user of the pharmacy workflow management application to the alert generation platform. Accordingly, the alert generation platform may include resolution information and/or intervention information that may, for example, provide an indication of a response by appropriate personnel to an alert and/or an outcome of the response to the alert. As such, rather than having to separately access the alert generation platform to provide such a responsive input or duplicate the input of such input in multiple platforms, the input may be provided directly to the pharmacy workflow management application executing on a pharmacy workstation such that the responsive input is in turn provided to the alert platform. In turn, responsive inputs such as alert interventions may be communicated in bidirectional fashion between the pharmacy workstation and the alert generation platform.

Additionally, the pharmacy workflow management application may include logic that allows for dose order record manipulation within the pharmacy workflow management application in response to alert data of the alert generation platform. In this regard, dose orders received at a pharmacy may be processed to generate dose order records that may be reflected in the pharmacy workflow management application. For instance, dose order records may be assigned a status by the pharmacy workflow management application and may be presented to a user in a dose order listing. Accordingly, upon receipt of alert data, the pharmacy workflow management application may be capable of processing the alert data in connection with one or more dose order records to take action in relation to a dose order record based on the alert data. For instance, a dose order record may have a status changed, may be displayed in a different manner, may be displayed in a different interface portion of the pharmacy workflow management application, or have some other appropriate action taken in relation to a dose order record in response to the alert data.

Further features may be facilitated by the integration of alert data in a pharmacy workflow management application. For instance, a user of the pharmacy workflow management application may be capable of accessing a local instance of the alert generation platform directly from the interface of the pharmacy workflow management application. As such, the local instance of the alert generation platform may be executed on the pharmacy workstation on which the pharmacy workflow management application is also executed. As may be further appreciated, the local instance of the alert generation platform may be executed in connection with a thin client such as an internet browser such that access to an alert generation platform remote from the pharmacy workstation on which the pharmacy workflow management application is executed may be provided by way of the thin client. Furthermore, access to features of the alert generation platform (e.g., including reporting functionality) may be directly accessed by a user of the pharmacy workflow management application. Further still, additional capabilities provided by certain configurations of a pharmacy workflow management application may facilitate additional functionality in relation to the integration. For instance, a pharmacy workflow management application may be executed in a distributed environment where a plurality of pharmacy workstations may be operative to execute the pharmacy workflow management application. In this case, each of the distributed pharmacy workstations may have access to alert data that is processed once received from an alert generation platform. Furthermore, in at least some embodiments, central server communication used by the pharmacy workflow management application may also be used to provide functionality in connection with the alert data. For instance, alert data, alert indications, alert responses, alert interventions, or other information may be provided to a central server in connection with a backup, a data analytics tool, and/or report generation tool provided in connection with a central server. In this regard, the central server may be in communication with a plurality of local facilities each executing a pharmacy workflow management application. As such, the data received from the plurality of local facilities may be aggregated such that large scale trends in relation to alert data may be identified (e.g., including antimicrobial behaviors at a wide scale such as drug resistances or infection control at a wide scale).

Further still, embodiments are contemplated herein where aggregated medical information may be presented to a user of a pharmacy workflow management application. For example, the aggregated medical information may be collected at an information aggregator (e.g., which may or may not also provide alert generation capability). That is, an alert generation module may aggregate data both for presentation in raw form and for processing to generate alert data therefrom. In any regard, the aggregated medical information may be presented to a user of a pharmacy workflow management application. For instance, aggregated information may be presented to a user of the pharmacy workflow management application prior to preparation of a dose. Further still, aggregated medical information may be presented in connection with preparation of a dose. Additionally or alternatively, aggregated medical information may be presented to a user of the pharmacy workflow management application during approval and/or review of a prepared dose. In this regard, the aggregated medical information may be provided in connection with alert data provide to the pharmacy workflow management application or may be provided in the absence of an alert.

Accordingly, a first aspect comprises a pharmacy workstation for use in connection with execution of a pharmacy workflow management application. The pharmacy workstation includes a memory storing the pharmacy workflow management application and a processor configured to access the pharmacy workflow management application stored in the memory to execute the pharmacy workflow management application. The pharmacy workstation also includes an interface in operative communication with the processor and an alert generation platform. The processor is operative to process alert data of the alert generation platform from the interface and is operable to configure a display to present an alert indication corresponding to at least a portion of the alert data to the user at the pharmacy management workstation in connection with the pharmacy workflow management application.

A number of feature refinements and additional features are applicable to the first aspect. These feature refinements and additional features may be used individually or in any combination. As such, each of the following features that will be discussed may be, but are not required to be, used with any other feature or combination of features of the first aspect.

For example, in an embodiment the alert indication may be displayed at a user interface of the pharmacy workstation presented on the display. Furthermore, the user interface of the pharmacy workstation may further include an input device. As such, the user interface may include an interactive portion corresponding to the alert indication. In an embodiment, the alert indication may include the interactive portion. The alert indication may be provided on a user interface screen of the pharmacy workflow management application corresponding to a pharmacist workspace comprising a listing of dose orders of the pharmacy workflow management application. Additionally or alternatively, the alert indication may be provided on a user interface screen of the pharmacy workflow management application corresponding to an interface for pharmacist verification of a dose order. The alert indication may provide information regarding the nature of the alert and/or action items to be taken in response to the alert indication. The alert may be highlighted in the user interface based upon the nature of the alert (e.g., with important, urgent, or critical alert indications appearing in a different color to highlight the alert relative to lower priority alerts).

The interactive portion may facilitate a number of functionalities within the pharmacy workflow management application. For example, the interactive portion, upon selection by a user by way of an input provided using the input device, may configure the processor at the pharmacy workstation to launch execution of the alert generation platform at the pharmacy workstation. For instance, selection of the interactive portion may launch a local instance of the alert generation platform at the pharmacy workstation executing the pharmacy workflow management application. The local instance may be a local instance of the alert generation platform or may be a thin client operative to present an interface regarding a remotely executed alert generation platform.

The pharmacy workstation may also include a dose processing interface for receipt of dose order data of an order entry system. The order entry system may comprise a portion of a hospital information system, a pharmacy information system, or other appropriate electronic medical record system. The dose order data may include medication data regarding at least one dose order for administration in connection with provision of medical care. For at least some dose orders, the dose order data may include patient data or other EMR data as well. The at least one dose order may be populated into a dose order listing displayed at the display of the user interface of the pharmacy workstation. In turn, the processor may be operative to process the alert data of the alert generation platform from the interface in relation to the dose order listing to associate the alert indication with one or more corresponding respective dose order in the dose order listing.

For instance, in an embodiment, the alert data may include patient specific alert data. For instance, the alert data may relate to a specific lab result for a given patient, a specific treatment undertaken for a specific patient, specific patient allergies, or other patient related information. As such, the alert data may include a first patient identifier corresponding to a patient to whom the alert data applies. The dose order data may include a second patient identifier corresponding to a patient to whom the dose order is to be administered. Correspondence of the first patient identifier and the second patient identifier may result in the alert data being associated to the dose order. In turn, the alert indication may be displayed on the user interface at the pharmacy workstation in connection with a dose order for the patient to whom the alert data is associated. For instance, the first patient identifier and the second patient identifier may be identical or correlated in some fashion (e.g., a look-up table or the like) to associate the alert indication with the patient specific dose order. As such, the alert indication may be provided in corresponding relation to the dose order in the pharmacy workflow management application.

In further regard to alert generation platform functionality provided at the pharmacy workflow management application, the dose order listing may include at least one patient specific order and the user interface comprises a patient link that, upon selection by a user by way of an input provided using the input device, may configure the processor to launch execution of a local instance of the alert generation platform at the pharmacy workstation to display a patient report corresponding to the patient associated with the at least one patient specific dose order from the alert generation platform in connection with the pharmacy workflow management application. The patient report may provide details regarding the patient that may, for example, be presented in a timeline format reflecting major events in relation to the patient's care such as use of medical devices, order or administration of drugs, laboratory results, procedures, vital signs, or other patient related information.

Further still, the input device may be configured to receive a responsive input from a user of the pharmacy workflow management application corresponding to a response to the alert indication. For instance, the responsive input may comprise an intervention and/or outcome related to an alert indication presented at the pharmacy workstation. The interface may be in bidirectional communication with the alert generation platform to provide the responsive input to the alert generation platform. The responsive input may include instructions for modification of a corresponding dose order associated with the alert indication.

In an embodiment, the memory may include alert processing rules accessible by the processor for processing the alert data received at the interface by the processor. For instance, the alert processing rules may define one or more triggering conditions for presentation of the alert indication in the pharmacy workflow management application. Accordingly, upon satisfaction of the one or more triggering conditions (e.g., only upon satisfaction of the one or more triggering conditions), the alert indication may be displayed in corresponding relation to one or more dose orders in a dose order listing of the pharmacy workflow management application.

Additionally or alternatively, the alert processing rules may define one or more actions to be taken with respect to a given dose order in response to the alert indication. Upon satisfaction of the one or more triggering conditions, the processor may be operative to execute the one or more actions with respect to the given dose order in response to the alert indication. The action by the processor may occur automatically upon satisfaction of the triggering condition such that no user input is needed to complete the action for the dose order. The one or more actions to be taken with respect to a given dose order may include modification of a status of the given dose order in the dose order listing of the pharmacy workflow management application. Additionally, the pharmacy workflow management application may include a user interface screen for displaying one or more given dose orders for which one or more actions have been taken in response to one or more corresponding alert indications. For example, a dose order listing filter may be provided that filters a dose order listing to show only those dose orders for which a particular action has been taken in response to satisfaction of a triggering condition by an alert indication.

In an embodiment, the interface may be in bidirectional communication with the alert generation platform. As such, the pharmacy workstation may locally present at the pharmacy workstation information from the alert generation platform. The processor may be operative to configure the display to present report data in connection with the pharmacy workflow management application that is received from the alert generation platform (e.g., in response to a request for the report data from the pharmacy workstation). Additionally, in an embodiment, the pharmacy workstation may be in operative communication with a server remote from the pharmacy workstation. Accordingly, the processor may be in operative communication with the server for communication of the alert data to the server such that the server may store a copy of the alert data in a server memory located at the server. The server remote from the pharmacy workstation may be a pharmacy workflow management server specific to the facility at which the pharmacy workflow management application is executed or may be a central server remote from the facility to which a plurality of pharmacy workflow management applications at different respective facilities communicate information.

While the alert generation platform may be operative to acquire and/or process data from a plurality of medical information sources to provide alert data in a number of contexts, in the specific context of a pharmacy a number of specific alert types may be particularly of interest. For instance, the alert data may include information related to at least one of infection control or antimicrobial stewardship. For instance, alerts associated with given microbial organisms identified in a patient may trigger an alert or may trigger alerts in respect of particular medications ordered for a patient. Furthermore, identification of particular infections may provide alert data in the pharmacy.

Furthermore, the processor of the pharmacy workstation may be operative to process aggregated medical information received from an information aggregator so that the processor may configure a display to present at least a portion of the aggregated medical information to a user at the pharmacy workstation in connection with the pharmacy workflow management application. For instance, the aggregated medical information may correspond to aggregated information regarding a particular patient (e.g., a patient for whom a dose order has been received at the pharmacy workflow management application). Additionally or alternatively, the aggregated medical information may include information regarding a plurality of patients. The aggregated medical information may also relate to a given facility or a collection of facilities. The aggregated medical information may be displayed independently within the pharmacy workflow management application (e.g., in the form of a report or the like), in connection with a dose order record listing, or in connection with a review screen presented during review and/or approval of a dose order.

A second aspect includes a non-transitory computer readable medium comprising computer-readable instructions for configuration of a processor to execute a pharmacy workflow management application and process alert data of an alert generation platform. The computer-readable instructions may further configure the processor to configure a display to present an alert indication corresponding to at least a portion of the alert data to a user of the pharmacy workflow management application in connection with the pharmacy workflow management application.

A number of feature refinements and additional features are applicable to the second aspect. These feature refinements and additional features may be used individually or in any combination. As such, each of the following features that will be discussed may be, but are not required to be, used with any other feature or combination of features of the second aspect. Additionally, any of the features or feature refinements discussed above in relation to the first aspect may be, but are not required to be, used with any other feature or combination of features of the second aspect.

In an embodiment, the computer-readable instructions may configure the processor to display the alert indication at a user interface of the pharmacy workstation on the display. Additionally, the computer-readable instructions may configure the processor to display on the user interface an interactive portion corresponding to the alert indication. In an embodiment, the alert indication may include the interactive portion. As such, the computer-readable instructions may configure the processor to launch execution of the alert generation platform at a pharmacy workstation upon receipt of a selection of the interactive portion by a user (e.g., by way of a user input at the pharmacy workstation).

In an embodiment, the computer-readable instructions may configure the processor to provide the alert indication on a user interface screen of the pharmacy workflow management application corresponding to a pharmacist workspace comprising a listing of dose orders of the pharmacy workflow management application. Additionally or alternatively, the computer-readable instructions configure the processor to provide the alert indication on a user interface screen of the pharmacy workflow management application corresponding to an interface for pharmacist verification of a dose order.

In an embodiment, the non-transitory computer readable medium may further include computer-readable instructions for configuration of the processor to execute a dose processing interface for receipt of dose order data of an order entry system. The dose order data may include medication data regarding at least one dose order for administration in connection with provision of medical care. As such, the computer-readable instructions may configure the processor to populate at least one dose order into a dose order listing displayed at the display of the user interface of the pharmacy workstation. Specifically, the computer-readable instructions may configure the processor to process the alert data of the alert generation platform from the interface in relation to the dose order listing to associate the alert indication with one or more corresponding respective dose orders in the dose order listing.

In an embodiment, the alert data may include patient specific alert data. For instance, the alert data may include a first patient identifier corresponding to a patient to whom the alert data applies, and the dose order data may comprise a second patient identifier corresponding to a patient to whom the dose order is to be administered. The computer-readable instructions may configure the processor to determine correspondence of the first patient identifier and the second patient identifier and associate the alert data to the dose order based on the correspondence. As described above, the first and second patient identifiers may be identical or associated (e.g., in a correlation table or the like). As such, the dose order listing may include at least one patient specific order and the computer-readable instructions may configure the processor to provide a patient link at the user interface that, upon selection by a user by way of an input provided using an input device, further configures the processor to launch execution of the alert generation platform (e.g., a local instance of the alert generation platform) at the pharmacy workstation to display a patient report corresponding to the patient associated with the at least one patient specific dose order from the alert generation platform in connection with the pharmacy workflow management application.

In an embodiment, the computer-readable instructions may configure the processor to provide the alert indication in corresponding relation to a dose order in the pharmacy workflow management application. Additionally, the computer-readable instructions may configure the processor to receive a responsive input from a user of the pharmacy workflow management application corresponding to a response to the alert indication. The computer-readable instructions may configure the processor to communicate with the alert generation platform to provide the responsive input to the alert generation platform. In an embodiment, the responsive input comprises instructions for modification of a corresponding dose order associated with the alert indication.

The computer-readable instructions may include alert processing rules accessible by the processor for processing the alert data received at the interface. The alert processing rules may define one or more triggering conditions for presentation of the alert indication in the pharmacy workflow management application. Upon satisfaction of the one or more triggering conditions, the computer-readable instructions may configure the processor to display the alert indication in corresponding relation to one or more dose orders in a dose order listing of the pharmacy workflow management application. The alert processing rules may define one or more actions to be taken with respect to a given dose order in response to the alert indication. As such, upon satisfaction of the one or more triggering conditions, the computer-readable instructions may configure the processor to execute the one or more actions with respect to the given dose order in response to the alert indication. For instance, the one or more actions to be taken with respect to a given dose order may include modification of a status of the given dose order in the dose order listing of the pharmacy workflow management application. Further still, the computer-readable instructions may configure the processor to display a user interface screen for displaying one or more given dose orders for which one or more actions have been taken in response to one or more corresponding alert indications by the pharmacy workflow management application.

In an embodiment, the computer-readable instructions may configure the processor to communicate with the alert generation platform. As such, the processor may be operative to configure the display to present report data in connection with the pharmacy workflow management application that is received from the alert generation platform in response to a request for the report data from the pharmacy workstation. The report data may be presented locally at a pharmacy workstation executing the computer-readable instructions. The computer-readable instructions may also configure the processor of the pharmacy workstation to communicate with a server remote from the pharmacy workstation. The computer-readable instructions may configure the processor to communicate with the server for communication of the alert data to the server. In turn, the server may store a copy of the alert data in a server memory located at the server.

In an embodiment, the alert data may include information related to at least one of infection control or antimicrobial stewardship. As described above, the alert data may be generated by the alert generation platform based on a number of medical information sources. Specifically, the alert generation platform may apply logic to the medical information received from the various sources to identify trends, patterns, or the like from the data regarding antimicrobial stewardship and/or infection control.

A third aspect includes a method for pharmacy workflow management. The method includes executing a pharmacy workflow management application and processing alert data of an alert generation platform. The method further includes configuring a display to present an alert indication corresponding to at least a portion of the alert data to a user of the pharmacy workflow management application in connection with the pharmacy workflow management application.

A number of feature refinements and additional features are applicable to the third aspect. These feature refinements and additional features may be used individually or in any combination. As such, each of the following features that will be discussed may be, but are not required to be, used with any other feature or combination of features of the third aspect. Additionally, any of the foregoing features described in connection with the first and/or second aspects may be, but are not required to be, used with any other feature or combination of features of the third aspect.

For instance, in an embodiment the method includes displaying the alert indication at a user interface of the pharmacy workstation presented on the display. The user interface may further include an input device. As such, the user interface may also include an interactive portion corresponding to the alert indication. For example, the alert indication may include the interactive portion.

In an embodiment, the method may include providing the alert indication on a user interface screen of the pharmacy workflow management application corresponding to a pharmacist workspace comprising a listing of dose orders of the pharmacy workflow management application. Additionally or alternatively, the method may include providing the alert indication on a user interface screen of the pharmacy workflow management application corresponding to an interface for pharmacist verification of a dose order.

The method may include a number of actions with respect to the interactive portion. For instance, the method may include launching, by the processor, execution of the alert generation platform at the pharmacy workstation upon selection of the interactive portion by a user by way of an input provided using the input device.

In an embodiment, the method may include executing a dose processing interface for receipt of dose order data of an order entry system. The dose order data may include medication data regarding at least one dose order for administration in connection with provision of medical care. The method may further include populating the at least one dose order into a dose order listing displayed at the display of the user interface of the pharmacy workstation. The method may also include processing, using the processor, the alert data of the alert generation platform from the interface in relation to the dose order listing to associate the alert indication with one or more corresponding respective dose order in the dose order listing.

For example, in an embodiment, the alert data may include patient specific alert data. As such, the alert data may include a first patient identifier corresponding to a patient to whom the alert data applies and the dose order data may include a second patient identifier corresponding to a patient to whom the dose order is to be administered. In turn, correspondence of the first patient identifier and the second patient identifier may result in the alert data being associated to the dose order. The correspondence may be identical patient identifiers or otherwise associable patient identifiers to identify a given patient.

In this regard, the dose order listing may include at least one patient specific order and the user interface may include a patient link. The method may further include launching alert generation platform at the pharmacy workstation upon selection by a user by way of an input provided using the input device to display a patient report corresponding to the patient associated with the at least one patient specific dose order from the alert generation platform in connection with the pharmacy workflow management application.

In an embodiment, the method may include providing the alert indication in corresponding relation to the dose order in the pharmacy workflow management application. The method may further include receiving a responsive input from a user of the pharmacy workflow management application corresponding to a response to the alert indication. For instance, the responsive input may comprise an intervention or outcome relative to an alert. The method may further include communicating with the alert generation platform to provide the responsive input to the alert generation platform. In an embodiment, the responsive input comprises instructions for modification of a corresponding dose order associated with the alert indication.

In an embodiment the method may include applying alert processing rules accessible by the processor for processing the alert data received at the interface. The alert processing rules may define one or more triggering conditions for presentation of the alert indication in the pharmacy workflow management application. As such, upon satisfaction of the one or more triggering conditions, the method may further include displaying the alert indication in corresponding relation to one or more dose orders in a dose order listing of the pharmacy workflow management application. The alert processing rules may define one or more actions to be taken with respect to a given dose order in response to the alert indication. As such, upon satisfaction of the one or more triggering conditions, the method may further include executing the one or more actions with respect to the given dose order in response to the alert indication. As such, the method may include status of the given dose order in the dose order listing of the pharmacy workflow management application based on the alert indication. The method may also additionally include displaying one or more given dose orders for which one or more actions have been taken in response to one or more corresponding alert indications at a user interface screen of the pharmacy workflow management application.

In an embodiment, the method may include configuring the display to present report data in connection with the pharmacy workflow management application that is received from the alert generation platform in response to a request for the report data from the pharmacy workstation. Further still, the method may include communicating the alert data to a server remote from the pharmacy workstation, wherein the server stores a copy of the alert data in a server memory located at the server. Also, as described above, the alert data may include information related to at least one of infection control or antimicrobial stewardship.

A fourth aspect includes a pharmacy workstation for use in connection with execution of a pharmacy workflow management application. The pharmacy workstation includes a memory storing the pharmacy workflow management application and a processor configured to access the pharmacy workflow management application stored in the memory to execute the pharmacy workflow management application. The pharmacy workstation may further include an alert generation module executable by the processor to configure the processor to communicate with one or more healthcare information sources and to generate alert data based at least in part on healthcare data of the one or more healthcare information sources. The alert generation module may be operative to process the alert data and configure a display to present an alert indication corresponding to at least a portion of the alert data to the user at the pharmacy management workstation in connection with the pharmacy workflow management application.

A number of feature refinements and additional features are applicable to the fourth aspect. These feature refinements and additional features may be used individually or in any combination. As such, each of the features discussed above in connection with any of the foregoing aspects, but in particular the first aspect, may be, but are not required to be, used with any other feature or combination of features of the fourth aspect.

A fifth aspect includes a medical information processing system for exchange of medical information. The medical information processing system may include a medical information processing platform comprising at least one processor configured for receipt and distribution of medical information. The medial information processing system may further include one or more exchange interfaces executed by the medical information processing platform that are in operative communication with a plurality of medical information sources each configured to store digital medical information and operable to communicate the digital medical information with the medical information processing platform by way of the one or more exchange interfaces. The medical information processing system may further include a memory at the medical information processing platform configured for storage of the digital medical information received from the plurality of medical information sources. The memory may include a formulary for use in the provision of medical care, and wherein the formulary reflects information regarding the digital medical information received from the plurality of medication information sources.

A number of feature refinements and additional features are applicable to the fifth aspect. These feature refinements and additional features may be used individually or in any combination. As such, the following features may be, but are not required to be, used with any other feature or combination of features of the first aspect. For instance, in an embodiment of the medical information processing system a first of the plurality of medical information sources may include an alert generation platform and a second of the plurality of medical information sources may include a pharmacy workstation. In this embodiment of the system, any of the foregoing features described in connection with the above aspects may be, but are not required to be, used with any other feature or combination of features with the fifth aspect.

BRIEF DESCRIPTION OF THE DRAWINGS

FIG. 13 depicts an interface of a pharmacy workflow management application for configuration of alert data processing at the pharmacy workflow management application.

FIG. 14 depicts embodiments of interfaces for display of filtered alert indication listings.

FIG. 15 depicts a dose order detail screen depicting action history in respect to the dose order.

DETAILED DESCRIPTION

Figure 1:
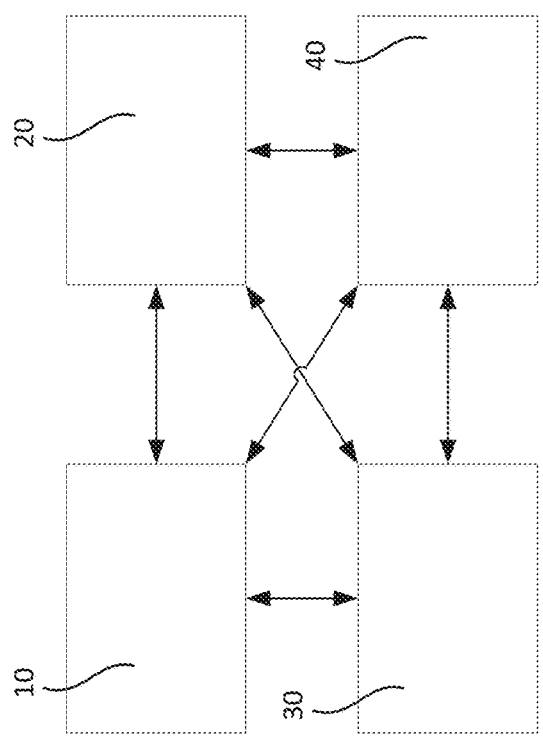
FIG. 1 depicts a schematic view of an approach for medical information exchange.

While the invention is susceptible to various modifications and alternative forms, specific embodiments thereof have been shown by way of example in the drawings and are herein described in detail. It should be understood, however, that it is not intended to limit the invention to the particular form disclosed, but rather, the invention is to cover all modifications, equivalents, and alternatives falling within the scope of the invention as defined by the claims.

As described above, the use of technology-assisted preparation of doses has been used as a mechanism by which to help reduce the risk of committing errors during the compounding of doses in a pharmacy or the like. In this regard, such technology-assisted approaches such as the use of a pharmacy workflow management application or the like may leverage information to assist in identifying errors and risks to patients. For instance, formulary information in combination with dose order information and information related to scanned products and drugs during preparation may provide a pharmacist or pharmacy technician insight that is useful when preparing doses. However, to date the information that may be utilized has generally been primarily limited to information that is maintained within the pharmacy (e.g., wholly stored by a pharmacy workflow management application or the like) with limited or no ability to integrate data from other sources.

In turn, it is herein recognized that the exchange of medical information between sources of medical information may advantageously be leveraged to reduce patient risk, thereby potentially improving patient outcomes. However, with the desire to exchange medical information comes complications associated with the exchange. One such issue is illustrated in FIG. 1. FIG. 1 depicts a first medical information source 10, a second medical information source 20, a third medical information source 30, and a fourth medical information source 40. In approaching exchange of data between medial information sources 10-40, one potential paradigm would be to provide individual exchange paths (represented in FIG. 1 as arrowed lines connecting the sources) between each respective one of the medical information sources 10-40. However, such an approach provides additional complexity in that each individual data exchange between every given medical source must be individually managed. For instance, if an exchange protocol for a given source (e.g., medical information source 40) is altered, each other source (e.g., source 10, source 20, and source 40) must each account for the change in protocol. That is, each individual exchange path must be modified, thus leading to additional complexity and cost in connection with the information exchange. For example, the medical information sources 10-40 may each be provided by different respective entities such that collaboration in relation to changes may be difficult.

Figure 2:
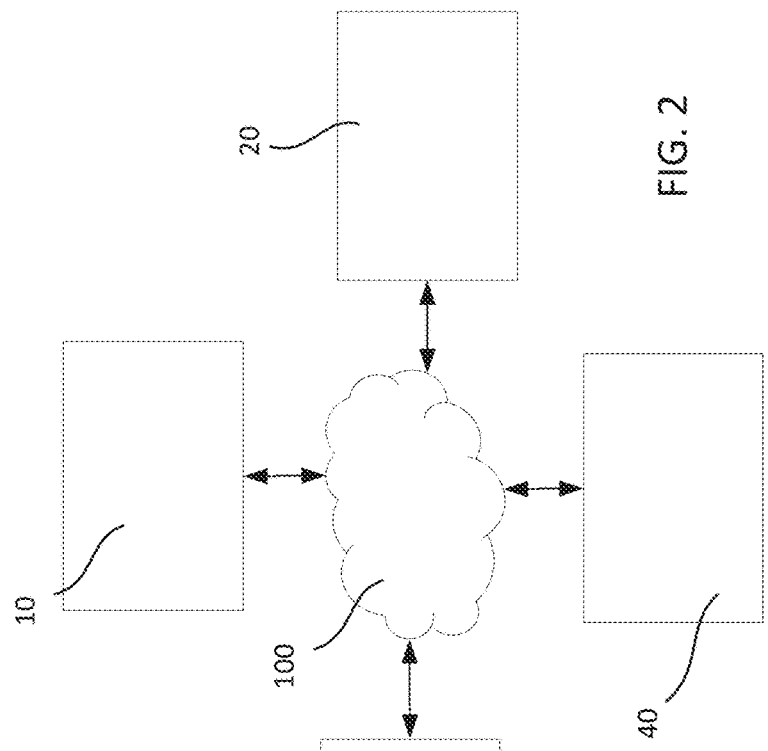
FIG. 2 depicts a schematic view of an approach for medical information exchange using a medical information processing platform.

In contrast, FIG. 2 shows depicts a number of medical information sources (i.e., a first medical information source 10, a second medical information source 20, a third medical information source 30, and a fourth medical information source 40) that are each in communication with a medical information processing platform 100. The medical information processing platform 100 may in turn manage the exchange of information between various ones of the medical information sources 10-40. Accordingly, the medical information processing platform 100 may facilitate cross-source data exchange such that the exchange of data between any or all of the various sources 10-40 may be made more efficiently. For instance, in the event the exchange protocol for a source (e.g., medical information source 40) is altered, only the exchange between the medical information processing platform 100 may be modified to accommodate for the change, while the remainder of the sources are unchanged. In turn, the medial information processing platform 100 may provide a robust, efficient, and scalable exchange platform for exchange of data between sources even when the data formats and exchange protocols differ between the various sources.

Figure 3:
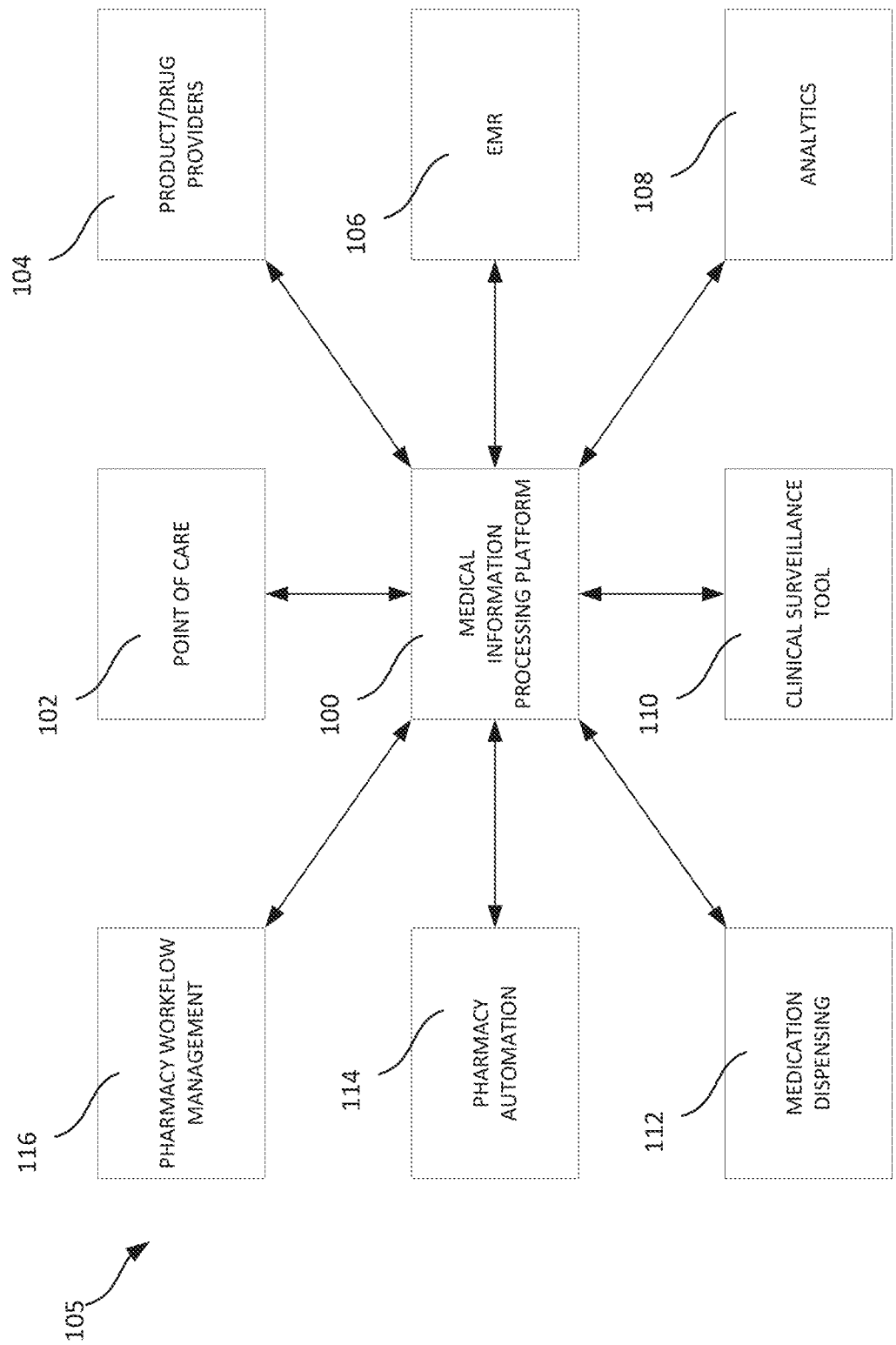
FIG. 3 depicts an embodiment of an approach for medical information exchange using a medical information processing platform with specific examples of medical information sources.

Accordingly, given the architecture facilitated by way of the medical information processing platform 100, a variety of medical information sources have the potential to be operatively engaged for exchange of information. In this regard, with improved data exchange, additional patient safeguards, production efficiencies, product optimizations, or other benefits may be realized as will be appreciated from the continued discussion below. FIG. 3 depicts one environment of a medication information processing system 105 that demonstrates the potential benefit of employing a medical information processing platform 100 to facilitate data exchange.

For instance, FIG. 3 provides a few examples of potential medical information sources that may be in communication with a medical information processing platform 100 to facilitate exchange of medical information. In this regard, FIG. 3 depicts one or more point of care devices 102 that may be in operative communication with the medical information processing platform 100. The point of care device 102 may, for example, include an administration device such as an infusion pump or the like that may provide information about a patient and/or administration parameters to the medical information processing platform 100. The point of care device 102 may further include workstations at the point of care (e.g., bedside terminals or the like) that may provide information to the medical information processing platform 102.

The medical information processing platform 100 may also be in operative communication with one or more product or drug providers 104. For instance, the product or drug providers 104 may provide information regarding available drugs and products including, for example, information regarding national drug codes (NDCs), recall information, new product information, or the like.

One or more electronic medical record (EMR) systems 106 may also be in operative communication with the medical information processing platform 100. The EMR system 106 may comprise a hospital information system (HIS) or a pharmacy information system (PhIS). For instance, the EMR system 106 may provide patient admission/discharge information, patient identifier information, information regarding facility resources, order information from a physician order entry system (OES), inventory information, claims processing information, billing information, or any other information managed or stored by the EMR system 106.

The medical information processing platform 100 may also be in operative communication with an analytics tool 108. The analytics tool 108 may provide information regarding data analytics regarding any one or more of the other medical information sources in operative communication with the medical information processing platform 100. The analytics tool 108 may also provide information regarding metrics, parameters, data dimensions, pivot tables, values, measures, or any other appropriate data analytics tool to the medical information processing platform 100.

Further still, the medical information processing platform 100 may be in operative communication with a clinical surveillance tool 110. The clinical surveillance tool 110 may comprise an alert generation platform that may provide alert data regarding, for example, antimicrobial stewardship within a facility, infection control, or other appropriate data. As will be appreciated in the discussion presented below, the clinical surveillance tool 110 may leverage information obtained from other medical information sources (e.g., either through the medical information processing platform or by direct communication outside the platform 100) to generate alert data based on logic provided in relation to the information processed. Specific examples of potential alert data is addressed in greater detail below.

The medical information processing platform 100 may also be in operative communication with one or more medical dispensing apparatuses 112. The medical dispensing apparatus 112 may include a drug dispending cabinet, a nurse accessible medication cabinet, or any other appropriate locale where medication and/or medical products may be made available for dispensation. The medical dispensing apparatus 112 may provide information regarding inventory, access requests, dispensation events, or other appropriate information.

One or more pharmacy automation devices 114 may also be in operative communication with the medical information processing platform 100. Such pharmacy automation devices 114 may include, for example, automated syringe processing devices, automated pill dispenser/counter devices, automated compounding devices, dose preparation robots, or other appropriate automated devices utilized in the pharmacy.

Additionally, the medical information processing platform 100 may be in operative communication with a pharmacy workflow management application 116. The pharmacy workflow management application 116 may provide information regarding dose orders, documented preparation steps for doses, dose verification information, product usage, drug usage, drug lot/expiration information, technician workflow information, formulary information, or other information related to pharmacy workflow management.

In the exchanges of information between the medical information processing platform 100 and the medical information sources 102-116 described above, it may be appreciated that different respective exchange protocols and/or data formats may be used to exchange information. For example, the exchange of data between any of the sources 102-116 and the medical information processing platform 100 may be by way of an Health Level 7 (HL7) interface, a print-feed interface, an XML interface, an http format, an html format, a text format, a comma separated value (CSV) format, an SQL format, or any other appropriate format or protocol for exchange of data. Given the potential ability of the medical information processing platform 100 to process such diverse protocols and formats, the medical information processing platform 100 may be scalable to communicate with any number of different sources. For example, the medical information processing platform 100 may receive data in a first format or exchange protocol associated with a first medical information source (e.g., HL7) and in turn provide the data to a second source using a second format or exchange protocol (e.g., XML format).

Figure 4:
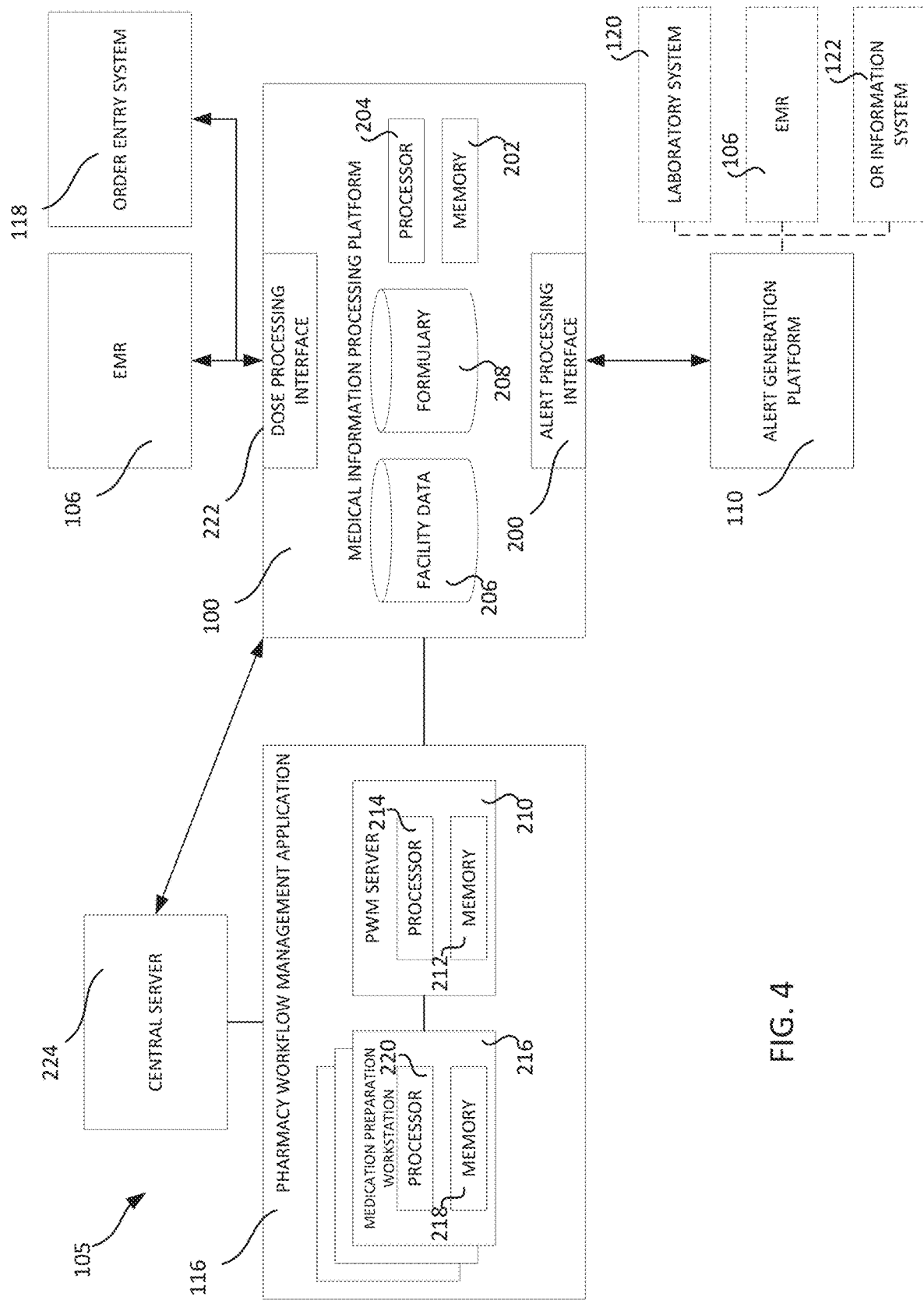
FIG. 4 depicts an embodiment of a medical information processing system to facilitate exchange of information between an alert generation platform and a pharmacy workflow management application.

Turning to FIG. 4, one particular embodiment of a medical information processing system 105 is shown. As a brief overview, a medical information processing platform 100 may be provided that is in operative communication with an EMR system 106, a clinical surveillance tool 110 (e.g., in the particular embodiment also referred to as an alert generation platform 110), and a pharmacy workflow management application 116. As may be appreciated, the medical information processing platform 100 may also be in operative communication with an order entry system 118 (e.g., such as an order entry system 118 that is provided separately from the EMR system 106 which may also include order generation/entry functionality).

The medical information processing platform 100 may include an alert processing interface 200 that is in operative communication with the alert generation platform 110 to receive alert data from the alert generation platform 100. The alert generation platform 110 may be in further communication with an EMR system 106, a laboratory system 120 and/or an operating room information system 122. The EMR system 106, laboratory system 120, and operating room information system 122 are shown in phantom in FIG. 4 to represent a possible embodiment where the alert generation platform 110 may be in direct communication with each of the EMR system 106, laboratory system 120, and operating room information system 122. However, the alert generation platform 110 may alternatively be in operative communication with the EMR system 106, laboratory system 120, and/or operating room information system 122 by way of the medial information processing platform 100. That is, the EMR system 106, laboratory system 120, and/or operating room information system 122 may comprise medical information sources as described in FIG. 3 that may be in operative communication with the medical information processing platform 100 to facilitate exchange of information from any one or more of the EMR system 106, laboratory system 120, and/or operating room information system 122 to the alert generation platform 110.

The alert generation platform 110 may be operative to, based on information received from any one or more of the laboratory system 120, EMR system 106, operating room information system 122, and/or any other appropriate medical information source, generate alert data. The alert data, in certain embodiments, may comprises alerts related to infection control or antimicrobial stewardship.

In an alternative embodiment, the medical information processing platform 100 may be in operative communication with and/or comprise an information aggregator. The information aggregator may be in operative communication with a plurality of medical information sources as described above. In this regard, the medical information processing platform 100 may itself be considered an information aggregator. Additionally or alternatively, the alert generation platform 110 may comprise an information aggregator. In this regard, the medical information processing platform 100 may maintain aggregated medical information and/or be in operative communication with an information aggregator (e.g., the alert generation platform 110) to access aggregated medical information for access and/or display in connection with the pharmacy workflow management application. The aggregated medical information may be used in conjunction with generation of alert data. In this regard, at least a portion of aggregated medical information may be provided in conjunction with alert data generated by the alert generation platform 110. In another embodiment, aggregated medical information may be accessed and/or displayed independent of any alert data. For instance, the pharmacy workflow management application may display the aggregated information to a user of the pharmacy workflow management application in a number of different potential screens or contexts of the pharmacy workflow management application. As will be described below, such aggregated information may be provided in connection with a dose order record listing, a dose order review screen, or a report selection screen, among others.

In any regard, the alert generation platform 110 may be in operative communication with an alert processing interface 200 of the medical information processing platform 100. As may be appreciated, the medial information processing platform 100 may include a memory 202 and processor 204. In this regard, the medical information processing platform 100 may comprise a specifically configured component configured to operate in a predetermined manner as will be described in greater detail below. As such, the specifically configured medial information processing platform may comprise specifically designed software, firmware, and/or hardware for performing certain tasks associated with the medical information exchange described herein. For instance, the memory 202 may store specific instructions that are accessible by the processor 204 to configure the processor 204 to perform functionality associated with the medical information processing platform 100. The memory 202 may comprise a non-transitory computer readable medium such as, for example, an optical disc, non-volatile storage such as a hard drive disc or the like, flash memory, EEPROM memory, or other appropriate computer memory. The memory 202 may in turn store one or more portions, components, or modules of computer-readable instructions that are predefined to specifically configure the processor 204 to execute functionality associated with the medical information processing platform 100. The processor 204, while referred to herein singularly, may comprise a plurality of processor cores or devices that may collectively execute to perform processing in a specifically configured manner. Furthermore, while the memory 202 is referred to singularly, the memory 202 may also comprises a plurality of discrete memory devices.

The medical information processing platform 100 may also comprise a plurality of data stores. The data stores may comprise databases of information stored in a format that facilitates efficient access and storage of information. For instance, the databases may comprise SQL databases or the like. For example, the medical information processing platform 100 may comprise a facility data database 206 and a formulary database 208. The facility database 206 may store information regarding pharmacy operations related to a pharmacy workflow management application 116 as will be discussed in greater detail below. However, the facility database 206 may also store information from any other medical information source with which the medical information processing platform 100 is in communication, such as any of the sources shown in FIG. 3. The formulary database 208 may maintain formulary information for a pharmacy associated with the pharmacy workflow management application 116. In this regard, the formulary database 208 may contain information related to drugs and products that may be utilized in the pharmacy in connection with the preparation of doses or other CSPs.

In any regard, the processor 204 may be configured to process alert data received from the alert generation platform 110 by way of the alert processing interface 200. For instance, the processor 204 may be configured to apply logic to the alert data of the alert generation platform 110. In some embodiments, the logic applied by the processor 204 to the alert data may at least in part be based on information contained in the facility data database 206 and/or the formulary database 208 as will be described in greater detail below.

The medical information processing platform 100 may be in further operative communication with a pharmacy workflow management application 116. In this regard, alert data may be processed by the processor 204 of the medical information processing platform 100 to provide information to the pharmacy workflow management application 116. The pharmacy workflow management application 116 is intended to encompass a plurality of potential system configurations within a pharmacy for execution of the pharmacy workflow management application 116. For example, in an embodiment a single pharmacy workstation comprising a memory and processor may be provided to execute the pharmacy workflow management application 116. In this regard, the memory may store computer-readable instructions in a non-transitory computer readable storage medium that, when accessed by the processor, may specifically configure the processor to execute the pharmacy workflow management application 116.

In another embodiment depicted in FIG. 4, the pharmacy workflow management application 116 may be executed in a distributed pharmacy environment that may include a plurality of pharmacy workstations. For instance, a pharmacy workflow management server 210 may be provided in association with a pharmacy. The pharmacy workflow management server 210 may comprise a memory 212 and a processor 214. In this regard, the memory 212 may store computer-readable instructions in a non-transitory computer readable storage medium that, when accessed by the processor 214, may specifically configure the processor to execute the pharmacy workflow management server 210. Specifically, the pharmacy workflow management server 210 may be in operative communication with one or more other pharmacy workstations. For instance, one or more medication preparation workstations 216 may be in operative communication with the pharmacy workflow management server 210. Again, each of the mediation preparation workstations 216 may comprise a memory 218 and processor 220 for execution of functionality associated with the medication preparation workstation in that the memory 218 may store computer-readable instructions in a non-transitory computer readable storage medium that, when accessed by the processor 220, may specifically configure the processor 220 to execute functionality associated with the medication preparation workstation 216. The medication preparation workstation 216 may comprise a workstation with a user interface comprising a display and an input for interaction by a user with the medication preparation workstation 216. The medication preparation workstation 216 may further include input devices for use in preparation of doses such as, for example, scanners for reading machine readable indicia (e.g., including NDC codes in machine readable barcode format), cameras for acquisition of images related to preparation of doses, foot pedals for interaction with the workstation 216 or other devices. The medication preparation workstation 216 may also include a printer for printing labels or the like in connection with preparation of doses at the workstation.

In any regard, a pharmacy workflow management server 210, a medication preparation workstation 210, or any other appropriate workstation may individually or collectively define a pharmacy workstation that may individually or collectively execute the pharmacy workflow management application 116. Furthermore, while the medical information processing platform 100 is shown as separate from the pharmacy workflow management application 116, it may be appreciated that the medical information processing platform 100 and the pharmacy workflow management application 116 may execute on a single computing device having collective memory and processor capabilities.

As such, one or more pharmacy workstations executing the pharmacy workflow management application 116 may be operative to receive from the medical information processing platform 100 information relating to the alert data processed at the medical information processing platform 100. For instance, the alert data may be processed by the medical information processing platform 100 to generate an alert indication that is provided to the pharmacy workflow management application 116. In turn, the alert indication may be displayed at one or more workstations associated with the pharmacy workflow management application 116. As described above, the pharmacy workstation (e.g., a workstation in operative communication with the pharmacy workflow management server 210 such as the medication preparation workstation 216) may provide a user interface having a display. As such, the alert indication may be provided on the display in connection with the pharmacy workflow management application 116. As will be appreciated in greater detail in the discussion to follow, the user interface of the pharmacy workstation may also present to a user an interactive portion that may allow for a user to access and/or manipulate various features in association with the alert generation platform 110. For instance, the user may interact with the user interface of the pharmacy workstation to select the interactive portion corresponding to the alert indication to launch execution of the alert generation platform 110 on the pharmacy workstation from which the user is interacting with the alert indication. That is, a local instance of the alert generation platform 110 may be executed at the pharmacy workflow management application 116. Accordingly, the alert generation platform 110 may be accessed by way of the pharmacy workstation (e.g., directly or by way of the medical information processing platform 100). For instance, the local instance of the alert generation platform 110 may be a thin client such as a web browser or the like such that the alert generation platform 110 may be accessed to display information provided from the alert generation platform 110 on the pharmacy workstation. As will be discussed in greater detail below, a user may further interact with the alert generation platform 110 by way of the pharmacy workstation to, for example, provide a responsive input to the alert generation platform 110, access reporting functionality of the letter generation platform 110, or otherwise engage with the alert generation platform 110.

FIG. 4 also illustrates the medical information processing platform 100 being in operative communication with an EMR system 106 by way of a dose order processing interface 222. Additionally or alternatively, the medical information processing platform 100 may be in operative communication with an order entry system 118 by way of the dose processing interface 222. In any regard, the medical information processing platform 100 may receive, by way of the dose processing interface 222, information regarding dose orders corresponding to dose is to be administered in connection with the provision of medical care. For instance, the dose order may contain medication data regarding at least one dose order that may be processed by the medical information processing platform 100. Specifically, the medical information processing platform 100 may process the dose order information to generate dose order records that may, for example, be stored in the facility data database 206. In turn, the pharmacy workflow management application 116 may be operative to also process the dose order records and present to a user of the pharmacy workflow management application 116 a dose order listing corresponding to the dose orders managed by the pharmacy workflow management application 116.

The alert indication may be presented at the pharmacy workflow management application 116 in connection with the dose order listing. Additionally or alternatively, the alert indication may be presented at the pharmacy workflow management application 116 connection with a user interface screen of the pharmacy workflow management application 116 corresponding to an interface for pharmacist verification of the dose order. For instance, in either of the foregoing regards, a processor in connection with the pharmacy workflow management application 116 may be operative to process the alert data of the alert generation platform 110 in relation to the dose order listing maintained by the pharmacy workflow management application 116 to associate an alert indication with one or more corresponding respective dose orders in the dose order listing.

In one particular example, the alert data of the alert generation platform 110 may be patient specific alert data. That is, the alert data may regard a specific patient. In this regard, the alert data may comprise a patient identifier corresponding to the patient to whom the alert data applies. In a similar regard, at least one dose order received at the dose processing interface 222 may be a patient specific dose order for administration to a specific patient. In this regard, the patient specific dose order may also comprise a patient identifier. In this regard, upon correlation of the patient identifier for the alert data and the patient identifier for the dose order, the patient specific alert data may be associated with the dose orders for the given patient to which the alert data applies. The correlation of the patient identifiers of the alert data and the dose order may include use of identical patient identifiers by the EMR system 106 and the alert generation platform 110. Alternatively, different patient identifiers may be used by the respective medical information sources that may be associated (e.g., in a look-up table or the like).

In addition, the pharmacy workflow management application 116 and/or the medical information processing platform 100 may be configured to apply logic in relation to the alert data in connection with the processing of the alert data received at the alert processing interface 200. For instance, alert processing rules may define one or more triggering conditions that relate to the presentation and/or actions related to dose orders in relation to an alert indication at the pharmacy workflow management application 116. As such, upon satisfaction of the one or more triggering conditions, the alert indication may be displayed in connection with the pharmacy workflow management application 116. In this regard, alert data may be received the medical information processing platform 100 and/or the pharmacy workflow management application 116 that is not displayed in connection with the pharmacy workflow management application 116 if a triggering condition is not satisfied by the alert data. The alert processing rules that may include the triggering condition may allow for tailoring of the presentation of alert data to a user of the pharmacy workflow management application 116. This may be used to limit the number of alert indications provided to a user of the pharmacy workflow management application 116, thus reducing the potential for alert fatigue whereby a user tends to ignore all alerts if the alert frequency for low severity alert is too high.

In addition, the alert processing rules may define one or more actions to be taken with respect to a given dose order in connection with the alert indication. For example, upon association of a dose order with an alert indication, the corresponding dose order record may be processed by the pharmacy workflow management application 116 according to the alert processing rules. For instance, the status the dose order record for which alert indication is provided may be modified such that the dose order is, for example, put on hold or elevated to a STAT (or otherwise elevated) priority in the event that an alert indication of a given type is received in corresponding relation to the dose order record.

The pharmacy workflow management application 116 may be in further operative communication with a central server 224. The pharmacy workflow management application 116 may communicate data to the central server 224. For example, at least a portion of the data stored in the facility data database 206 may be communicated to the central server 224. The communication of such data may be direct from the medical information processing platform 100 or by way of the pharmacy workflow management application 116. In this regard, the central server 224 may provide backup services in relation to the data processed by the medical information processing platform 100 and/or the pharmacy workflow management application 116. In this regard, alert data generated by the alert generation platform 110 may also be communicated to the central server 224 and provided for purposes of backing up the alert data received from the alert generation platform 110. Further still, the central server 224 may provide the data aggregation point whereby data may be aggregated for purposes of subjecting the data to data analytics the like. In this regard, in the event alert data is provided to the central server 224, the alert data may also be subjected to aggregation for purposes of potential data analytics in relation to the alert data.

The central server 224 may be in operative communication with a plurality of pharmacy workflow management applications 116 and/or a plurality of medical information processing platforms 100. For instance, different respective entities may operate to respective ones of the medical information processing platform 100 and/or pharmacy workflow management application 116. The different respective entities operating the medical information processing platform 100 and/or the pharmacy workflow management application 116 may each be unrelated or unaffiliated parties. However, the central server 224 may be in operative communication with a plurality of the unaffiliated instances of the pharmacy workflow management application 116 and/or medical information processing platform 100 to provide backup data services with respect to the unaffiliated instances. For instance, the central server 224 may be operated by a provider of the pharmacy workflow management application 116 for purposes of backing up data processed by a given facility using the pharmacy workflow management application 116.

Without limiting any of the foregoing discussion, specific embodiments of an interface connection with a pharmacy workflow management application 116 according to the present disclosure is presented in FIGS. 5-13. In this regard, it may be appreciated that the interface screens depicted in connection with FIGS. 5-13 may be presented at and/or generated by one or more pharmacy workstations associated with the pharmacy workflow management application 116. As such, functionality described in connection with the interface screens presented in FIGS. 5-13 may alternatively be provided using different specific configurations of interface screen. That is, the functionality described below can be provided in addition to or as an alternative to the foregoing description of the operation of the pharmacy workflow management application 116 and medical information processing platform 100 described above in connection with the foregoing. As may be appreciated, the processor (e.g., processor 214 or processor 220 discussed above in connection with the pharmacy workflow management application 116) may be configured in a manner as described above to display the various interface screens presented in FIGS. 5-13. Additionally, processing of user inputs received in connection with the interface screens described below may also be accomplished by the processor associated with the pharmacy workflow management application 116. In this regard, the functionality and processing described below in connection with the interface screens may be provided by the processor pharmacy workflow management application 116.

Figure 5:
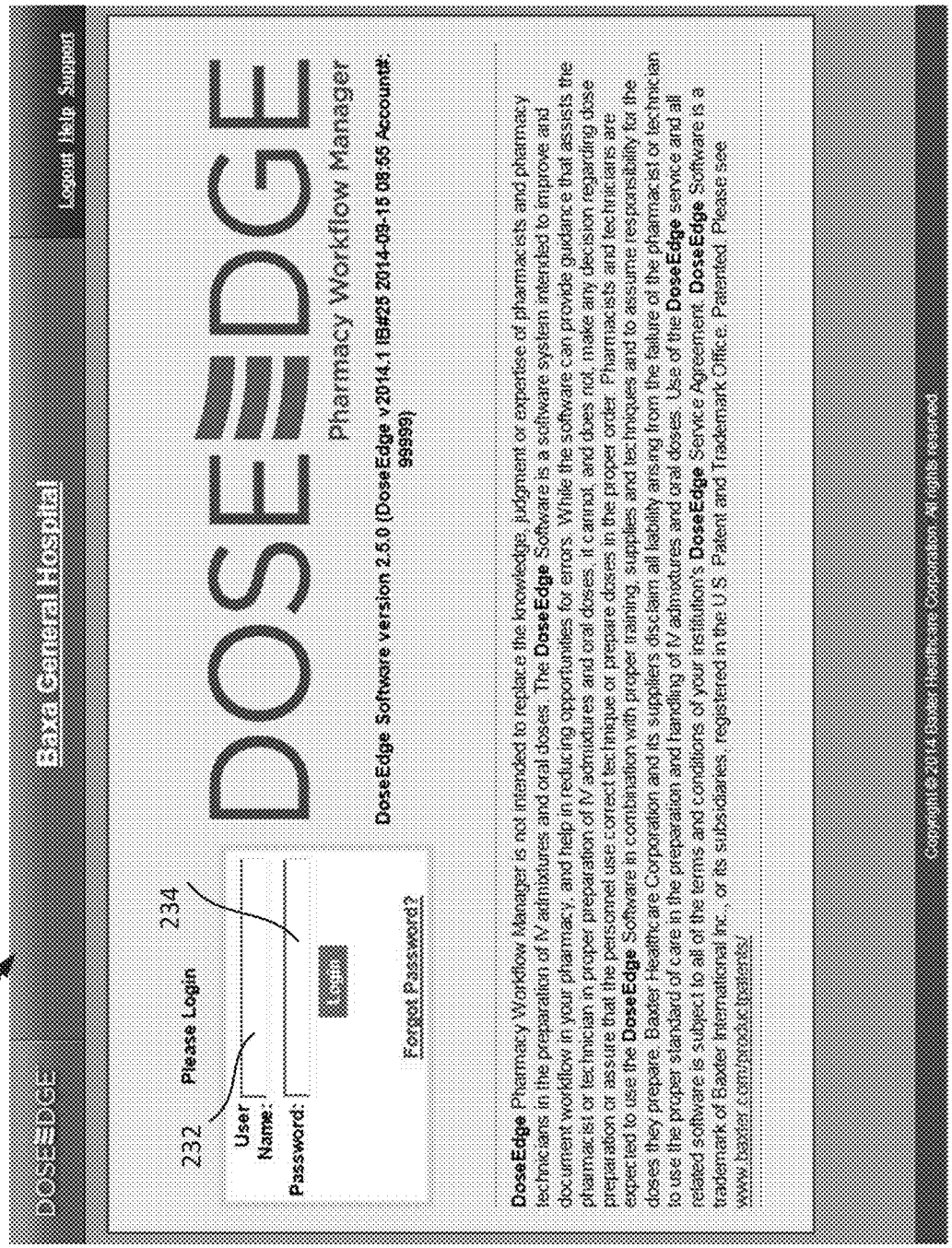
FIG. 5 depicts an embodiment of an interface for accessing a pharmacy workflow management application.
Figure 6:
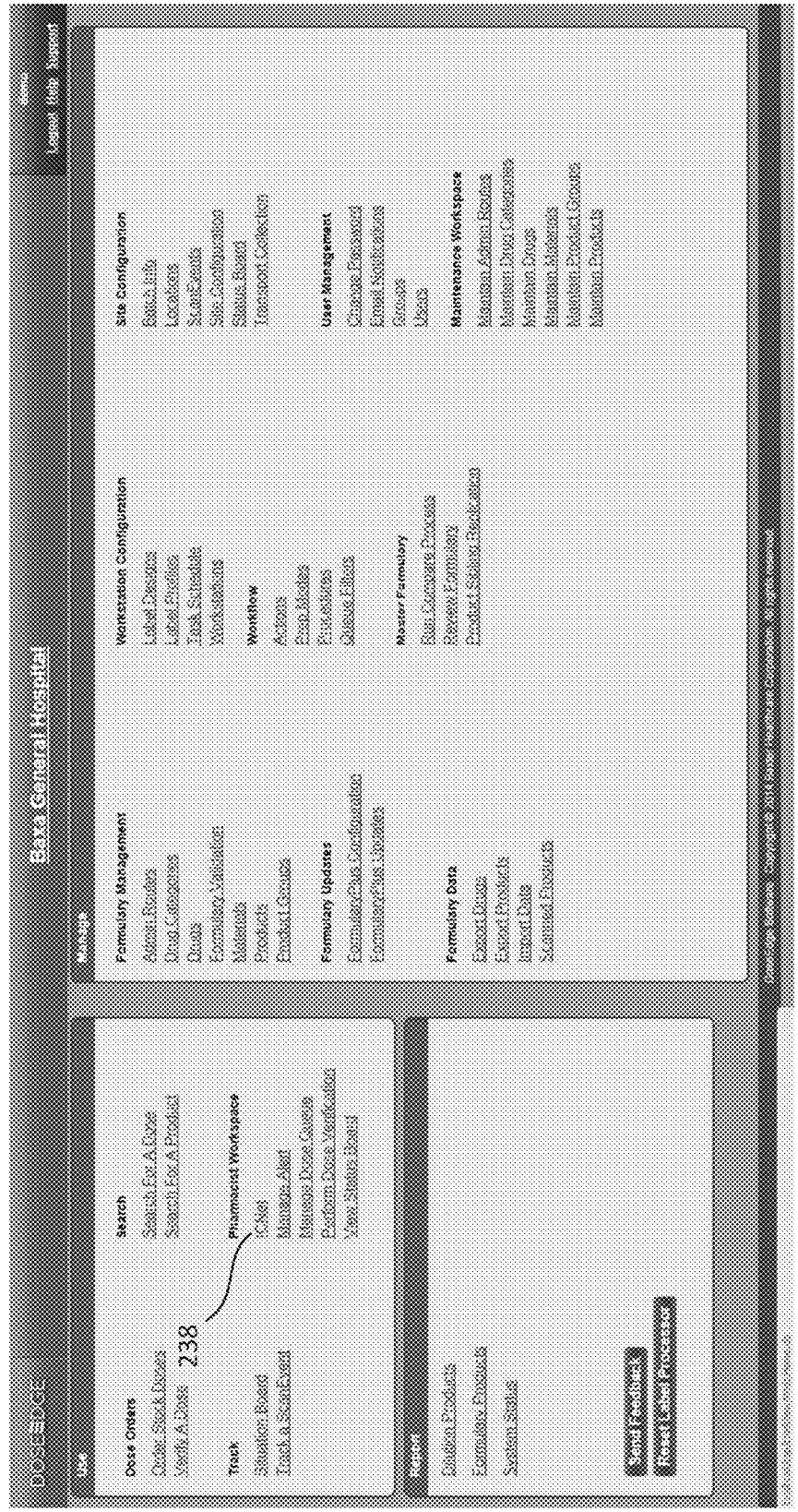
FIG. 6 depicts an embodiment of a navigation interface screen of a pharmacy workflow management application.

Turning to FIG. 5, a login screen 230 is depicted corresponding to the embodiment of a user interface of a pharmacy workflow management application 116. The log in screen 230 may include a user name field 232 and a password field 234. A user of the pharmacy workflow management application 116 may provide a username and the user name field 232 and a password in the password field 234 in order to gain access to the pharmacy workflow management application 116. In this regard, and authenticated username and password match may be required to access the pharmacy workflow management application 116.

Figure 7:
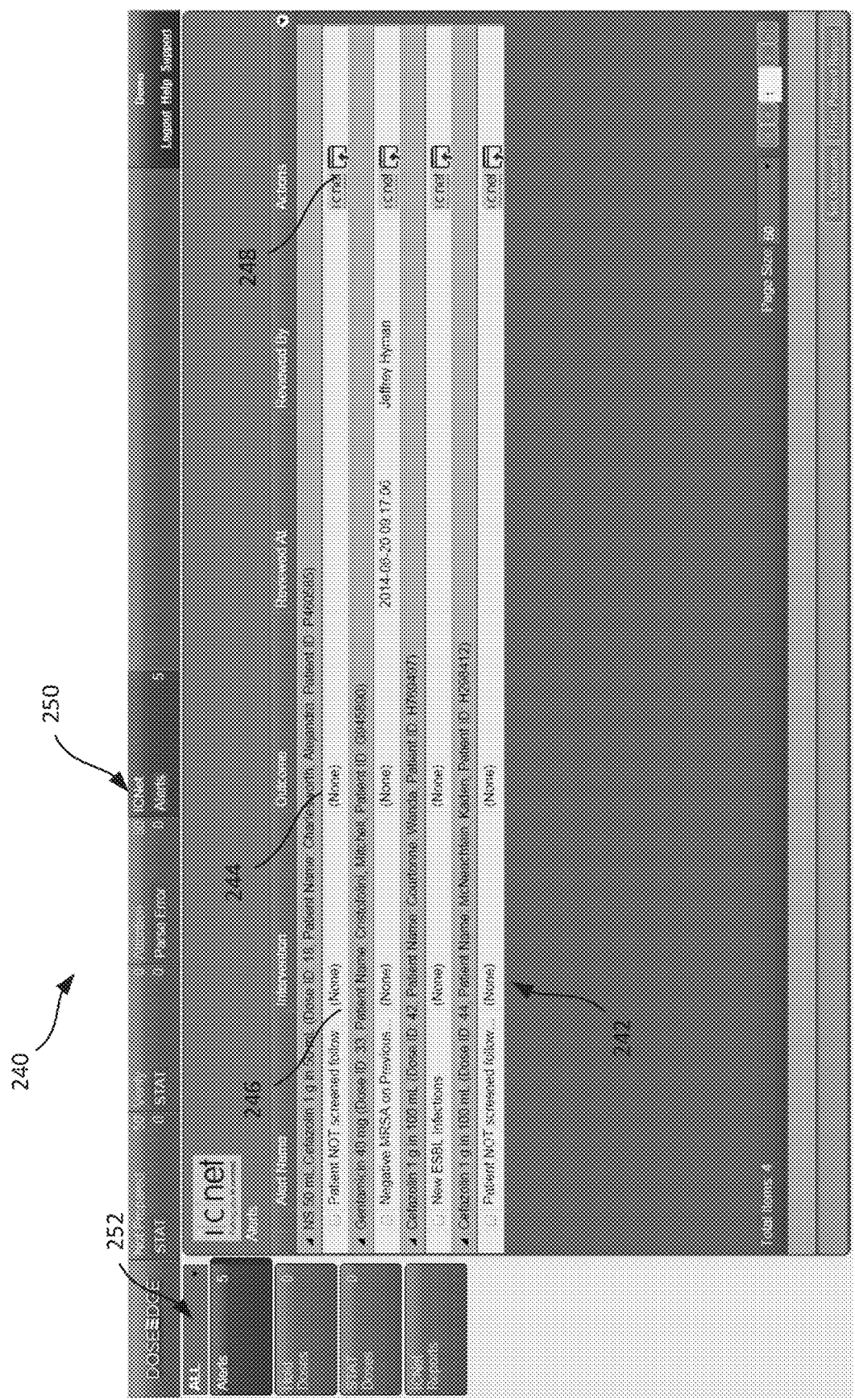
FIG. 7 depicts an embodiment of an alert interface screen of a pharmacy workflow management application.

Upon successful authentication of a user by the pharmacy workflow management application 116 (e.g., in response to provision of the username and password combination by a user), a user may be redirected to a navigation interface screen 236. The navigation interface screen 236 may provide a number of links or other interactive elements to allow for a user to navigate to different interface screens corresponding to different functionality associated with the pharmacy workflow management application 116. Of particular interest to the present discussion, the navigation interface screen 236 may include a link 238 to an alert interface screen 240 (an embodiment of which is depicted in FIG. 7). In addition to the link 238 to the alert interface screen 240, the navigation interface screen 236 may further provide interactive links to allow user to access various functionality of the pharmacy workflow management application 116 such as a dose order listing, a pharmacy verification workspace, formulary management workspaces, or other interfaces for providing functionality in connection with the pharmacy workflow management application 116.

Turning now to FIG. 7 depicting an embodiment of an alert interface screen 240, the alert interface screen 240 may display one or more alert indications corresponding to at least a portion of alert data received by the pharmacy workflow management application 116 and/or the medical information processing platform 100 from the alert generation platform 110. The alert interface screen 240 may include a listing 242 of alert indications 246. The alert indications 246 may be provided in the listing 242 such that the alert indications 246 are organized in any fashion appropriate for display to a user. For example, the alert indications 246 could be listed according to one or more of time of receipt, priority, alphabetical order, severity, or any other appropriate metric. Furthermore, as described above, aggregated medical information may be presented in the absence of any alert indication.

As depicted in FIG. 7, the listing 242 is provided such that alert indications 246 are displayed in corresponding relation to a patient specific dose order record 244 to which the alert indication corresponds. In this regard, the listing 242 may include a dose order record 244 that may provide an indication with respect to the dose order and/or patient associated with the dose order. Accordingly, the alert indications 246 corresponding to the dose order record 244 may be displayed in corresponding relation to the dose order record 244 in the listing 242. In this regard, while only a single alert indication 246 is shown for any single one of the dose order records 244 depicted in FIG. 7, it may be appreciated that a plurality of alert indications 246 could be displayed in corresponding relation to a given dose order record 244. In this case, the additional alert indications 246 may be displayed as a nested list of alert indications 246 relative to a given dose order record 244. The user may interact with a given dose order record 244 to expand or collapse the nested list of alert indications 246 corresponding to the dose order record 244.

In the embodiment depicted in FIG. 7, the alert indications 246 shown in the listing 242 may comprise patient specific alert indications. In this regard, it may be appreciated that the dose order record 244 may include one or more portions of patient information. For example, patient name and patient identifier are provided in connection with the dose order record 244. It may be appreciated that the alert indication 246 may also include a patient identifier corresponding to the patient identified in connection with the dose order record 244. In this regard, the patient identifier may be identical for the dose order record 244 and the alert indication 246. Alternatively, a patient identifier receiving connection with an alert indication may correspondingly associated with a patient identifier for dose order record 244 such that the different respective patient identifiers for the alert indication 246 in the dose order record 244 may be correlated (e.g., in a correlation table or the like). In any regard, the alert indications 246 may be associated with the dose order record 244 in a manner shown in FIG. 7.

The alert interface screen 240 may provide a user certain information regarding the alert indication 246 such as, for example, the alert name, an intervention associated with the alert indication 246, an outcome for the alert indication 246, an indication of when the alert was reviewed, and an indication of the user who review the alert indication 246, etc. In addition, each alert indication 246 may be presented in corresponding relation to an interactive portion 248. As will be described in greater detail below, the interactive portion 248 may be selected by a user of the pharmacy workflow management application 116 to access various functionality associated with the alert generation platform 110.

The alert interface screen 240 may also include a pharmacy workflow management application navigation bar 250. The navigation bar 250 may provide a shortcut to allow for a user to navigate to different respective interface screens of the pharmacy workflow management application 116. For example, the navigation bar 250 may have selectable portions corresponding to a global dose order record listing, a dose order record listing filtered by dose order records awaiting verification by pharmacist, a dose order record listing filtered by dose order records having errors associated therewith, or a dose order record listing filtered by dose order records having alert indications associated therewith. It may be appreciated that the error tab and alert tab may be consolidated into a single listing such that the errors that may be presented in connection with the pharmacy workflow management application 1116 may be processed in a similar manner as the alert indications 246.

A user may select the appropriate portion of the navigation bar 250 to navigate to the alert interface screen 240 that may provide the listing 242 of dose order records 244 filtered by those having alert indications 246 such that the dose order records 244 are shown in corresponding relation to the alert indications 246. The alert interface screen 240 may further include a plurality of navigation tabs 252 that may allow a user to further filter the dose order record listing 242 displayed in the alert interface screen 240. For example, an alert tab may be provided that displays all dose order record listings 244 for which an alert indication is provided 246. Additionally, a hold tab and/or a STAT tab may be provided that, when selected, filters the listing 242 to display only dose order records 244 having an alert indication 246 that caused the corresponding dose order record 244 to have a status change to on hold or STAT depending upon the respective tab selected. In this regard, not all alert indications 246 may result in a dose order record 244 having a status changed. Further still, a tab may be provided to access a report listing corresponding to reports available at the alert generation platform 110 for display in connection with the pharmacy workflow management application 116 as will be described in greater detail below.

In addition to the alert interface screen 240, an alert indication 246 may be provided in other appropriate interface screens of the pharmacy workflow management application 116. One such example is provided in FIG. 8 where a dose verification screen 254 shown. The dose verification screen 254 may show information corresponding to a specific dose order record 244 for purposes of verification by a pharmacist of the dose prepared by a pharmacy technician. In this regard, dose information may be provided for review by the pharmacist including, for example, images of the dose prepared by the pharmacy technician in connection with the dose order. Additionally, the dose verification screen 254 may include an alert indication 246 that corresponds to the given dose order for the dose verification screen 254. That is, in the event an alert indication 246 is present for a given dose order record 244, the pharmacist may be presented the alert indication 246 on the dose verification screen 254 associated with the dose order record 244 at the time the pharmacist is reviewing the dose order information for verification of the dose. While not shown in FIG. 8, the dose verification screen 254 could further include an interactive portion 248 to allow the pharmacist reviewing the dose to access the various functionality associated with the interactive portion 248 described below.

Figure 8:
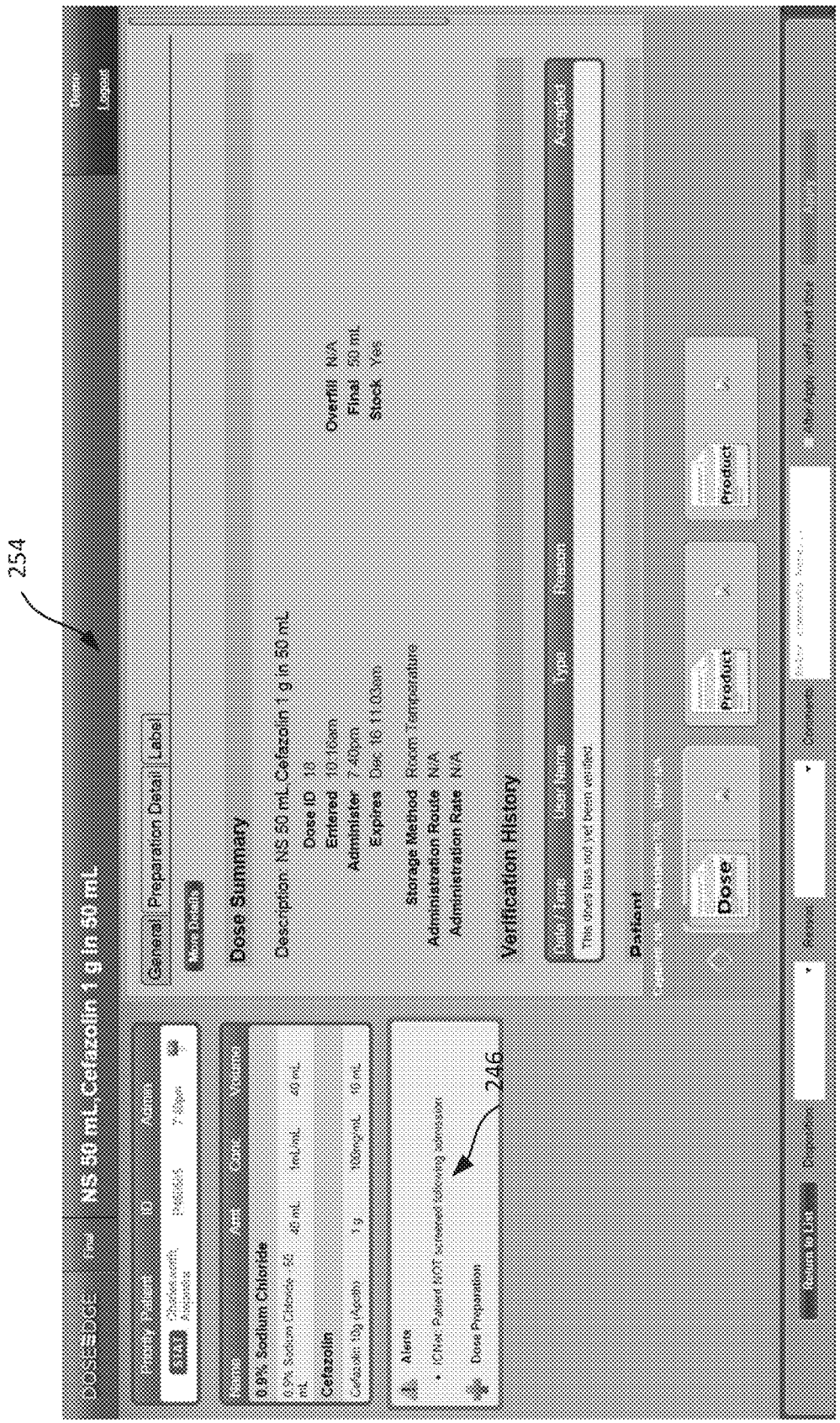
FIG. 8 depicts a dose verification interface having an alert indication presented.

Also, while not depicted in FIG. 8, the dose verification screen 254 may be operative to display aggregated medical information for review by a pharmacist even in the absence of an alert indication. In this regard, the pharmacist may be provided useful aggregated medical information from a plurality of medial information sources for review during the review of the dose order. For instance, the aggregated medical information may be specific to the dose order being verified in the dose verification screen 254. Aggregated medical information regarding a particular drug or product used in the dose may be displayed (e.g., including the number of orders containing the particular drug or product in a given time frame, potential alternatives, possible risks associated with the particular drug or product, etc.). The aggregated medical information may also relate to a given patient associated with the dose order being verified. For instance, information regarding procedures, allergies, medical devices, other ordered drugs/products, or other information particular to the patient may be presented to the pharmacist in connection with the dose verification screen 254.

Figure 9:
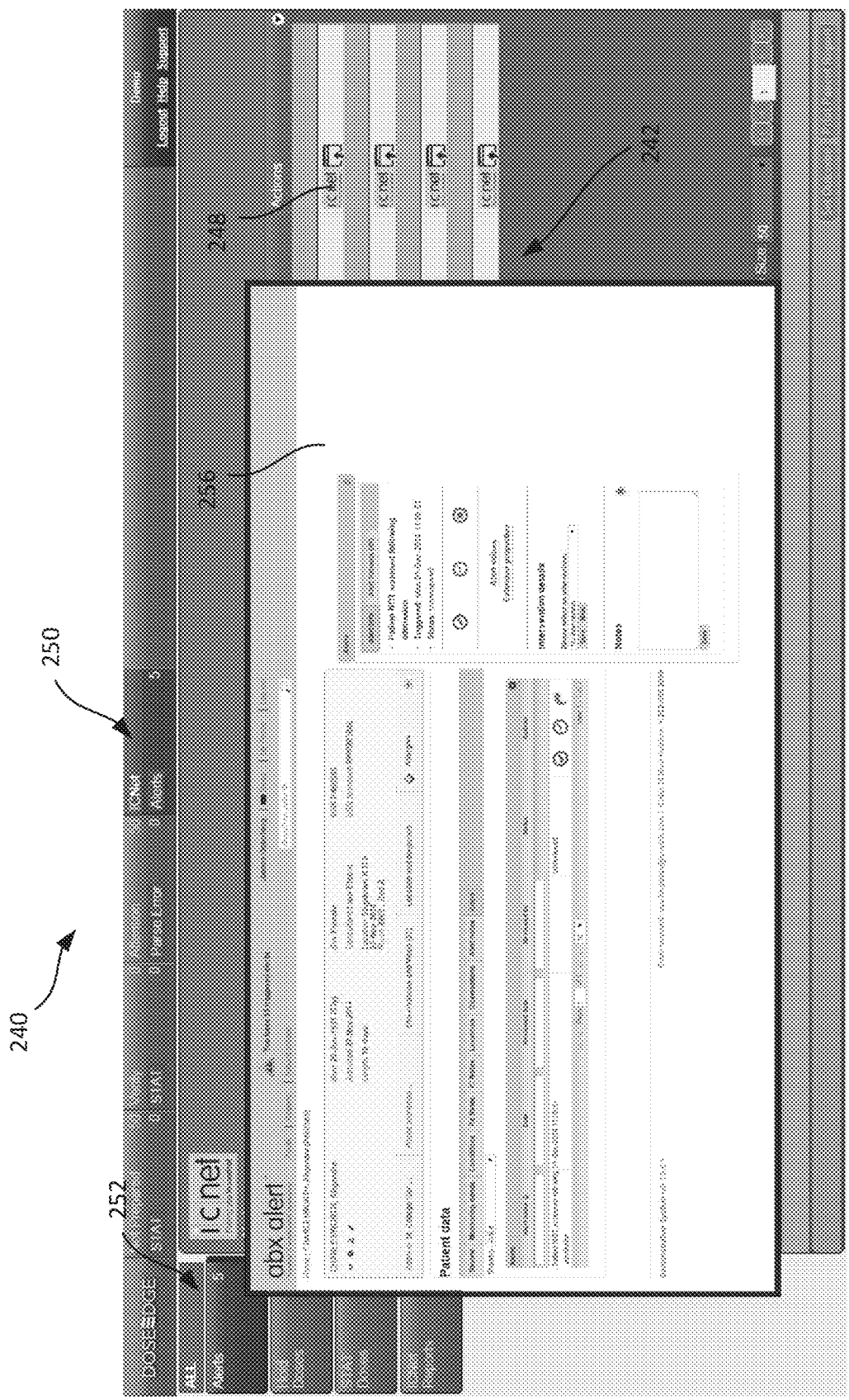
FIG. 9 depicts an embodiment of an interface of a pharmacy workstation having a pharmacy workflow management application and a local instance of an alert generation platform displayed.

FIG. 9 further illustrates functionality associated with an interactive portion 248. For example, with returned reference to FIG. 7, the alert interface screen 240 may provide a listing 242 of alert indications 246 that may each include an interactive portion 248. In this regard, the user may, by way of the user interface of the pharmacy workflow management application 116, select the interactive portion 248 to, for example, launch execution of the alert generation platform 110 (e.g., a local instance of the alert generation platform 110) at the pharmacy work station executing the pharmacy workflow management application 116. This is illustrated in FIG. 9. In FIG. 9, the interactive portion 248 has been selected for a given alert indication 246 in the listing 242. In turn, a local instance 256 of the alert generation platform 110 may be launched at the pharmacy workstation executing the pharmacy workflow management application 116.

As described above, the alert generation platform 110 may be executed remotely from the pharmacy workstation executing the pharmacy workflow management application 116. In this regard, the local instance 256 of the alert generation platform 110 may comprise a thin client application executing on the pharmacy workstation that is in operative communication with the alert generation platform 110 (e.g., by way of the medical information processing platform 100) to display information to the user of the pharmacy workstation in relation to the alert generation platform 110. In this regard, the thin client may be used to present the local instance 256 of the alert generation platform 110 to the user of the pharmacy workstation. The thin client may be, for example, an internet browser or the like that may communicate with the alert generation platform 110 (e.g., using html, http, or other appropriate internet protocol). Alternatively, the alert generation platform 110 may, in at least some embodiments, be executed on the same pharmacy workstation executing the pharmacy workflow management application 116. In such an embodiment where the alert generation platform 110 is executed on the same pharmacy workstation as the pharmacy workflow management application 116, selection of the interactive portion 248 may launch a local native instance of the alert generation platform 110 at the pharmacy workstation to allow for interaction with the alert generation platform 110 by the user of the pharmacy workstation.

In any regard, as depicted in FIG. 9, a local instance 256 of the alert generation platform 110 may be presented to the user of the pharmacy workflow management application 116 on the pharmacy workstation utilized by the user. In this regard, the user may interact with the alert generation platform 110 to, for example, obtain additional information regarding the alert indication 246 presented in the listing 242. Furthermore, in the event that the alert indication 246 is a patient specific alert indication, corresponding patient information may be accessed in the local instance 256 of the alert generation platform 110 at the pharmacy workflow management application 116.

While a number of different types of alert data may be generated by the alert generation platform 110 and received at the medical information processing platform 100, a number of specific examples of alert data and corresponding alert indications are provided below, these examples are intended as demonstrative and not limiting. The alert data may include alerts as follows:

| Alert Indication | Alert Description |
| --- | --- |
| Adverse Drug Event: High Gentamicin trough level: Risk of nephrotoxicity/ototoxicity | Alerting when a lab test for a patient has exceeded the safe threshold for Gentamicin. May be triggered if dose order for Gentamicin for patient in connection with lab results. May result in dose order being put on hold status |
| Adverse Drug Event: Patient on Phenytoin and Warfarin | These drugs are contraindicated. Given together the effects of either can be elevated. May be triggered if patient has dose orders for both drugs in the dose order listing or in patient history information. |
| Adverse Drug Event: Possible Nonsteroidal Anti-inflammatory Hyperkalemia | Patient may have elevated potassium level following prescription of an NSAID. May be triggered with dose order for potassium containing ingredient and if lab results indicate elevated potassium level. |
| Adverse Drug Event: Patient on Warfarin or IV anticoagulant with high INR | Dangerous INR level following prescription of anticoagulant. May be triggered with specific lab results and dose order for Warfarin or IV anticoagulant. |
| CRE from any source | Alerts pharmacist to Multi-drug resistant organism result. May be triggered upon receipt of lab results showing CRE |

| Alert Indication | Alert Description |
| --- | --- |
| Double Beta-lactam Coverage | Shows when the patient is receiving two antibiotics from the same class. This may be wasteful in terms of cost, but also with the potential to further encourage development of antimicrobial resistance. May be triggered upon dose order with two Beta-lactam antibiotics. |
| Gram Negative Resistant to Therapy | Drug resistant bug alert. Indicates that the patient has a positive culture for a gram negative organisms which is resistant to the therapy they are currently receiving. May be triggered upon history of dose order for antibiotic and subsequent lab results showing organism. |
| Gram Positive Resistant to Therapy | Drug resistant bug alert. Indicates that the patient has a positive culture for a gram positive organisms which is resistant to the therapy they are currently receiving. May be triggered upon history of dose order for antibiotic and subsequent lab results showing organism. |
| MRSA Bacteraemia with no Vancomycin/Linezolid therapy | Bug, no drug alert. Alert may trigger if no dose order for Vancomycin or Linezolid is provided after 1 hour of the positive blood infection result being authorized. |
| Narrow spectrum antibiotic used with no isolate | Drug, no bug alert. May be triggered upon a narrow spectrum antibiotic dose order without a specimen result being received for an organism for which the antibiotic is appropriate. |
| New ESBL Infections | Alerts pharmacist to multi-drug resistant organism result. |
| Patient on Glycopeptide or Aminoglycoside with Low CrCl | Possible indicator of nephrotoxicity following use of certain antibiotics. May require specific lab result and dose order for certain antibiotics |
| Patient on Nitrofurantoin | Alerts Pharmacist when a restricted antibiotic prescription has been issued. May trigger upon receipt of dose order. |
| Patient prescribed penicillin class antibiotic and allergic | Alerts to patient who is allergic to penicillin and has a dose order for a penicillin-like antibiotic. |
| Possible Antibiotic or PPI Related *C difficile* | Alerts that a new *C. difficile* infection may have been related to a previous prescription. |
| Possible antibiotic-related hypokalemia | Potassium levels are low and this could be related to the use of Nafcillin, penicillin or gentamicin. May trigger on dose order for suspect drugs in view of specific lab results. |
| Patient allergic to Latex | Alerts to patient who is allergic to Latex. |
| MSSA Bacteraemia with no Cefazolin therapy | Bug, no drug alert. As above, but for Cefazolin. |
| Risk of Nephrotoxicity: High Vancomycin Trough Level | High level of Vancomycin still in blood, may need to consider adjusting dose or timing for next administration. May trigger upon receipt of dose order. May result in dose order being put on hold status. |
| Antibiotic dose order for longer than 4 days. Consider IV to PO switch | Alert to encourage review of the prescription to see if an oral formulation is available, reducing costs and potentially narrowing spectrum. May trigger on receipt of antibiotic dose order for treatment to last longer than 4 days. May result in dose order being moved to hold status. |
| Ceftazadime Usage and Incidence of ESBL | Helps identify correlation between antibiotic usage and incidence of MDRs. |
| Ceftriaxone Days of Therapy | Shows usage of Ceftriaxone in the facility. |
| Epileptic prescribed Clarithromycin | Clarithromycin is one of a group of antibiotics than can trigger a fit in epileptic patients. May trigger upon dose order for patient with epilepsy in patient history. |
| Fluoroquinolone prescribed for longer than 6 days | An example of an alert where the pharmacist might want to review the continued use of the class of antibiotics. May trigger on receipt of dose order for treatment to last longer than 6 days. May result in dose order being moved to hold status. |
| Patient on Carbapenem | Alerts Pharmacist when a restricted antibiotic prescription has been issued. |
| Linezolid/Vancomycin Coverage | Used to alert the pharmacist when a patient has been moved from one therapy to another, giving them opportunity to question the decision. May trigger on receipt of specific dose order sequence. |
| Vancomycin: Consider switch from IV to oral | Patient has received Vancomycin for longer than 3 days, review and consider a switch to an oral medication. May trigger upon dose order for longer than 3 days. May result in subsequent dose order being moved to hold. |

In this regard, the alert generation platform 110 may include additional information received by way of the data connections provided with the alert generation platform 110. For example, the user may be able to review laboratory results, device utilization, medication information, procedure information, treatment information, or other relevant information regarding the patient, the alert indication, a dose order, or other parameter. Furthermore, the user may be operative to review alert data or reporting regarding alerts presented directly in the alert generation platform 110. For instance, the alert data may relate to a microbial organism where no drug has been ordered (e.g., bug, no drug), order of a drug where no microbial organism is present (e.g., drug, no bug), order of an inappropriate drug (e.g., bug, wrong drug), an adverse drug event, abnormal lab results, or any other appropriate alert context.

Additionally, the alert generation platform 110 may maintain responsive inputs in relation to an alert indication provided by the alert generation platform 110. For example, the responsive inputs may correspond to information regarding interventions and/or outcomes associated with an alert. An intervention for an alert indication may include any action, modification of action, or change in action taken in relation to receipt of the alert. Examples of interventions may include monitoring, modification of dose orders, modification of treatment plans, modifications of device utilization, or any other change in connection with the treatment provided to a patient. In this regard, the alert generation platform 110 may provide the intervention information in relation to an alert indication 246. Furthermore, an outcome may be provided that is maintained by the alert generation platform 110 in relation to an outcome associated with the alert indication 244 and/or intervention provided in relation to the alert indication 244. The outcome information may include resolution of diagnoses, further laboratory results, a pharmacy action, or other information.

Figure 10:
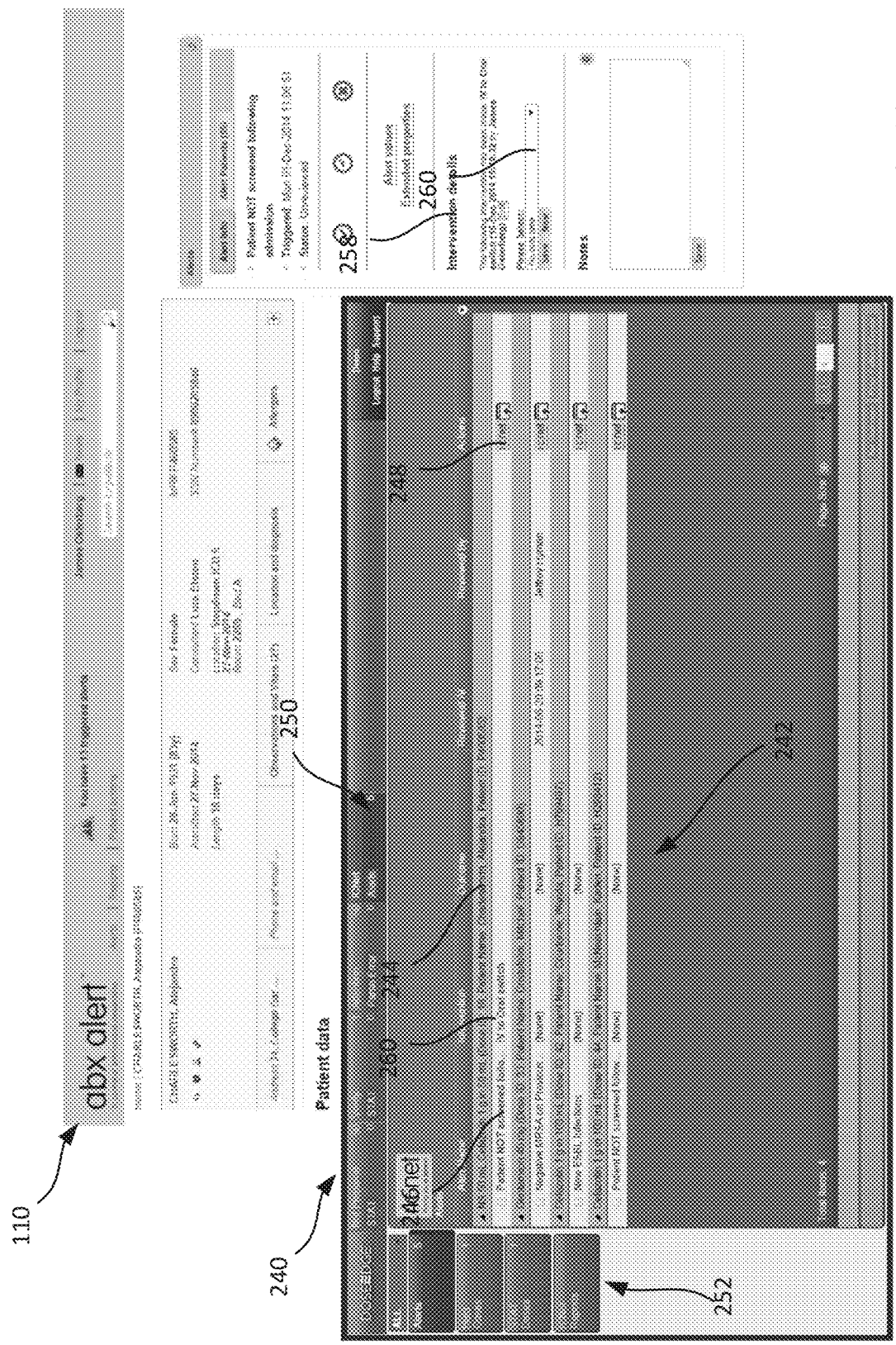
FIGS. 10-12 depict embodiments of a pharmacy workflow management application interface shown in connection with an alert generation platform interface that are in bidirectional communication for information exchange.

Accordingly, as depicted in FIG. 10, the alert generation platform 110 may include an intervention detail portion 258. The alert generation platform 110 may be a local instance 256 executed locally relative to the pharmacy workflow management application 116. Alternatively, the alert generation platform 110 may be executed remotely from the pharmacy workflow management application 116. In any regard, the alert generation platform 110 may allow a user of the alert generation platform 110 to provide intervention details 260. To this end, a user interface element may be provided at the alert generation platform 110 to allow the intervention details 260 to be provided. For example, a list of intervention details may be provided for selection for an intervention detail 260 by a user, a text portion for freeform entry of text corresponding to the intervention detail 260 may be provided, radar buttons may be provided for input of intervention detail 260, or other selection or input modalities may be provided to allow user to provide intervention detail 260 to the alert generation platform 110. Furthermore, outcome details may also be provided in a corresponding manner such that the provision of outcome details at the alert generation platform 110 may be reflected at the pharmacy workflow management application 116.

FIG. 10 also depicts an alert interface screen 240. As may be appreciated, the alert interface screen 240 may provide intervention details 260 provided at the local instance 256 or remotely executed alert generation platform 110. That is, the intervention details 260 provided that the alert generation platform 110 may in turn be provided to the pharmacy workflow management application 116 (e.g., by way of the medication information processing platform 100) and be provided in corresponding relation to an alert indication 246 to which the intervention detail 260 corresponds. Outcome details may also be provided in corresponding relation to an alert indication 246 in the alert listing 242 provided on the alert interface screen 240.

Figure 11:
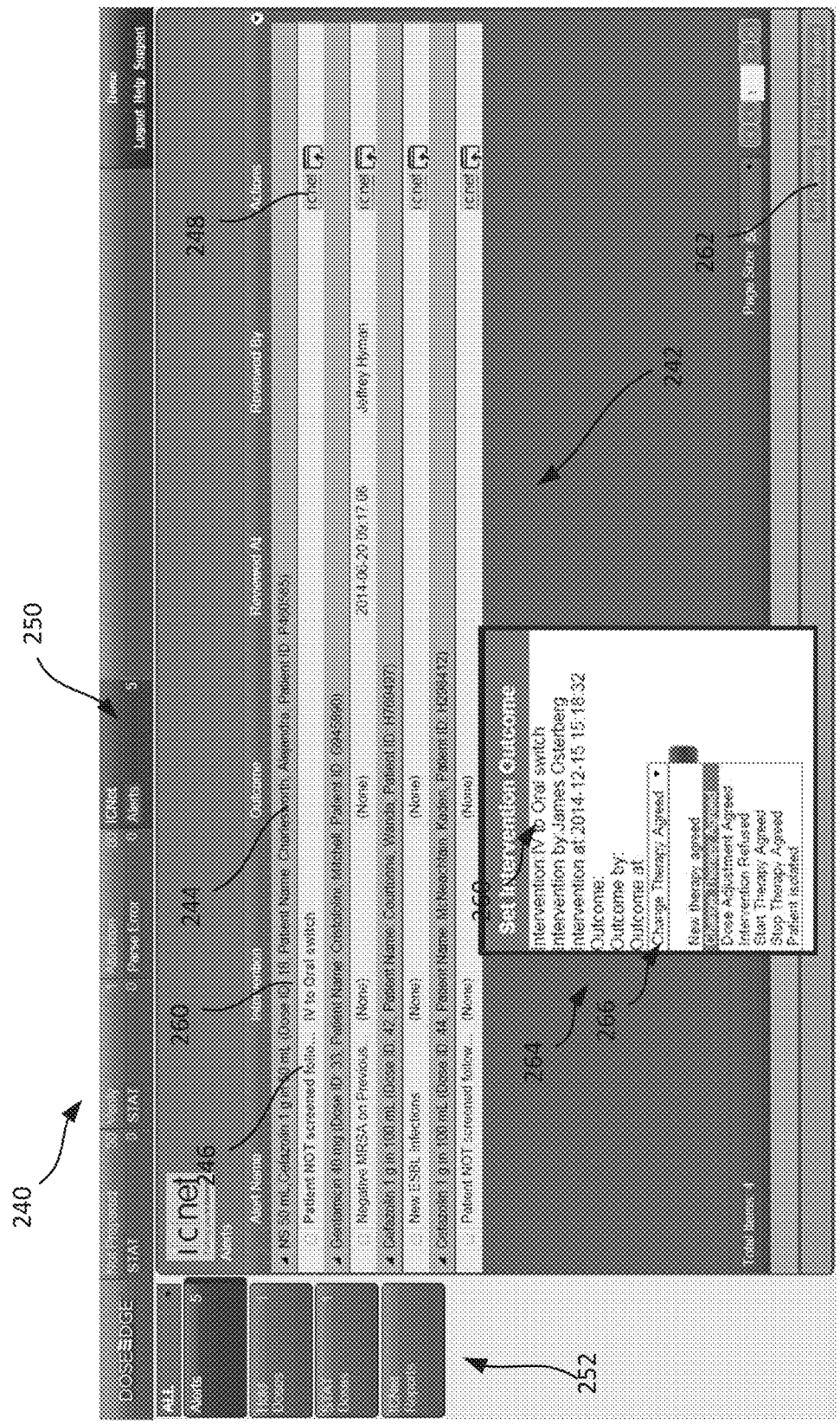

With further reference to FIG. 11, the pharmacy workflow management application 116 may also allow a user to provide information regarding intervention details 260 and/or outcome details 266 in relation to an alert indication 246 presented by the pharmacy workflow management application 116. The alert interface screen 240 may allow user to select an alert indication 246. Upon selection of the alert indication 246, a button 262 may become active that, upon selection, provides the user and intervention/outcome dialog box 264. Using inputs provided in the dialog box 264, the user may be allowed to, at the pharmacy workflow management application 116, provide an intervention details 260 and/or outcome details 266 regarding the selected alert indication 246.

As such, the pharmacy workflow management application 116 may be in bidirectional communication with the medical information processing platform 100 to provide to the alert generation platform 110 the intervention detail 260 or outcome detail 266 provided by the user the pharmacy workflow management application 116. That is, intervention detail 260 and/or outcome detail 266 may be provided to either the pharmacy workflow management application 116 or alert generation platform 110 such that the corresponding other one of the pharmacy workflow management application 116 or alert generation platform 110 may reflect the intervention detail 260 or outcome detail 266.

Figure 12:
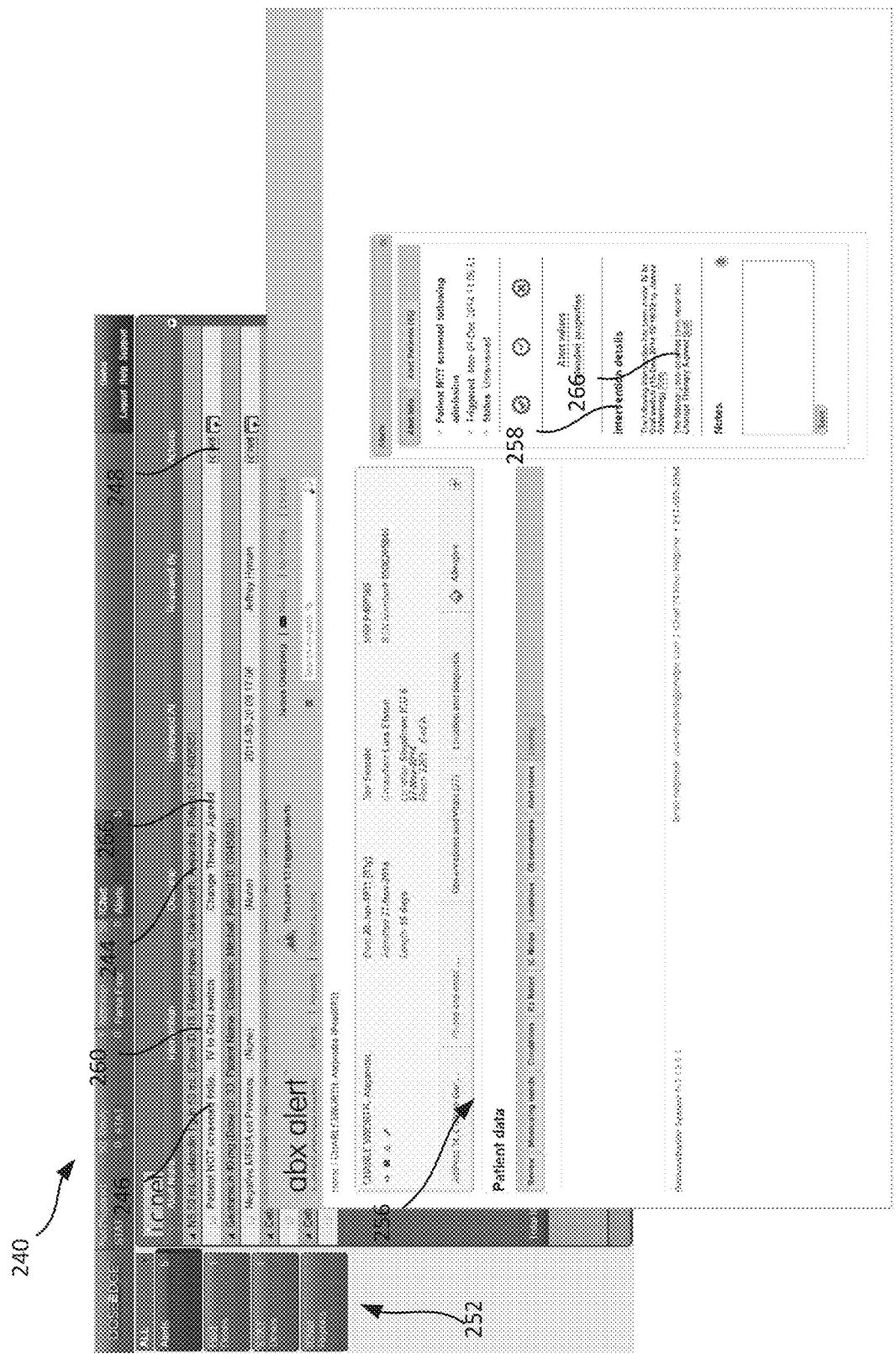

For example, FIG. 12 depicts an alert interface screen 240 and a corresponding instance 256 of the alert generation platform 110. As may be appreciated, outcome details 266 may have been provided by the user of the pharmacy workflow management application 116 utilizing the dialog box 264 for selection of the outcome details 266 at the pharmacy workflow management application 116 for a given one of the alert indications 246. The instance 256 the alert generation platform may receive the outcome details 266 such that the outcome details 266 may be displayed in a intervention detail portion 258 of the instance 256. That is, information provided in relation to the alert indication 246 at the pharmacy workflow management application 116 may be reflected at the alert generation platform 110.

The pharmacy workflow management application 116 may further include functionality in relation to actions to be taken upon receipt of alert indication 246 at the pharmacy workflow management application 116. For instance, the alert generation platform 110 may be operative to provide alert data to the pharmacy workflow management application 116. The pharmacy workflow management application 116 may further have alert processing rules stored in the memory associated with the pharmacy workflow management application 116 that is accessible by a processor associated with the pharmacy workflow management application 116 to configure the processor to process the alert data upon receipt. Specifically, the alert processing rules may define one or more triggering conditions for presentation of the alert indication 246 in the pharmacy workflow management application 116. That is, if the alert data received at the pharmacy workflow management application 116 meets certain predefined criteria defined by the one or more triggering conditions of the alert processing rules, a corresponding alert indication 246 may be provided to the user of the pharmacy workflow management application 116. However, if the alert data does not meet the predefined criteria defined by the one or more triggering conditions of the alert processing rules, the pharmacy workflow management application 116 may not generate any alert indication corresponding to the alert data. The one or more triggering conditions may be selectable or configurable by a user of the pharmacy workflow management application 116 to specifically tailor the alert indications presented to a user of the pharmacy workflow management application 116. Parameters used for the triggering conditions may include patient information of the alert, drug information of the alert, details for the dose order record associated with the alert, or other parameters.

The alert processing rules may also define one or more actions to be taken with respect to a given dose order record 244 in response to receipt of the alert data at the pharmacy workflow management application 116. For example, if the alert data satisfies appropriate alert processing rules, an alert indication 246 may be generated that corresponds to a given dose order record 244 maintained at the pharmacy workflow management application 116. Upon generation of the alert indication 246, further rules may be provided to determine whether the alert indication 246 should result in further action being taken with respect to a given one of the dose order record 244 to which the alert indication corresponds. For example, upon satisfaction one or more triggering conditions, the processor of the pharmacy workflow management application 116 may be operative to execute the one or more actions defined by the alert processing rules with respect to the given dose order record 244 in response to the alert indication 246. For example, a status of the dose order may be modified (e.g., to an on hold status or a stat status). Furthermore, the dose order record may be provided in a specific user interface screen of the pharmacy workflow management application 116. That is, the pharmacy workflow management application 116 may be operative to segregate or separately display dose order records 244 having a given alert indication 246 present for the dose order associated with the alert indication 246.

Figures 13, 14, 15:
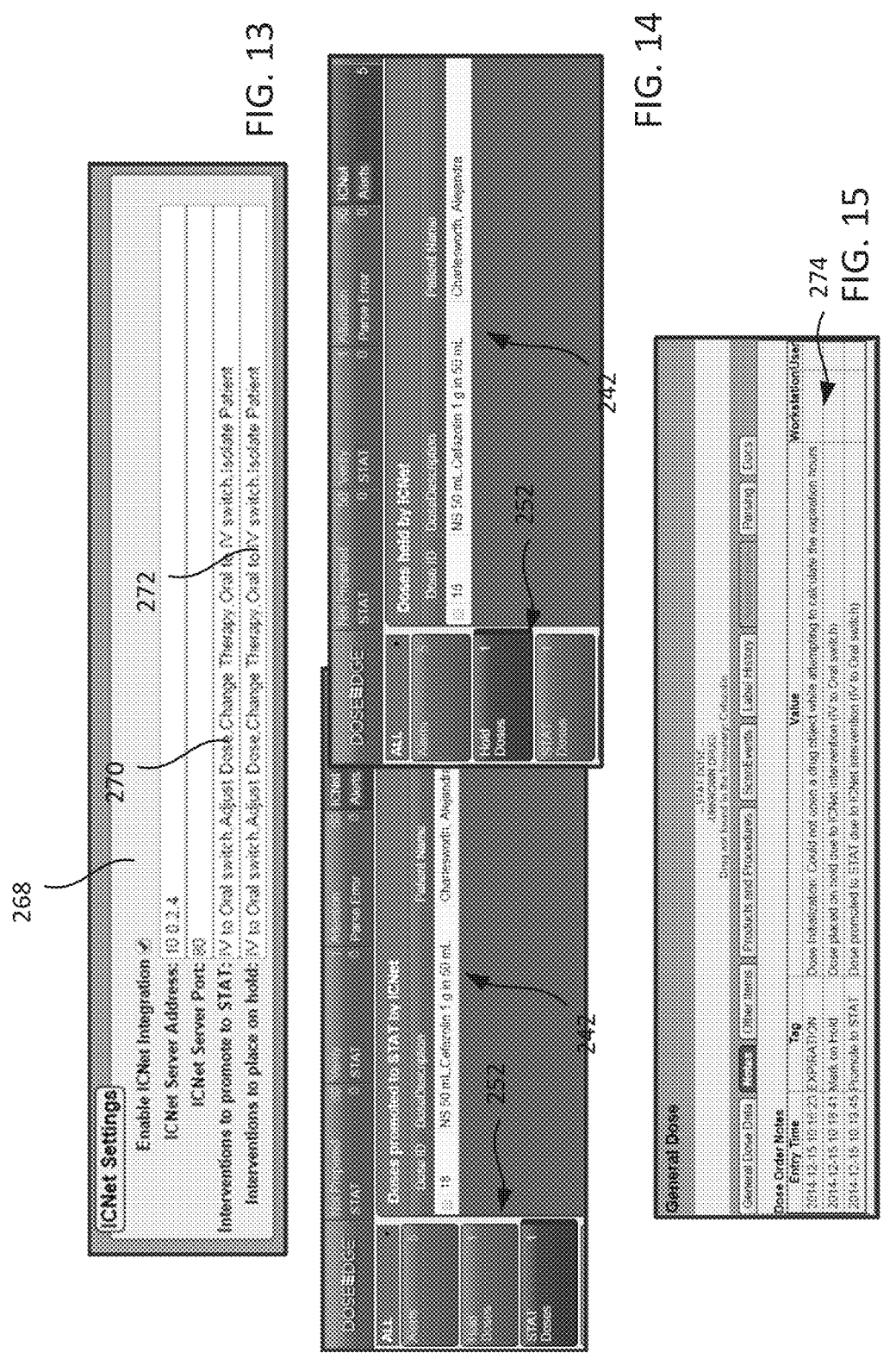

With respect to FIG. 13, a configuration interface 268 shown. The configuration interface 268 may include a plurality of selections that allow for configuration of actions taken in respect to dose order records 246 for which given alert indications 244, interventions 260, and/or outcomes 266 are received from the alert generation platform 110. For example, a first field 270 may allow for configuration of which alert indications 246, interventions 260, or outcomes 266 that, when received, result in the corresponding dose order record 244 to which the alert data corresponds to be promoted to a STAT (or otherwise elevated or prioritized) status. A second field 272 may allow for configuration of which alert indications 246, interventions 260, or outcomes 266 that, when received, result in the corresponding dose order record 244 to which the alert data corresponds to be placed on hold (e.g., delaying or suspending preparation of the dose order).

Furthermore, FIG. 14 depicts utilization of the navigation tabs 252 to allow for selective display of dose order records 244 for which actions have been taken in response to alert data. In this regard, use of the navigation tabs 252 may allow for presentation of a filtered alert listing 242. In this regard, in the left portion of FIG. 14, the STAT doses navigation tab 252 has been selected. In turn, the alert listing 242 may be filtered such that only dose order records 244 that have been promoted to STAT status in response to receipt of an alert indication 246, intervention 260, or outcome 266, are displayed in the listing 242. In the right portion of FIG. 14, the hold doses navigation tab 252 has been selected. In turn, the alert listing 242 may be filtered such that only dose order records 244 that have been modified to hold status in response to receipt of an alert indication 244, intervention 260, or outcome 266, are displayed in the listing 242. Furthermore, FIG. 15 depicts a dose detail screen 274 that may provide information regarding actions taken with respect to a dose order record 244 based on receipt of alert data, an alert indication 244, intervention 260, or an outcome 266 associated with the dose order record 244.

Figure 16:
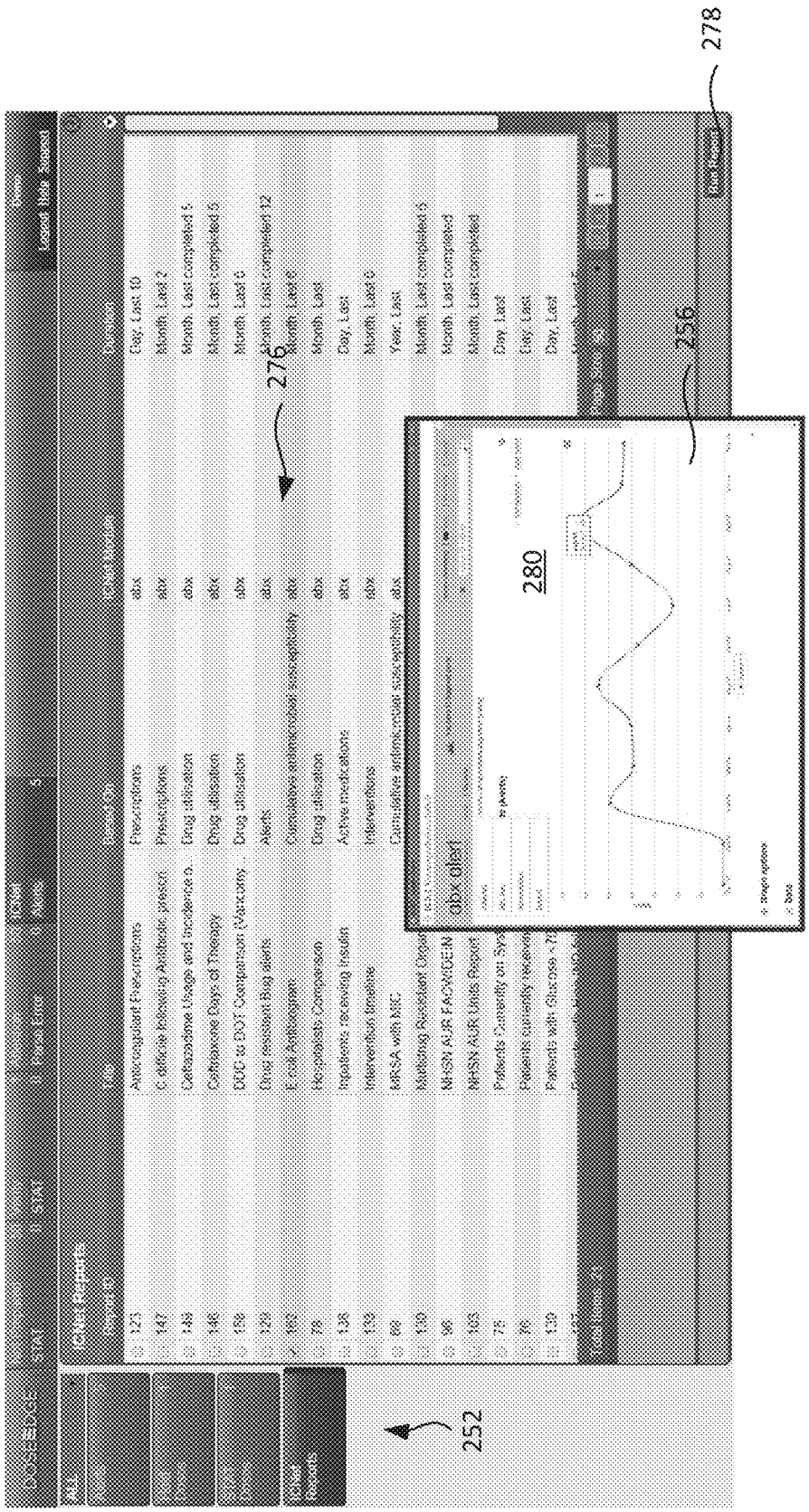
FIGS. 16 and 17 depict embodiments of pharmacy workflow management application interfaces that are capable of presenting report information from an alert generation platform.
Figure 17:
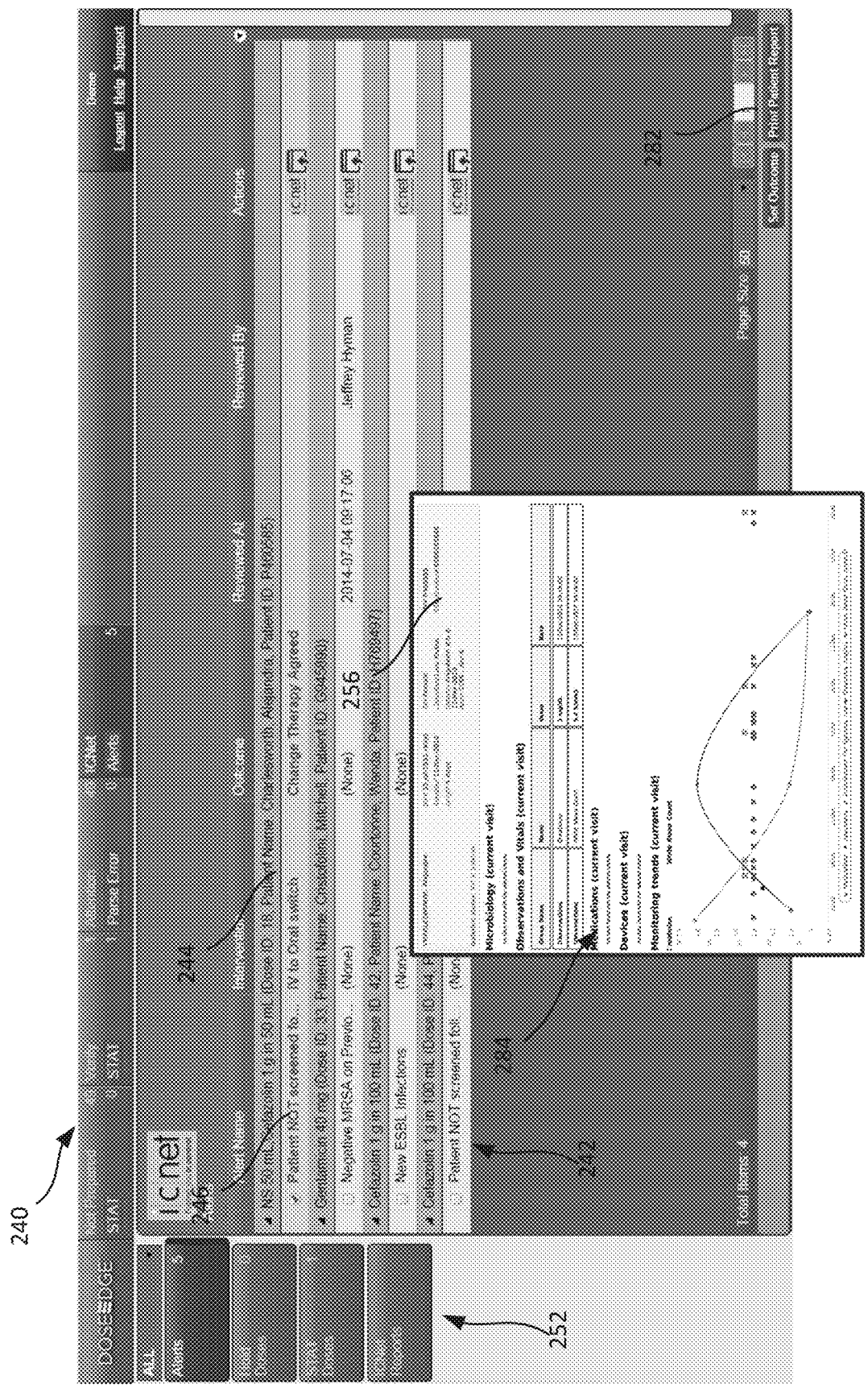

With further reference to FIG. 16, the navigation tabs 252 may be utilized to navigate to an alert generation platform report listing 276. That is, upon selection of the appropriate navigation tab 252, a report listing 276 may be provided in the pharmacy workflow management application 166 interface that allows a user to select a report corresponding to reports provided by way of the alert generation platform 110. That is, the alert generation platform 110 may provide information corresponding to the reports listed in the report listing 276. In this regard, user the pharmacy workflow management application 116 may select a given one of the reports in the report listing 276 and select a run report button 278.

Upon selection of the run report button 278, a local instance 256 of the alert generation platform 110 may be executed at the pharmacy workflow management application 116. Within the local instance 256, a report 280 may be provided by the alert generation platform 110 and may be displayed to the user the pharmacy workflow management application 116. As may be appreciated, plurality of different types of reports may be provided in the listing 276 for access by a user for display in the local instance 256. For example, reports corresponding to the number of prescriptions for a given drug, the way in which drugs are utilized, the frequency of alerts, cumulative antimicrobial susceptibility information, the number of active medications in a given facility, timelines for interventions, or other information may be provided in various ones of the reports provided in the listing 276. As such, the reports provided in the listing 276 may comprise data related to alert data or may be related to aggregated medical information independent of any alert data.

Furthermore, a user may be capable of accessing a specific patient report 284 provided by the alert generation platform 110 from the alert interface screen 240. In this regard, selection of a given alert indication 246 from the alert listing 242 may enable the print patient report button 282 on the alert interface screen 240. Upon selection of the print patient report button 282, a local instance 256 of the alert generation platform 110 may be launched on the pharmacy workstation executing the pharmacy workflow management application 116. The local instance 256 may display a patient report 284 that may provide details regarding the patient to which the selected alert indication 246 corresponds. A number of different types of information may be provided in the patient report to 84. Examples of which may include, microbiology results, patient observations, patient vitals, patient chart notes, medications prescribed to the patient, devices being utilized by the patient, and/or monitoring trends that may present on a timeline various events, resources, or other parameters related to the patient's care.

While the invention has been illustrated and described in detail in the drawings and foregoing description, such illustration and description is to be considered as exemplary and not restrictive in character. For example, certain embodiments described hereinabove may be combinable with other described embodiments and/or arranged in other ways (e.g., process elements may be performed in other sequences). Accordingly, it should be understood that only the preferred embodiment and variants thereof have been shown and described and that all changes and modifications that come within the spirit of the invention are desired to be protected.

What is claimed is:

1. A pharmacy workstation for use in connection with execution of a pharmacy workflow management application, the pharmacy workstation comprising:
   a memory storing the pharmacy workflow management application;
   a processor configured to access the pharmacy workflow management application stored in the memory to execute the pharmacy workflow management application; and
   a dose processing interface in operative communication with the processor, an alert generation platform, and a data source including at least one of a laboratory system, an electronic medical record ("EMR") system, or an operating room information system, the dose processing interface configured to receive dose order data of an order entry system from the data source, the dose order data comprising medication data regarding a patient specific dose order that has been prescribed for a patient,
   wherein the processor in cooperation with the alert generation platform are operative to
      receive, from the data source, infection information indicative of microbial organisms identified in a patient,
      receive, from the data source via the dose processing interface, the medication data indicative of the patient specific dose order that has been prescribed for the patient,
      populate the patient specific dose order into a dose order listing displayed by a user interface of the pharmacy workstation,
      determine, after the patient specific dose order has been prescribed, alert data is to be generated based on the received infection information and the medication data, the alert data indicative that the patient specific dose order conflicts with the infection information indication of the microbial organisms,
      process the alert data in relation to the dose order listing to associate the alert data with the patient specific dose order in the dose order listing,
      determine intervention options based on the received infection information and the medication data when the alert data is generated, at least one of the intervention options including a modification of the patient specific dose order, and
      configure the user interface to present an alert indication corresponding to at least a portion of the alert data and the intervention options to a user at the pharmacy workstation in connection with the pharmacy workflow management application,
   wherein the alert indication and the intervention options are displayed at the user interface of the pharmacy workstation,
   wherein the user interface further comprises an input device and a patient link that, upon selection by the user by way of an input provided using the input device, instructs the processor to display a patient report corresponding to the patient specific dose order and the related alert data in connection with the pharmacy workflow management application,
   wherein the input device is configured to receive a responsive input from the user of the pharmacy workflow management application corresponding to a response to the alert indication, wherein the response to the alert indication is entered, by the user, into the pharmacy workflow management application and includes a selection of at least one intervention option,
   wherein the selection of the intervention option for modifying the patient specific dose order causes the processor to transmit a request to the data source to modify the patient specific dose order,
   wherein the user interface is in bidirectional communication with the alert generation platform to provide the responsive input to the alert generation platform, and
   wherein the responsive input comprises instructions for modification of the patient specific dose order associated with the alert indication.

2. The pharmacy workstation of claim 1, wherein the user interface comprises an interactive portion corresponding to the alert indication.

3. The pharmacy workstation of claim 2, wherein the alert indication comprises the interactive portion.

4. The pharmacy workstation of claim 2, wherein the interactive portion, upon selection by the user by way of an input provided using the input device, configures the processor to launch the alert generation platform at the pharmacy workstation.

5. The pharmacy workstation of claim 4, wherein the alert indication is provided on a second user interface of the pharmacy workflow management application corresponding to a pharmacist workspace comprising a listing of dose orders of the pharmacy workflow management application.

6. The pharmacy workstation of claim 4, wherein the alert indication is provided on a second user interface of the pharmacy workflow management application corresponding to an interface for pharmacist verification of the patient specific dose order.

7. The pharmacy workstation of claim 1, wherein the alert data comprises patient specific alert data.

8. The pharmacy workstation of claim 7, wherein the alert data comprises a first patient identifier corresponding to the patient to whom the alert data applies and the patient specific dose order comprises a second patient identifier corresponding to the patient to whom the patient specific dose order is to be administered, and wherein correspondence of the first patient identifier and the second patient identifier results in the alert data being associated with the patient specific dose order.

9. The pharmacy workstation of claim 1, wherein the alert indication is provided in corresponding relation to the patient specific dose order in the pharmacy workflow management application.

10. The pharmacy workstation of claim 1, wherein the memory comprises alert processing rules accessible by the processor for determining the alert data.

11. The pharmacy workstation of claim 10, wherein the alert processing rules define one or more triggering conditions for presentation of the alert indication in the pharmacy workflow management application.

12. The pharmacy workstation of claim 11, wherein upon satisfaction of the one or more triggering conditions, the alert indication is displayed in corresponding relation to one or more dose orders in the dose order listing of the pharmacy workflow management application.

13. The pharmacy workstation of claim 11, wherein the alert processing rules define one or more actions to be taken with respect to the patient specific dose order in response to the alert indication.

14. The pharmacy workstation of claim 13, wherein upon satisfaction of the one or more triggering conditions, the processor is operative to execute the one or more actions with respect to the patient specific dose order in response to the alert indication.

15. The pharmacy workstation of claim 14, wherein the one or more actions to be taken with respect to the patient specific dose order comprises modification of a status of the patient specific dose order in the dose order listing of the pharmacy workflow management application.

16. The pharmacy workstation of claim 15, wherein the pharmacy workflow management application comprises a second user interface for displaying one or more given dose orders for which one or more actions have been taken in response to one or more corresponding alert indications.

17. The pharmacy workstation of claim 1, wherein the user interface is in bidirectional communication with the alert generation platform, and wherein the processor is operative to configure the user interface to present report data in connection with the pharmacy workflow management application that is received from the alert generation platform in response to a request for the report data from the pharmacy workstation.

18. The pharmacy workstation of claim 1, wherein the pharmacy workstation is in operative communication with a server remote from the pharmacy workstation, wherein the processor is in operative communication with the server for communication of the alert data to the server, and wherein the server stores a copy of the alert data in a server memory located at the server.

19. The pharmacy workstation of claim 1, wherein the alert data comprises information related to at least one of infection control or antimicrobial stewardship.

* * * * *